(12) United States Patent  (10) Patent No.: US 9,277,916 B2
Martin et al.  (45) Date of Patent: Mar. 8, 2016

(54) LAPAROSCOPIC SUTURING INSTRUMENT WITH MANUAL DRIVE

(75) Inventors: David T. Martin, Milford, OH (US); William J. White, West Chester, OH (US); Robert Brik, Brookline, MA (US); Matthew Rohr Daniel, Ann Arbor, MI (US); Daniel J. Prenger, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 305 days.

(21) Appl. No.: 13/419,514

(22) Filed: Mar. 14, 2012

(65) Prior Publication Data

US 2013/0245647 A1    Sep. 19, 2013

(51) Int. Cl.
*A61B 17/04* (2006.01)
*A61B 17/06* (2006.01)
*A61B 17/29* (2006.01)

(52) U.S. Cl.
CPC .......... *A61B 17/0469* (2013.01); *A61B 17/0482* (2013.01); *A61B 2017/06052* (2013.01); *A61B 2017/2936* (2013.01)

(58) Field of Classification Search
CPC ........... A61B 17/0469; A61B 17/0482; A61B 2017/2936; A61B 2017/06052; A61B 2017/0472
USPC .................................. 606/139, 144–148, 232
See application file for complete search history.

(56) References Cited

U.S. PATENT DOCUMENTS

| 5,993,466 A | * | 11/1999 | Yoon .............................. 606/147 |
| 6,056,771 A |   | 5/2000  | Proto |
| 6,071,289 A |   | 6/2000  | Stefanchik et al. |
| 6,086,601 A | * | 7/2000  | Yoon .............................. 606/148 |
| 6,224,614 B1 |  | 5/2001  | Yoon |
| 7,628,796 B2 |  | 12/2009 | Shelton, IV et al. |
| 2010/0100125 A1 | | 4/2010 | Mahadevan |
| 2011/0313433 A1 | | 12/2011 | Woodard, Jr. et al. |

FOREIGN PATENT DOCUMENTS

WO        WO 98/57585         12/1998

OTHER PUBLICATIONS

International Search Report and Written Opinion dated Jun. 25, 2013 for PCT/US2013/030170.
U.S. Appl. No. 13/295,186, filed Nov. 14, 2011, Woodard, Jr. et al.
(Continued)

*Primary Examiner* — Katrina Stransky
(74) *Attorney, Agent, or Firm* — Frost Brown Todd LLC

(57) ABSTRACT

A suture needle driving instrument comprises a shaft, an end effector, and a handle assembly. The end effector is located at the distal end of the shaft and includes a pair of grasping arms operable to grasp and release a needle. The handle assembly comprises a trigger-operated actuation assembly that is operable to rotate a second grasping arm relative to the shaft. The trigger-operated actuation assembly may include a trigger and a trigger gear assembly that is operable to rotate the second grasping arm. A clutch assembly may also be included to selectively couple a drive shaft associated with the second grasping arm to another shaft. The handle assembly may further include a toggle actuation assembly that is operable to grasp and release a needle with the grasping arms. A locking feature may be included to prevent use of the toggle actuation assembly until trigger-operated actuation assembly has been operated.

20 Claims, 51 Drawing Sheets

(56) References Cited

OTHER PUBLICATIONS

U.S. Appl. No. 13/295,203, filed Nov. 14, 2011, Woodard, Jr. et al.
U.S. Appl. No. 13/295,210, filed Nov. 14, 2011, Woodard, Jr. et al.
U.S. Appl. No. 61/355,832, filed Jun. 17, 2010, Woodard, Jr.
U.S. Appl. No. 61/413,680, filed Nov. 15, 2010, Woodard, Jr.

* cited by examiner

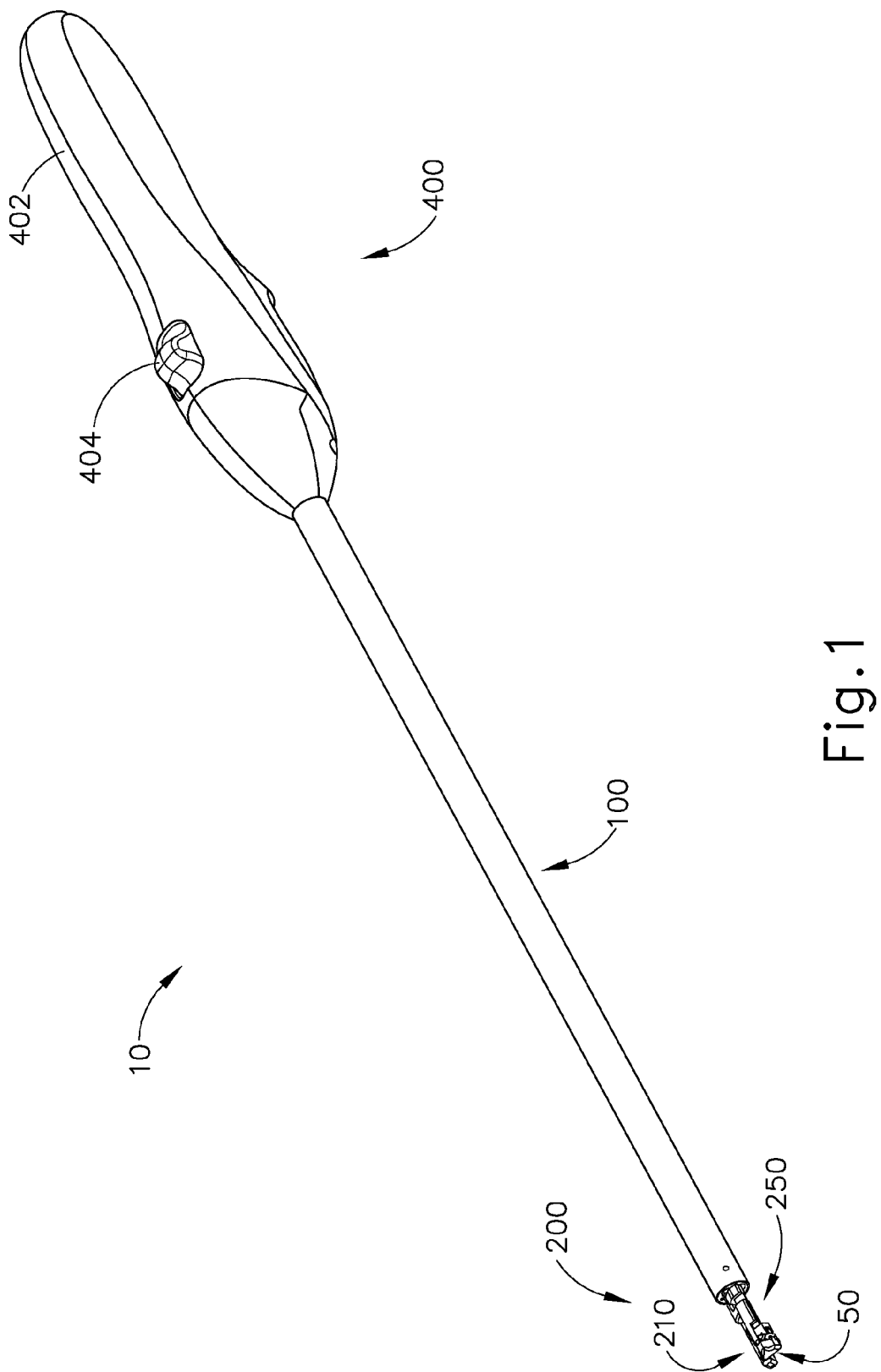

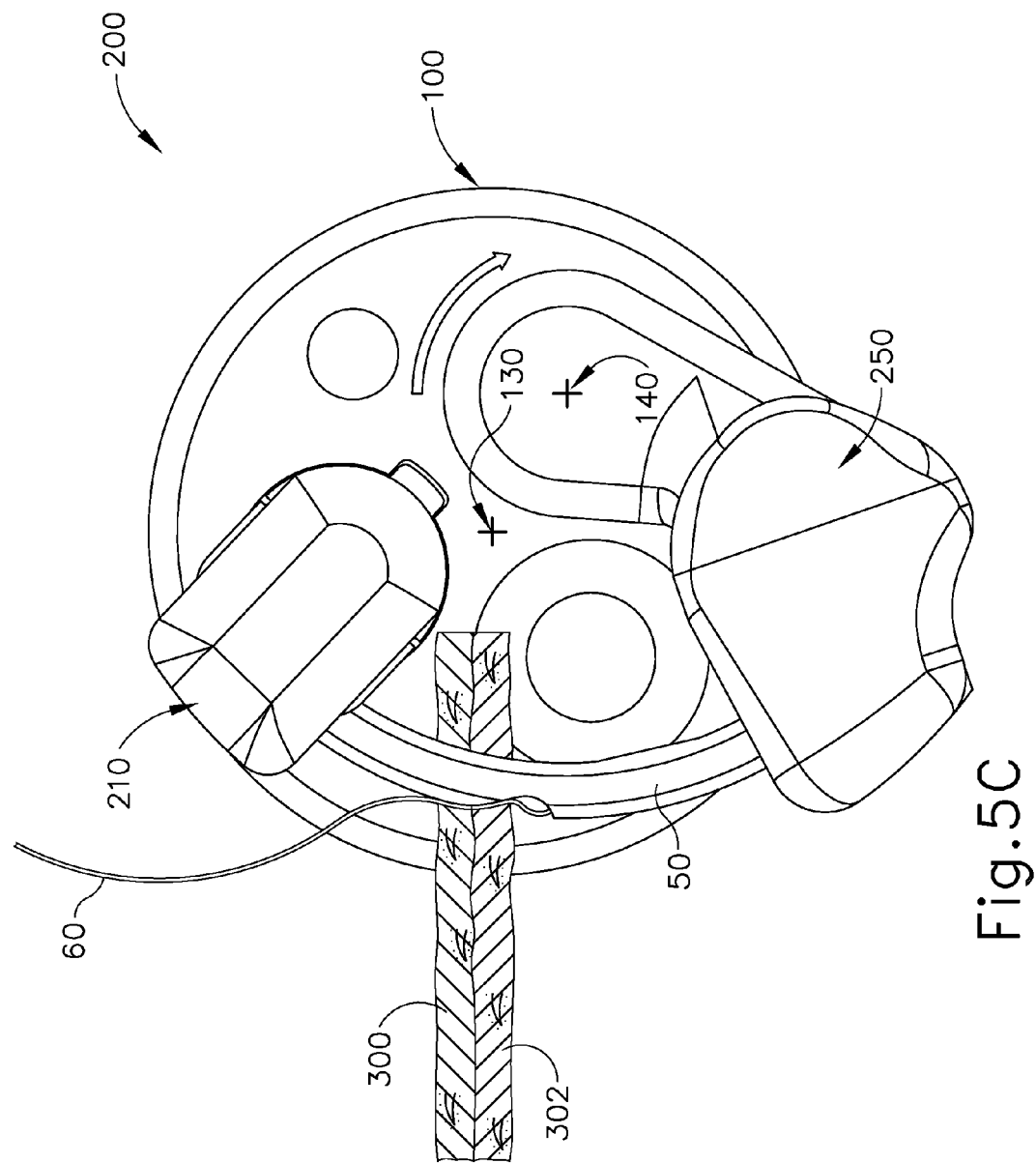

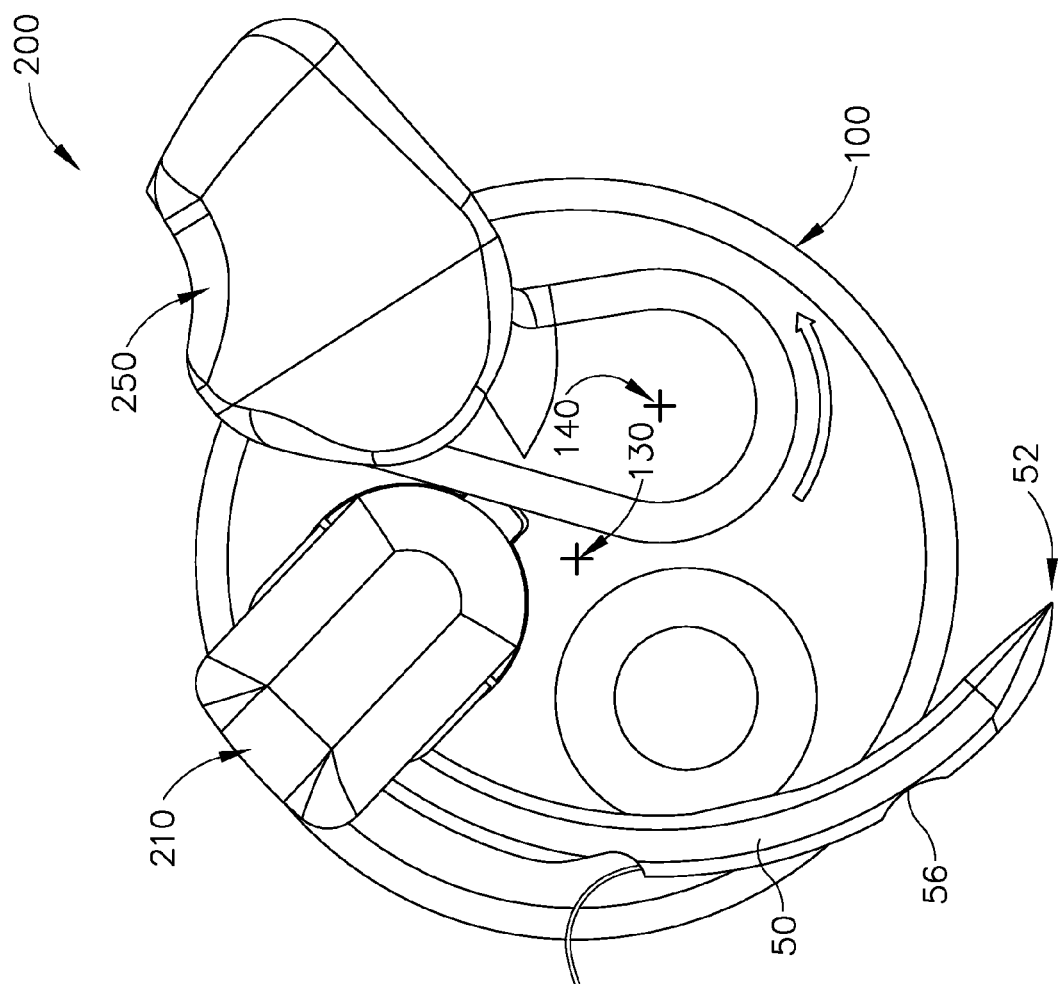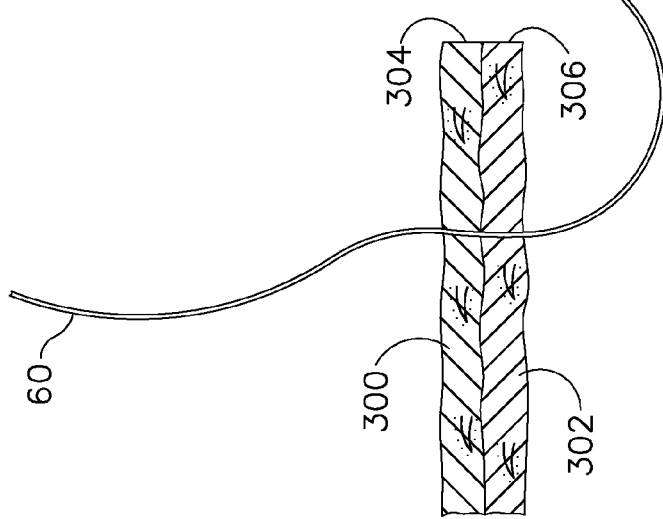
Fig. 5G

LAPAROSCOPIC SUTURING INSTRUMENT WITH MANUAL DRIVE

BACKGROUND

In some settings it may be desirable to perform a surgical procedure in a minimally invasive manner, such as through a trocar or other type of access cannula. Examples of trocars include the various ENDOPATH® EXCEL™ products by Ethicon Endo-Surgery, Inc. of Cincinnati, Ohio. Such trocars may present different inner diameters, such as those ranging from approximately 4.7 mm to approximately 12.9 mm, allowing a surgeon to choose a particular trocar based on a balance of considerations such as access needs and incision size. In some minimally invasive surgical procedures, at least two trocars may be inserted through the abdominal wall of the patient. An imaging device such as an endoscope may be inserted through one of the trocars to provide visualization of the surgical site. A surgical instrument may be inserted through another one of the trocars to perform surgery at the site. In procedures performed within the abdominal cavity, the cavity may be insufflated with pressurized carbon dioxide to provide more room for visualization and manipulation of instruments. In some settings, additional trocars may be used to provide access for additional surgical instruments. Minimally invasive surgery may also be performed through access portals such as the Single Site Laparoscopy Access System by Ethicon Endo-Surgery, Inc. of Cincinnati, Ohio, which provides ports for more than one surgical instrument through a single incision in a patient.

It may also be desirable to use sutures during some minimally invasive surgical procedures, such as to close an opening, to secure two layers of tissue together, to provide an anastomosis, etc. Such use of sutures may be in addition to or in lieu of using other devices and techniques such as clips, staples, electrosurgical sealing, etc. Performing suturing through trocars or other minimally invasive access ports may be more difficult than suturing in an open surgical procedure. For instance, manipulating a needle and suture with conventional tissue graspers through trocars may be relatively difficult for many surgeons. Thus, improved laparascopic surgical instruments may make suturing procedures performed through trocars relatively easier. Examples of surgical instruments configured to facilitate suturing through trocars include the LAPRA-TY® Suture Clip Applier, the Suture Assistant, and the ENDOPATH® Needle Holder, all of which are by Ethicon Endo-Surgery, Inc. of Cincinnati, Ohio. Additional suturing instruments are disclosed in U.S. Pat. No. 7,628,796, entitled "Surgical Suturing Apparatus with Anti-Backup System," issued Dec. 8, 2009, the disclosure of which is incorporated by reference herein; U.S. Pat. No. 6,071,289, entitled "Surgical Device for Suturing Tissue," issued Jun. 6, 2000, the disclosure of which is incorporated by reference herein; U.S. Patent Pub. No. 2011/0313433, entitled "Laparoscopic Suture Device with Asynchronous In-Line Needle Movement," published Dec. 22, 2011, now U.S. Pat. No. 9,168,037, issued Oct. 27, 2015, the disclosure of which is incorporated by reference herein; U.S. patent application Ser. No. 13/295,203, entitled "Laparoscopic Suturing Instrument with Dual-Action Needle Graspers," filed Nov. 11, 2011, now U.S. Pat. No. 8,702,732, issued Apr. 22, 2014, the disclosure of which is incorporated by reference herein; U.S. patent application Ser. No. 13/295,210, entitled "Laparoscopic Suturing Instrument with Perpendicular Eccentric Needle Motion," filed Nov. 11, 2011, now U.S. Pat. No. 8,906,043, issued Dec. 9, 2014, the disclosure of which is incorporated by reference herein; and U.S. Provisional Patent Application No. 61/355,832, entitled "Laparoscopic Suture Device," filed Jun. 17, 2010, the disclosure of which is incorporated by reference herein.

Exemplary suturing needles are disclosed in U.S. Pat. No. 6,056,771, entitled "Radiused Tip Surgical Needles and Surgical Incision Members," issued May 2, 2000, the disclosure of which is incorporated by reference herein; U.S. Pub. No. 2010/0100125, entitled "Suture Needle and Suture Assembly," published Apr. 22, 2010, the disclosure of which is incorporated by reference herein; U.S. Provisional Application Ser. No. 61/413,680, filed Nov. 15, 2010, entitled "Custom Needle for Suture Instrument," the disclosure of which is incorporated by reference herein; and U.S. patent application Ser. No. 13/295,186, entitled "Needle for Laparoscopic Suturing Instrument," filed on Nov. 14, 2011, now U.S. Pat. No. 9,125,646, issued Sep. 8, 2015, the disclosure of which is incorporated by reference herein.

While a variety of devices and methods have been made and used for suturing tissue, it is believed that no one prior to the inventor(s) has made or used the technology described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 1 depicts a perspective view of an exemplary laparoscopic suturing instrument;

FIG. 5C depicts an end elevation view of the end effector and needle of FIG. 2A, during an exemplary third stage of operation;

FIG. 5G depicts an end elevation view of the end effector and needle of FIG. 2A, during an exemplary seventh stage of operation;

Figure 2A:
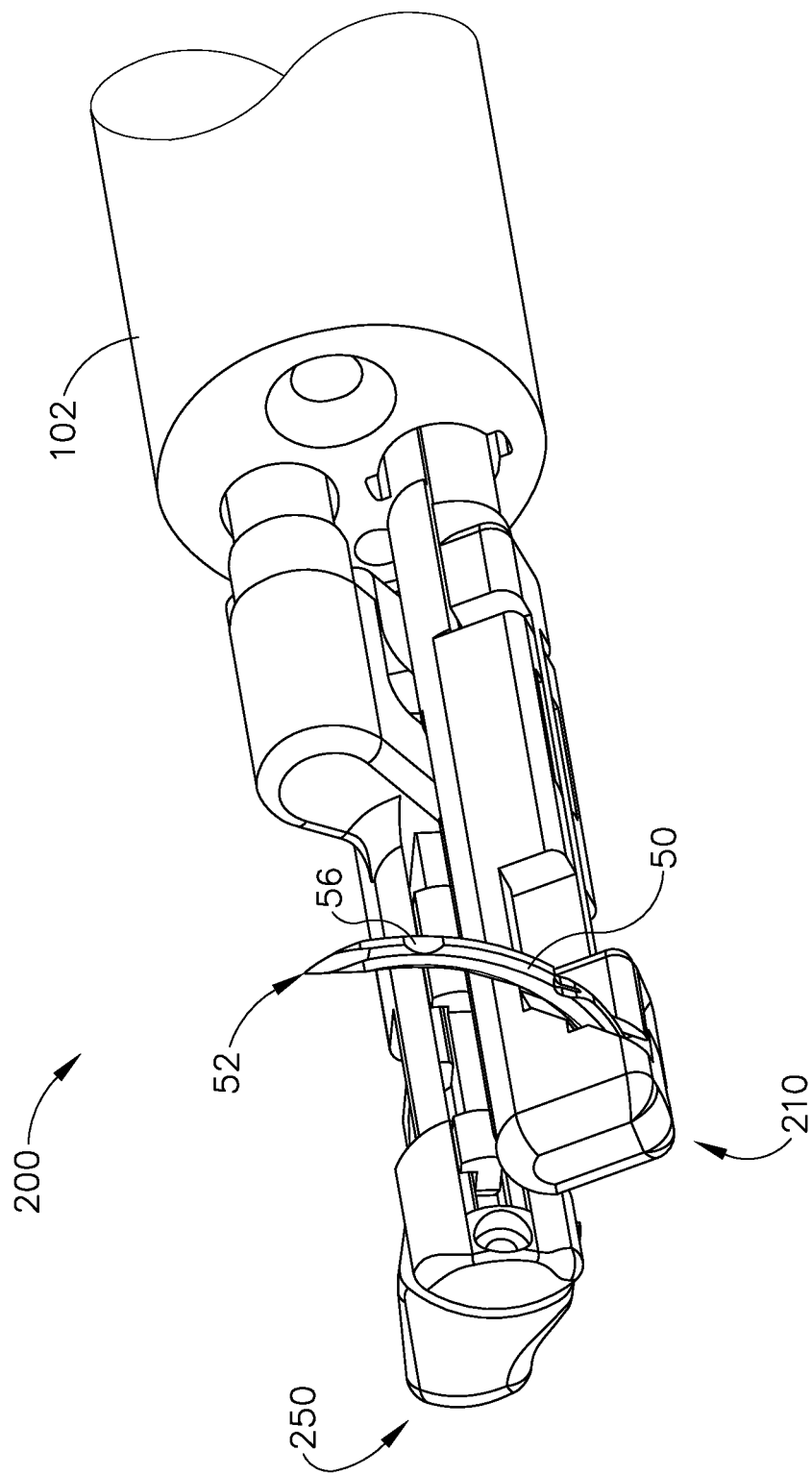
FIG. 2A depicts a perspective view of the end effector of the suturing instrument of FIG. 1 with a needle in a first operational configuration.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It should therefore be understood that any one or more of the teachings, expressions, embodiments, examples, etc.

described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview

FIG. 1 shows an exemplary laparoscopic suturing instrument (10). Instrument (10) of this example includes an exemplary handle portion (400), a shaft (100) extending distally from handle portion (400), and an end effector (200) at the distal end of shaft (100). Handle portion (400) of the present example includes a grip (402) and a toggle (404), though these are merely exemplary. By way of example only, handle portion (400) may be constructed in accordance with at least some of the teachings of U.S. Provisional Patent Application No. 61/355,832, the disclosure of which is incorporated by reference herein; and/or in accordance with at least some of the teachings of U.S. Pat. Pub. No. 2011/0313433, entitled "Laparoscopic Suture Device with Asynchronous In-Line Needle Movement," published Dec. 22, 2011, now U.S. Pat. No. 9,168,037, issued Oct. 27, 2015, the disclosure of which is incorporated by reference herein.

Shaft (100) of the present example has an outer diameter sized to permit shaft (100) to be inserted through a conventional trocar (not shown). Shaft (100) also has a length sized to permit end effector (200) to be positioned at a surgical site within a patient while also allowing handle portion (400) to be manipulated by a user (e.g., a surgeon) from a location outside the patient when shaft (100) is disposed in a trocar. Of course, shaft (100) need not necessarily be dimensioned for use through a trocar. For instance, instrument (10) may be used and/or configured for use in open surgical procedures.

In some versions, shaft (100) includes one or more articulating features, allowing end effector (200) to be articulated to various angles and positions relative to a longitudinal axis (130) (shown in FIGS. 5A-5H) defined by shaft (100). Merely illustrative examples of such articulation are taught in U.S. Provisional Application Ser. No. 61/355,832, the disclosure of which is incorporated by reference herein. Various other suitable ways in which articulation may be provided will be apparent to those of ordinary skill in the art in view of the teachings herein. In addition or in the alternative, shaft (100) may be rotatable about longitudinal axis (130), relative to handle portion (400), to selectively position end effector (200) at various angular orientations about longitudinal axis (130). Of course, a user may rotate the entire instrument (10) about longitudinal axis (130) to selectively position end effector (200) at various angular orientations about longitudinal axis (130).

End effector (200) of the present example includes a first grasping arm (210) and a second grasping arm (250). As will be described in greater detail below, arms (210, 250) are configured to alternatingly throw and catch a curved suturing needle (50) along a path/plane that is substantially perpendicular to longitudinal axis (130) defined by shaft (100). Alternatively, arms (210, 250) may be configured to alternatingly throw and catch needle (50) along a path that is substantially parallel to longitudinal axis (130) defined by shaft (100); or along some other path.

In some versions, arms (210, 250) pass needle (50) back and forth from arm (210) to arm (250) and from arm (250) to arm (210) in an oscillating motion (i.e., back and forth in opposite directions), such that needle (50) does not traverse a circular path as needle (50) is being passed between arms (210, 250). Such action of needle (50) may be referred to as a "reverse reset." In some other versions, needle (50) may be passed between arms (210, 250) along a circular path in a single direction. Such action of needle (50) may be referred to as a "forward reset." By way of example only, arms (210, 250) may move in accordance with at least some of the teachings of U.S. Provisional Patent Application No. 61/355,832, the disclosure of which is incorporated by reference herein; and/or in accordance with at least some of the teachings of U.S. Pat. Pub. No. 2011/0313433, entitled "Laparoscopic Suture Device with Asynchronous In-Line Needle Movement," published Dec. 22, 2011, now U.S. Pat. No. 9,168,037, issued Oct. 27, 2015, the disclosure of which is incorporated by reference herein. Regardless of whether arms (210, 250) move synchronously or asynchronously, arms (210, 250) may be configured to grip and/or compress tissue that is positioned between arms (210, 250) when arms are in approximated positions, which may facilitate passage of needle (50) through the tissue.

Needle (50) of the present example includes a sharp tip (52) (shown in FIG. 2A), a blunt end (54) (shown in FIG. 2C), and a pair of grasping regions (56, 58) (shown in FIGS. 2A, 2C) configured for grasping by arms (210, 250). In particular, grasping regions (56, 58) comprise scallops in the present example, though it should be understood that grasping regions (56, 58) may have various other configurations. A suture (60) (shown in FIGS. 5A-5H) is secured to a mid-region of needle (50). The configuration and relationship of suture (60) and needle (50) provides an exit of suture (60) from needle (50) at an angle that is generally tangent to or oblique relative to the curvature of needle (50). Such an angle may provide reduced drag forces and/or reduced tissue trauma as compared to drag forces and/or tissue trauma that might otherwise be encountered using a needle with a suture that exits at a generally perpendicular angle.

While the example described below includes just a single strand of suture (60) extending from needle (50), it should be understood that two or more strands (60) may extend from needle (50) (e.g., double leg suture, etc.). As yet another merely illustrative example, suture (60) may be secured to blunt end (54) of needle (50) instead of being secured to a mid-region of needle (50). In still other versions, end (54) includes a sharp tip instead of being blunt. It should also be understood that needle (50) may be straight instead of curved in some versions. By way of example only, needle (50) may be constructed in accordance with at least some of the teachings of U.S. Provisional Application Ser. No. 61/413,680; U.S. patent application Ser. No. 13/295,186, entitled "Needle for Laparoscopic Suturing Instrument," filed Nov. 14, 2011; now U.S. Pat. No. 9,125,646, issued Sep. 8, 2015; U.S. Pat. No. 6,056,771, entitled "Radiused Tip Surgical Needles and Surgical Incision Members," issued May 2, 2000; and/or U.S. Pat. Pub. No. 2010/0100125, entitled "Suture Needle and Suture Assembly," published Apr. 22, 2010, the disclosures of which are incorporated by reference herein. Still other suitable configurations for needle (50) will be apparent to those of ordinary skill in the art in view of the teachings herein.

It should also be understood that needle (50) may be constructed using various techniques. By way of example only, needle (50) may be constructed using metal-injection-molding (MIM) processes. Needle (50) may also be formed from a sheet, wire, tube, extrusion, or other components that are bent, stamped, coined, milled, otherwise machined, and/or otherwise formed. Other suitable ways in which needle (50) may be constructed will be apparent to those of ordinary skill in the art in view of the teachings herein.

II. Exemplary End Effector

As noted above, end effector (200) comprises a pair of grasping arms (210, 250) that are operable to selectively grasp needle (50) during a suturing procedure. Grasping arms (210, 250) are exposed relative to an endcap (102) of shaft (100), shown in FIGS. 2A-2C. Each grasping arm (210, 250) extends along a respective axis that is parallel to yet offset from longitudinal axis (130) of shaft (100), shown in FIGS. 5A-5H. First grasping arm (210) maintains a fixed rotational position relative to shaft (100) during operation of instrument (10) in the present example. In some other versions, first grasping arm (210) is rotatable about its own longitudinal axis, relative to shaft (100). Second grasping arm (250) of the present example is rotatable about its longitudinal axis (140). Such motion can be seen in the series shown by FIGS. 2A-2C.

Figure 2B:
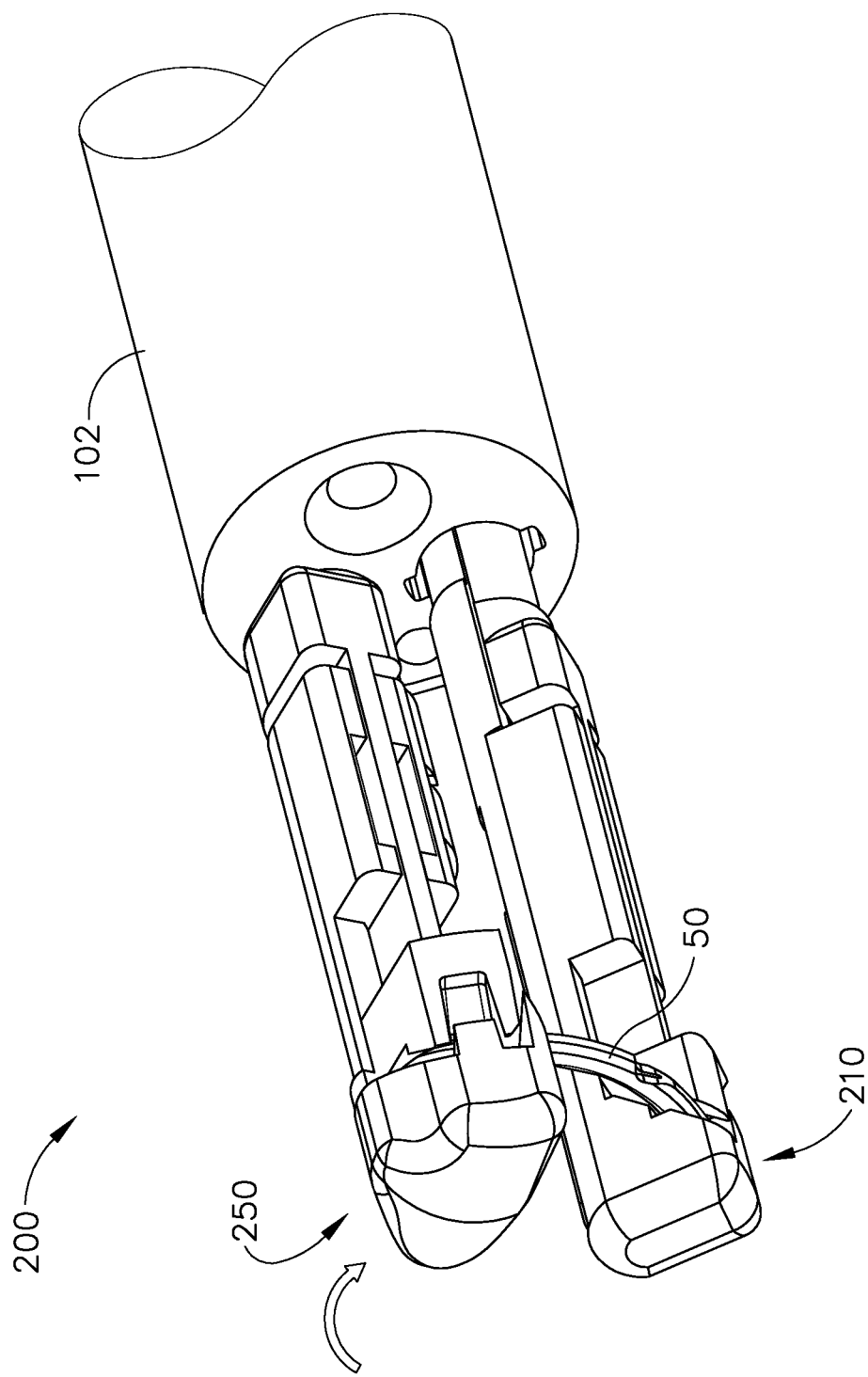
FIG. 2B depicts a perspective view of the end effector and needle of FIG. 2A, in a second operational configuration.
Figure 2C:
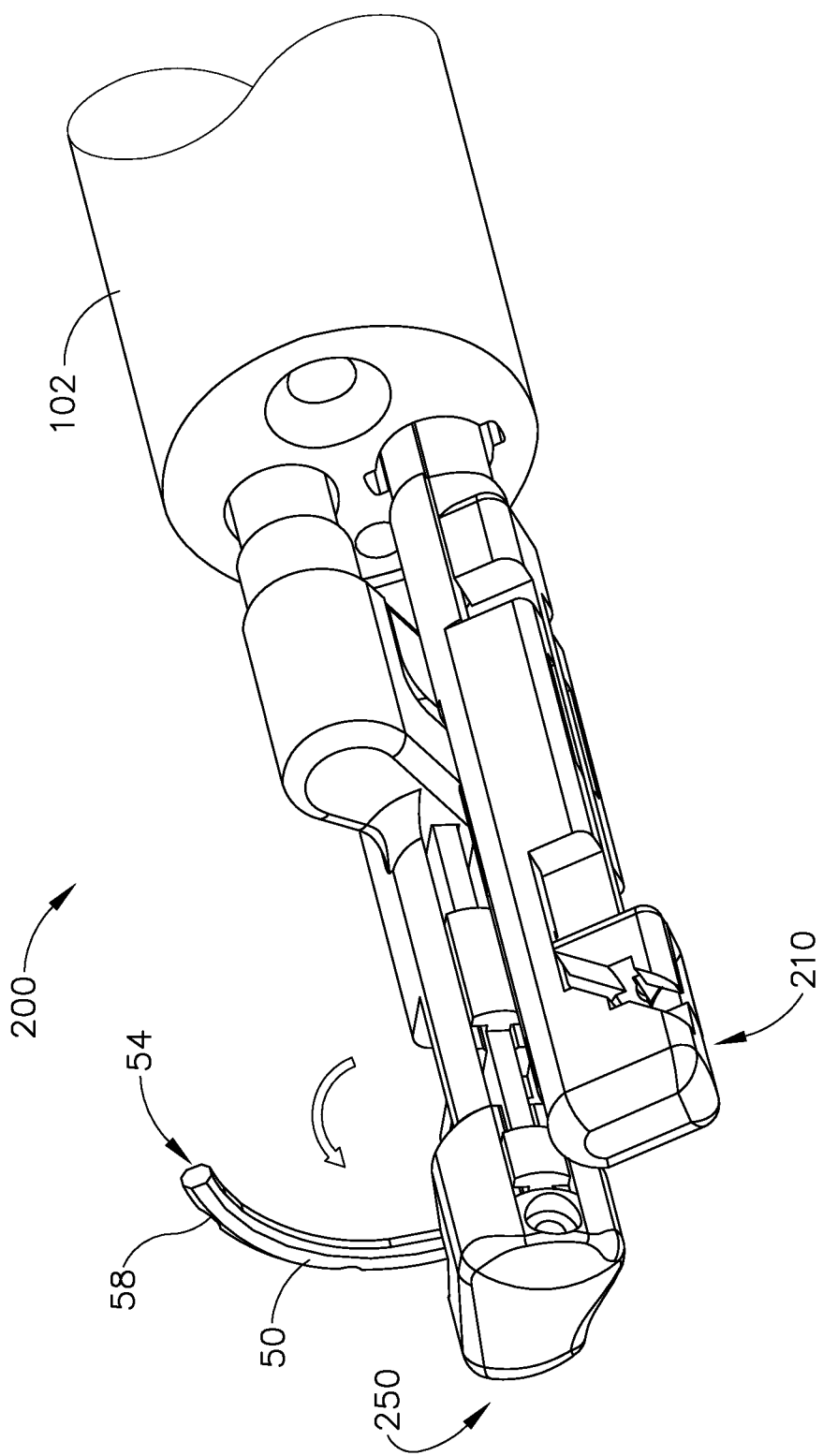
FIG. 2C depicts a perspective view of the end effector and needle of FIG. 2A, in a third operational configuration.

FIG. 2A shows first grasping arm (210) grasping needle (50), with second grasping arm (250) rotated away from needle (50), exposing sharp tip (52) of needle (50). FIG. 2B shows second grasping arm (250) rotated toward needle (50) to a position enabling second grasping arm (250) to grasp needle (50) and first grasping arm (210) to release needle (50). FIG. 2C shows second grasping arm (250) rotated away from first grasping arm (210), pulling needle (50) away from second grasping arm (250). After reaching this position, second grasping arm (250) may be rotated back to the position shown in FIG. 2B, to thereby pass needle (50) back to first grasping arm (210); then rotated back to the position shown in FIG. 2A to start the cycle over again.

In the examples described herein, needle (50) is driven along a plane that is substantially perpendicular to longitudinal axis (130) of shaft (100). In some other examples, needle (50) is driven along a plane that is oblique relative to longitudinal axis (130) of shaft (100) or substantially parallel to longitudinal axis (130) of shaft (100). During some uses of instrument (10), needle (50) may deviate from the desired perpendicular plane. Such deviation may be due to manufacturing tolerances, deflections caused by tissue or other structures, and/or for other reasons. Such deviation may be accentuated by using a needle (50) having a relatively great length. As will be described below, end effector (200) of the present example is configured to readily accommodate and correct such off-plane deviations. In other words, arms (210, 250) are operable to grasp needle (50) even in instances where needle (50) has deviated away from the expected perpendicular plane of motion; and arms (210, 250) are further operable to redirect a deviated needle (50) back onto the expected perpendicular plane of motion.

It should be noted that suture (60) is omitted from FIGS. 2A-2C for clarity. Various components of grasping arms (210, 250) will be described in greater detail below. Various ways in which grasping arms (210, 250) may be used will also be described in greater detail below. Other suitable components of and uses for grasping arms (210, 250) will be apparent to those of ordinary skill in the art in view of the teachings herein.

A. Exemplary First Grasping Arm

Figure 3A:
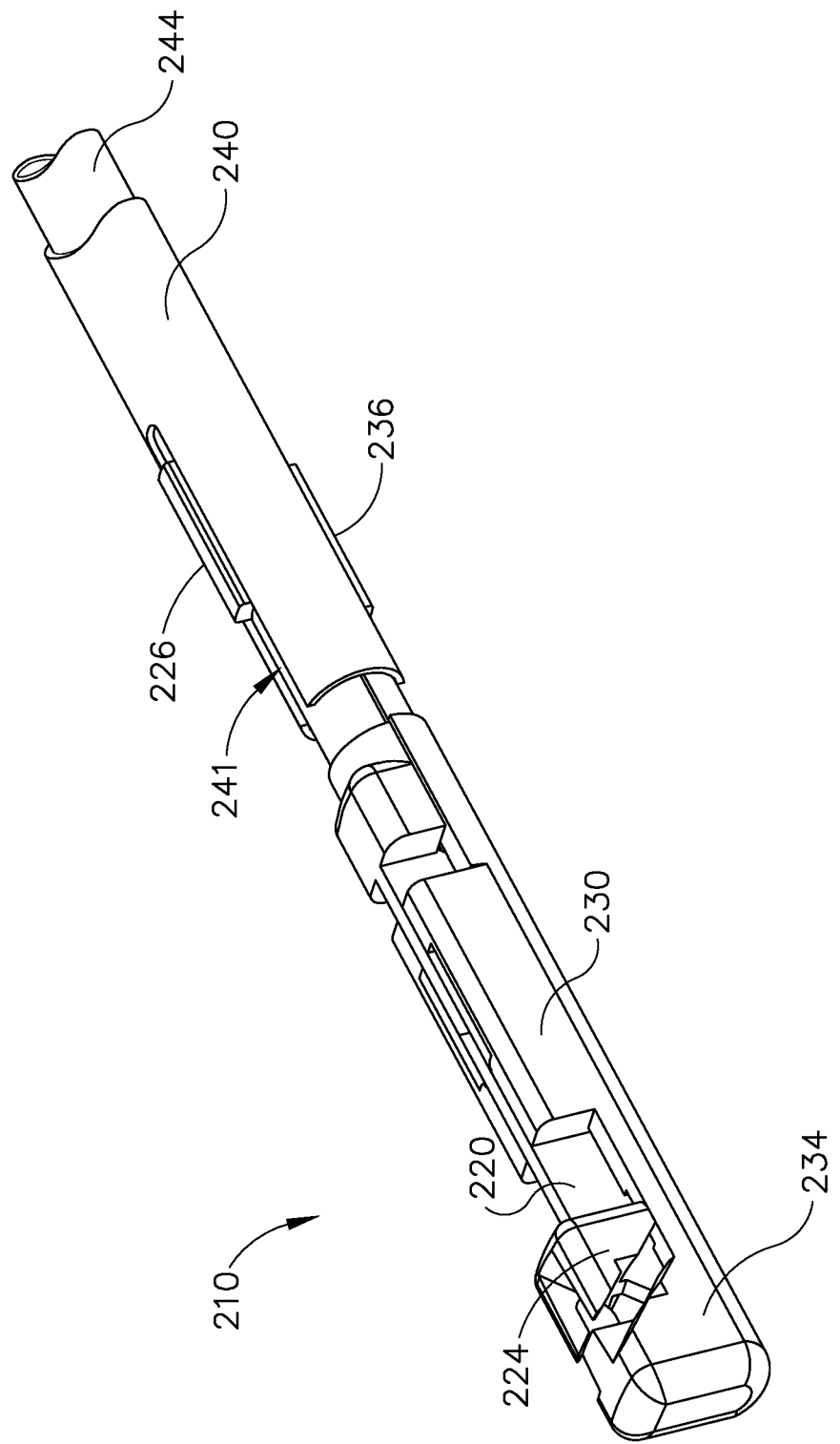
FIG. 3A depicts a first partial perspective view of a first needle grasping arm of the end effector of FIG. 2A
Figure 3B:
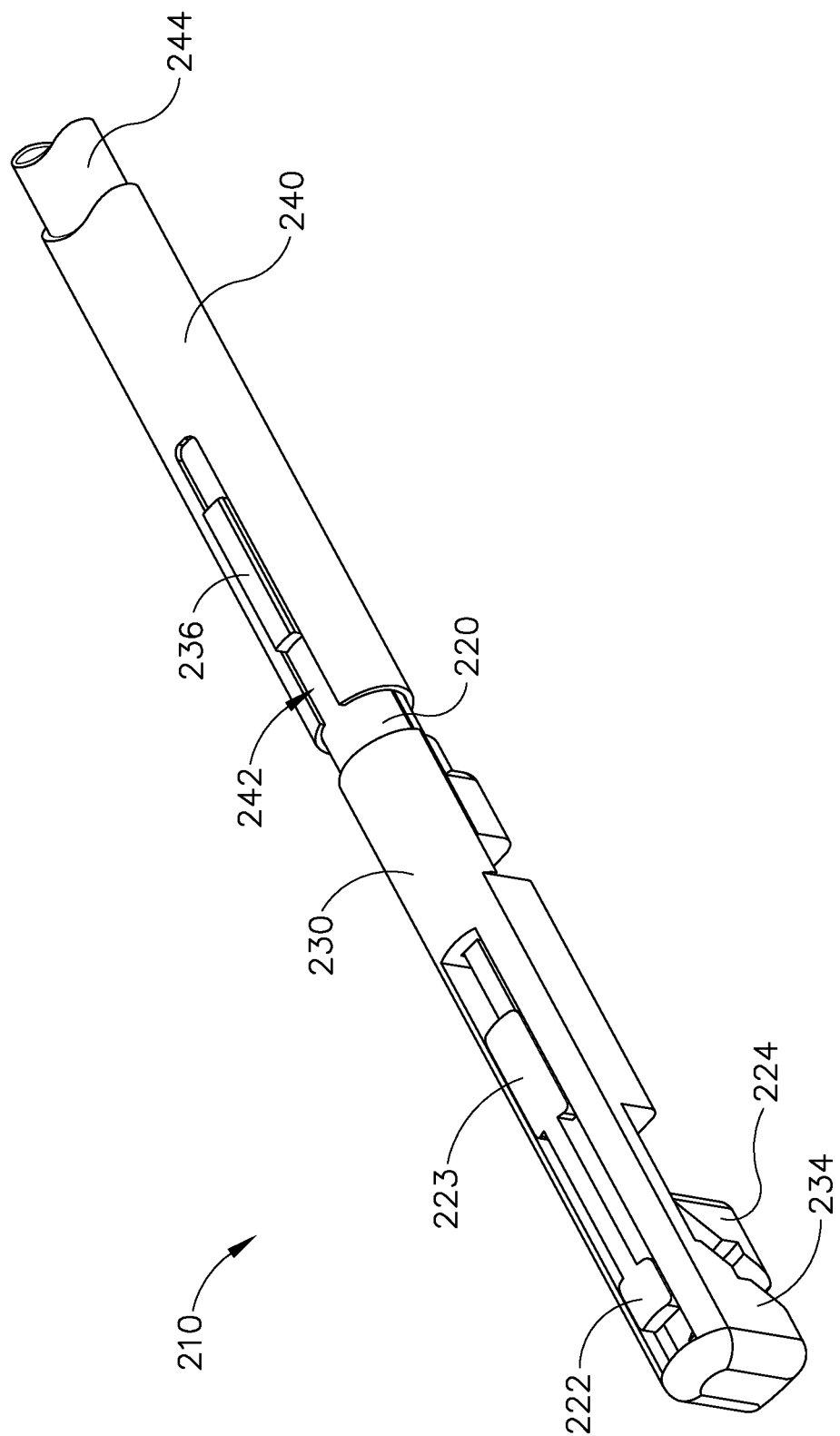
FIG. 3B depicts a second partial perspective view of the first needle grasping arm of FIG. 3A.
Figure 3C:
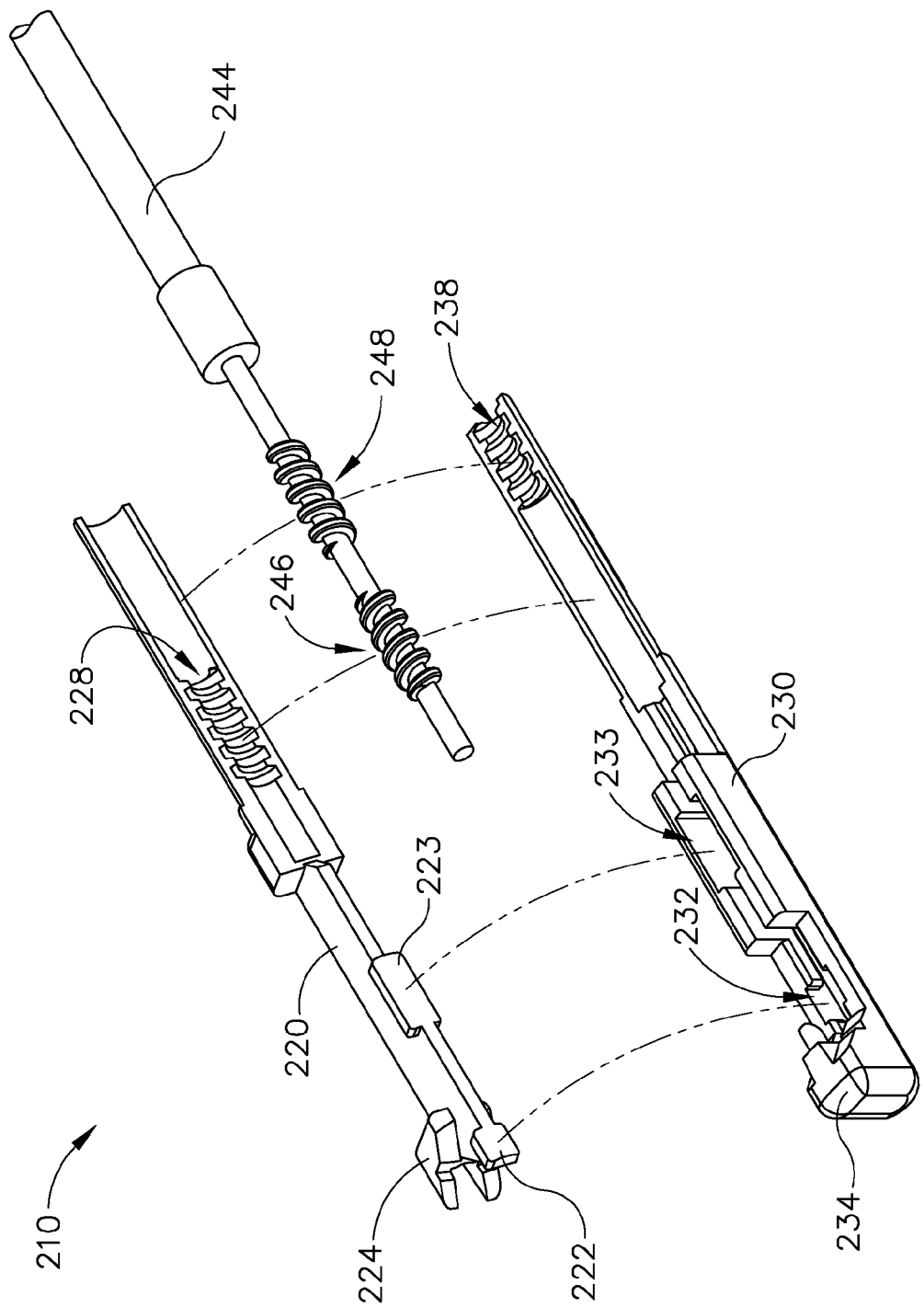
FIG. 3C depicts a partial exploded view of the first needle grasping arm of FIG. 3A.

FIGS. 3A-3C show an exploded view of a first grasping arm (210) in greater detail. First grasping arm (210) comprises a first jaw (220) and a second jaw (230). Referring to FIGS. 3A-3B, jaws (220, 230) substantially align with each other and are slidable longitudinally relative to each other. As shown in FIG. 3B, jaw (220) includes a pair of flanges (222, 223) that are received through corresponding openings (232, 233) of second jaw (230) during assembly of arm (210). Thereafter, flanges (222, 223) substantially prevent jaws (220, 230) from deflecting transversely away from each other. Jaws (220, 230) also include complementary needle grasping features (224, 234) that are configured to selectively grasp needle (50) as will be described in greater detail below. The proximal portion of jaws (220, 230) each includes a transversely extending fin (226, 236). Fins (226, 236) are slidably disposed in corresponding distal slots (241, 242) of a sheath (240) (shown in FIG. 6). Sheath (240) extends along the length of shaft (100) and is substantially fixed within shaft (100). In particular, sheath (240) does not rotate or translate relative to shaft (100) in this example. Sheath (240) thus provides a mechanical ground in the angular direction. It should therefore be understood that the relationship between fins (226, 236) and slots (241, 242) prevent first grasping arm (210) from rotating relative to shaft (100). In some other versions, however, first grasping arm (210) is rotatable relative to shaft (100) (e.g., by rotating sheath (240) within shaft (100), etc.). It should also be understood that, in the present example, the relationship between fins (226, 236) and slots (241, 242) still permits jaws (220, 230) to translate relative to sheath (240) and shaft (100).

Jaws (220, 230) of the present example are simultaneously movable in opposite directions to selectively expand or reduce an opening formed by grasping features (224, 234) to receive needle (50). To open and receive needle (50), first jaw (220) moves proximally toward shaft (100) and second jaw (230) simultaneously moves distally away from shaft (100) to enlarge the opening defined by grasping features (224, 234) to receive needle (50). To close and grip needle (50), first jaw (220) has moved distally away from shaft (100) and second jaw (230) has simultaneously moved proximally toward shaft (100) to reduce the opening defined by grasping features (224, 234) to securely grasp needle (50). In some versions, one jaw (220, 230) remains longitudinally stationary while the other jaw translates longitudinally to grasp or release needle (50) between grasping features (224, 234). However, it should be understood that in versions such as the present example where jaws (220, 230) both move simultaneously in opposite directions, such motion may further promote alignment of needle (50) within grasping features (224, 234) as compared to versions where one jaw (220, 230) always stays longitudinally fixed relative to shaft (100). In other words, having both grasping features (224, 234) always spaced equidistantly away from the intended path of needle (50) (regardless of whether jaws (220, 230) are open or closed) may better accommodate incidental deflections of needle (50) away from that intended path in either direction during use of instrument (10). Arm (210) may thus be particularly suited to accommodate instances where needle (50) has deviated away from the expected perpendicular plane of motion as described above.

As shown in FIG. 3C, to provide the simultaneous opposing motion of jaws (220, 230), a first drive shaft (244) includes a first threaded section (246) and a second threaded section (248). First drive shaft (244) is coaxially positioned within sheath (240), shown in FIG. 6, and is rotatable within sheath (240). First drive shaft (244) of the present example is rotatably driven from within handle portion (400), as will be discussed in greater detail below. The threading of first threaded section (246) is oriented opposite to the threading of second threaded section (248), such that threaded sections (246, 248) have opposite pitches. The proximal portions of jaws (220, 230) together encompass the distal portion of first drive shaft (244). In particular, the proximal portion of first jaw (220) includes threading (228) that meshes with first threaded section (246); while the proximal portion of second jaw (230) includes threading (238) that meshes with second threaded section (248). It should therefore be understood that threading (228) has a pitch that is opposite to the pitch of threading (238). It should also be understood that, due to the relationships and orientations of threaded sections (246, 248) and threading (228, 238), first drive shaft (244) will cause jaws (220, 230) to simultaneously translate away from each other when first drive shaft (244) is rotated in one direction; while first drive shaft (244) will cause jaws (220, 230) to simultaneously translate toward each other when first drive shaft (244) is rotated in the other direction.

It should be understood that the opposing-thread configuration described above may require relatively low torsional force to rotate first drive shaft (244) to drive jaws (220, 230) toward and away from each other. It should also be understood that the opposing-thread configuration described above may provide a relatively high holding force. For instance, when needle grasping features (224, 234) are driven toward each other to secure needle (50) and needle (50) is off-plane for whatever reason (e.g., incidentally oriented slightly obliquely relative to longitudinal axis (130) of shaft (100), etc.), the needle holding forces at grasping features (224, 234) may be self-reinforcing due to opposing forces provided through the opposing thread configuration described above, providing a mechanical advantage to urge needle (50) back into the desired planar orientation, even if tissue or some other structure is resisting such movement of needle (50) into the desired planar orientation. Similarly, the opposing thread configuration described above may provide friction that acts as an anti-backup feature, substantially resisting inadvertent separation of grasping features (224, 234), thereby providing a very secure hold of needle (50). Other suitable components that may be used to provide opposing motion of grasping features (224, 234) (e.g., a pinion with opposing racks, etc.) will be apparent to those of ordinary skill in the art in view of the teachings herein.

It should also be understood that, while first drive shaft (244) rotates about an axis that is parallel to longitudinal axis (130) of shaft (100), alternative drive systems that include a rotary member may provide rotation of such a rotary member about an axis that is not parallel to longitudinal axis (130) of shaft (100). For instance, a pinion based drive system may provide rotation of a drive pinion about an axis that is perpendicular to longitudinal axis (130) of shaft (100). Other suitable ways in which jaws (220, 230) may be actuated will be apparent to those of ordinary skill in the art in view of the teachings herein. First grasping arm (210) may be further constructed in accordance with the teachings of U.S. patent application Ser. No. 13/295,203, entitled "Laparoscopic Suturing Instrument with Dual-Action Needle Graspers," filed Nov. 11, 2011, now U.S. Pat. No. 8,702,732, issued Apr. 22, 2014 and/or U.S. patent application Ser. No. 13/295,210, entitled "Laparoscopic Suturing Instrument with Perpendicular Eccentric Needle Motion," filed Nov. 11, 2011, now U.S. Pat. No. 8,906,043, issued Dec. 9, 2014, the disclosures of which are incorporated by reference herein.

B. Exemplary Second Grasping Arm

Figure 4A:
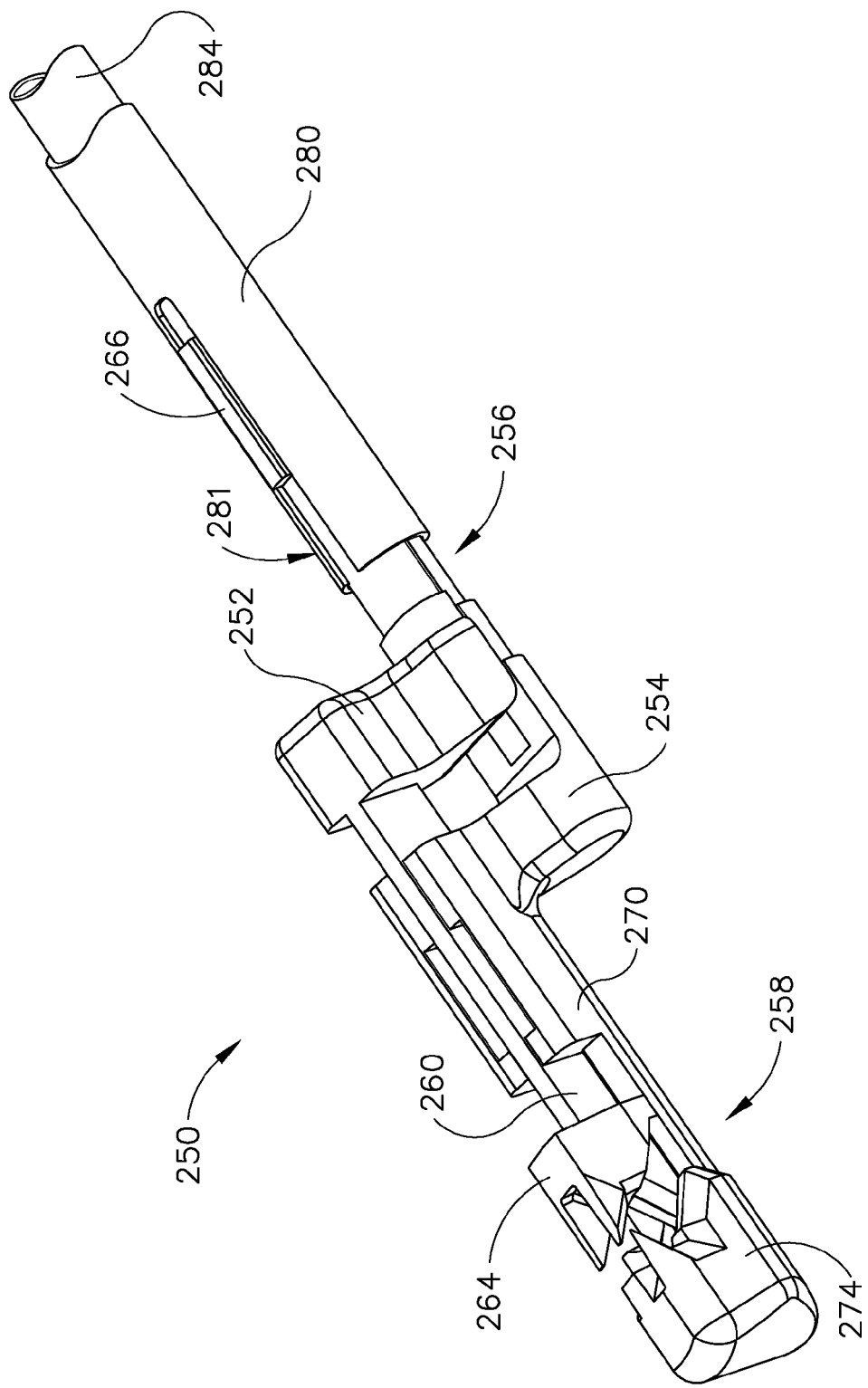
FIG. 4A depicts a first partial perspective view of a second needle grasping arm of the end effector of FIG. 2A
Figure 4B:
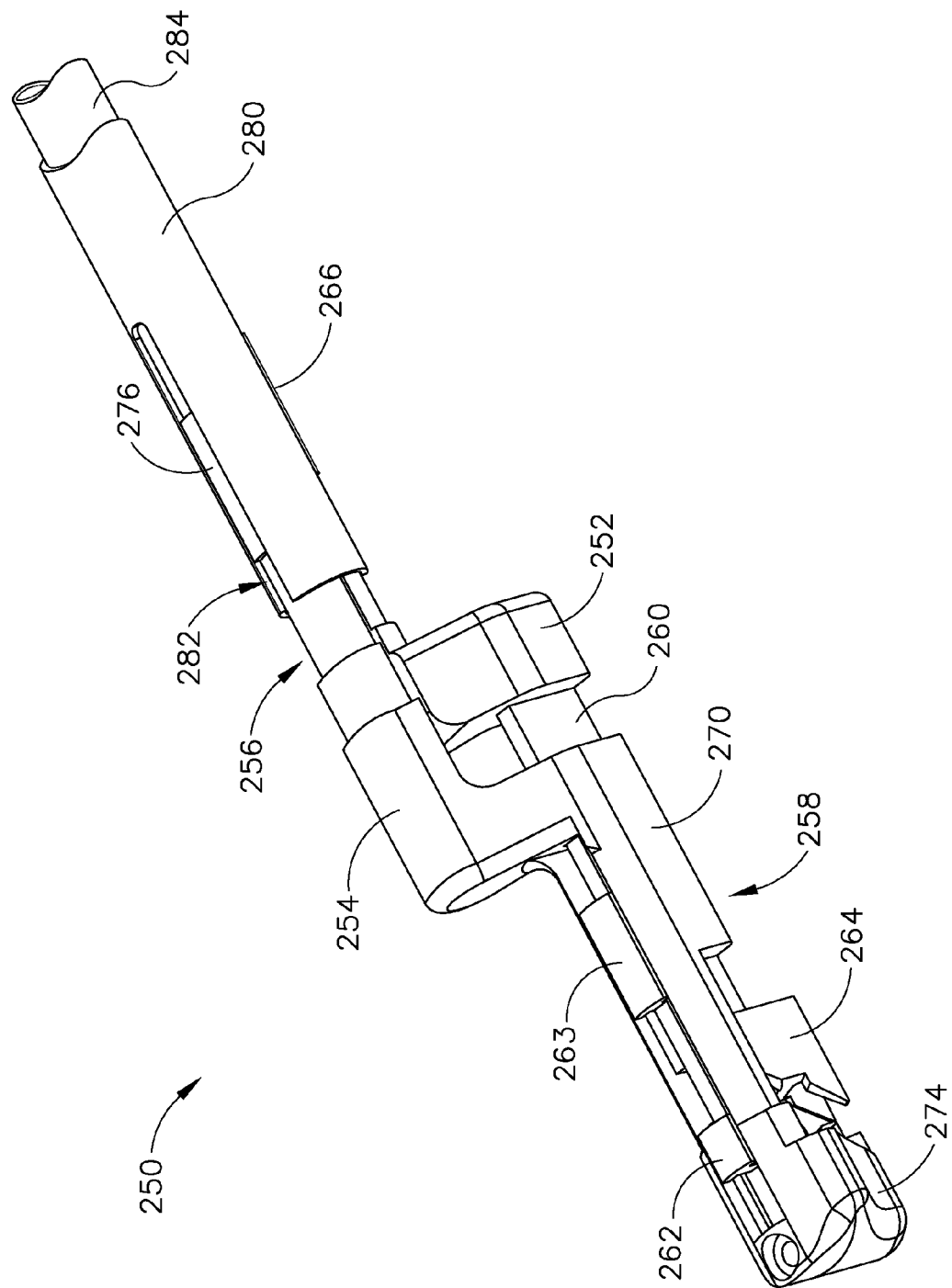
FIG. 4B depicts a second partial perspective view of the second needle grasping arm of FIG. 4A.
Figure 4C:
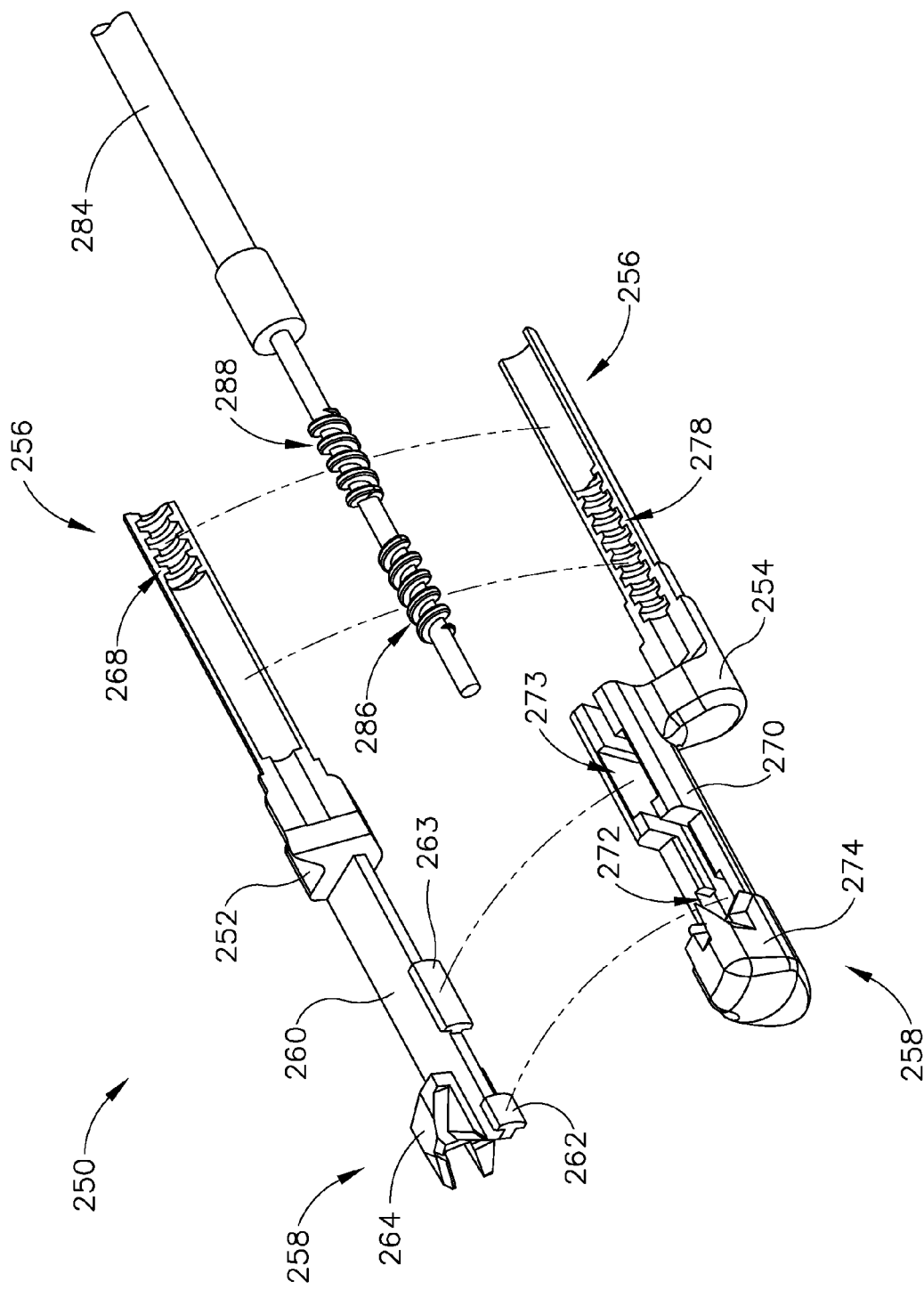
FIG. 4C depicts a partial exploded view of the second needle grasping arm of FIG. 4A.

FIGS. 4A-4C show second grasping arm (250) in greater detail having a first jaw (260) and a second jaw (270). Referring initially to FIGS. 4A-4B, jaws (260, 270) substantially align with each other and are slidable longitudinally relative to each other. As shown in FIG. 4B, first jaw (260) includes a pair of flanges (262, 263) that are received through corresponding openings (272, 273) of second jaw (270) during assembly of arm (250). Thereafter, flanges (262, 263) prevent jaws (260, 270) from deflecting transversely away from each other. Jaws (260, 270) also include complementary needle grasping features (264, 274) that are configured to selectively grasp needle (50) as will be described in greater detail below. The proximal portion of each jaw (260) includes a transversely extending fin (266, 276). Fins (266, 276) are slidably disposed in corresponding distal slots (281, 282) of a sheath (280), shown in FIG. 6. Each jaw (260, 270) of second grasping arm (250) includes a dogleg section (252, 254). Each dogleg section (252, 254) forms a pair of right angles between a proximal portion (256) of grasping arm (250) and a distal portion (258) of grasping arm (250). The configuration of dogleg sections (252, 254) provides distal portion (258) in a parallel yet offset position relative to proximal portion (256). Thus, when grasping arm (250) is rotated about a longitudinal axis (140) extending along the length of the proximal portion (256) of grasping arm (250), the distal portion (258) of grasping arm (250) rotates in an orbital motion about that longitudinal axis (140). Such motion will be described in greater detail below.

Figure 6:
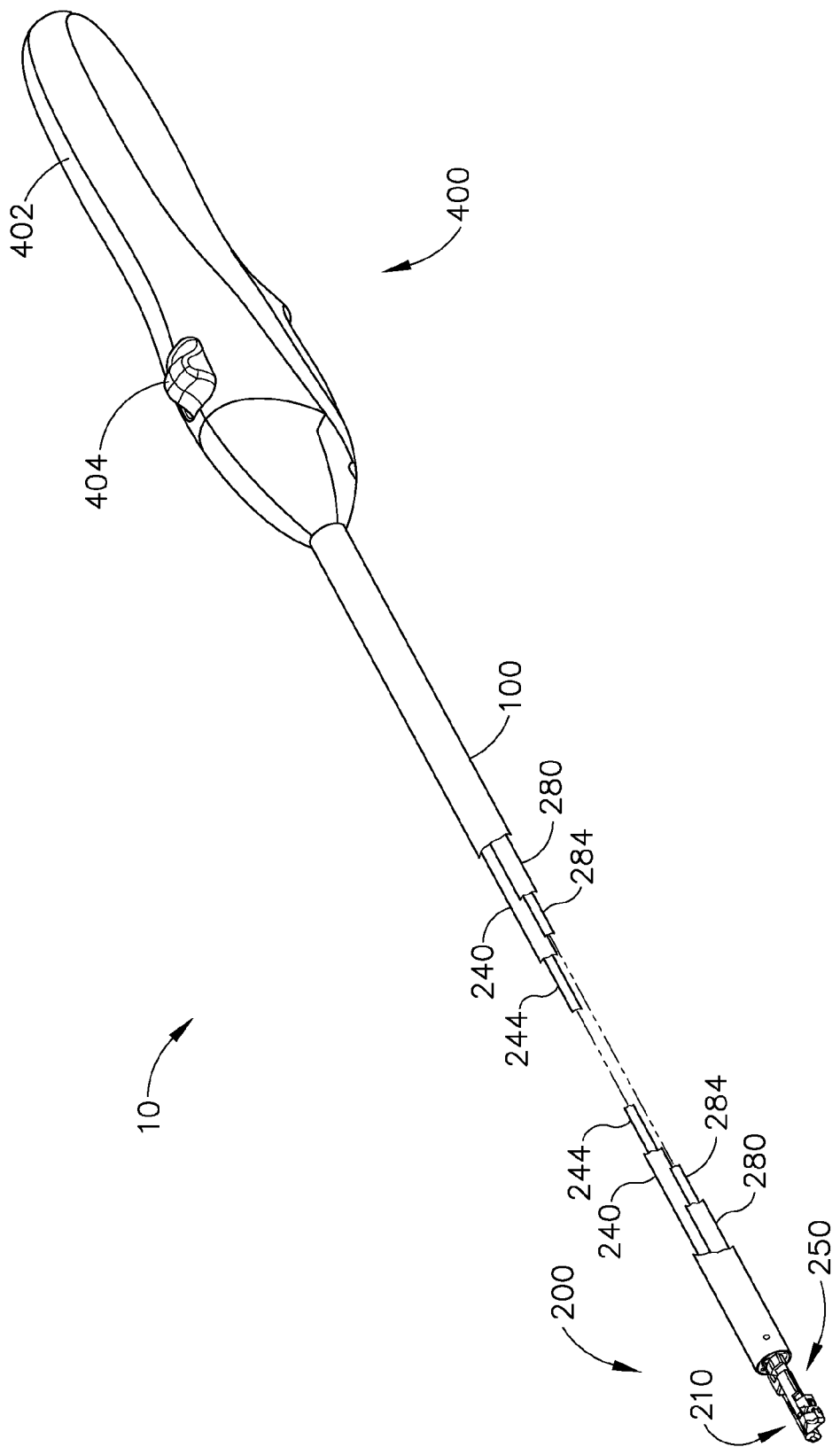
FIG. 6 depicts a perspective view of the laparoscopic suturing instrument of FIG. 1 with a portion of an outer shaft cut away to show the interior shafts.

Sheath (280), shown in FIG. 6, extends along the length of shaft (100) and is partially fixed within shaft (100). In particular, sheath (280) does not translate relative to shaft (100) in this example, though sheath (280) is rotatable relative to shaft (100). For instance, sheath (280) may be selectively rotated in either direction by a motor, trigger, actuator, and/or any other element as will be described in greater detail below. It should therefore be understood that rotation of sheath (280) relative to shaft (100) will provide rotation of second grasping arm (250) relative to shaft (100), due to the relationship between fins (266, 276) and slots (281, 282). As noted above, when second grasping arm (250) is rotated by sheath (280), the distal portion (258) of grasping arm (250) rotates in an orbital motion about longitudinal axis (140) that is defined by both sheath (280) and the proximal portion (256) of grasping arm (250). In some other versions, second grasping arm (250) is non-rotatable relative to shaft (100). It should also be understood that, in the present example, the relationship between fins (266, 276) and slots (281, 282) permits jaws (260, 270) to translate relative to sheath (280) and shaft (100).

In the present example, jaws (260, 270) are simultaneously movable in opposite directions to selectively expand or reduce an opening formed by grasping features (264, 274) to receive needle (50). To open and receive needle (50), first jaw (260) moves proximally toward shaft (100) and second jaw (270) simultaneously moves distally away from shaft (100) to enlarge the opening defined by grasping features (264, 274) to receive needle (50). To close and grip needle (50), first jaw (260) moves distally away from shaft (100) and second jaw (270) simultaneously moves proximally toward shaft (100) to reduce the opening defined by grasping features (264, 274) to securely grasp needle (50). In some versions, one jaw (260, 270) remains longitudinally stationary while the other jaw translates longitudinally to grasp or release needle (50) between grasping features (264, 274). However, it should be understood that in versions such as the present example where jaws (260, 270) both move simultaneously in opposite directions, such motion may further promote alignment of needle (50) within grasping features (264, 274) as compared to versions where one jaw (260, 270) always stays longitudinally fixed relative to shaft (100). In other words, having both grasping features (264, 274) always spaced equidistantly away from the intended path of needle (50) (regardless of whether jaws (260, 270) are open or closed) may better accommodate incidental deflections of needle (50) away from that intended path in either direction during use of instrument (10). Arm (250) may thus be particularly suited to accommodate instances where needle (50) has deviated away from the expected perpendicular plane of motion as described above.

As shown in FIG. 4C, to provide the simultaneous opposing motion of jaws (260, 270), a second drive shaft (284) that includes a first threaded section (286) and a second threaded section (288). Second drive shaft (284) is coaxially positioned within sheath (280) and is rotatable within sheath (280). Second drive shaft (284) of the present example is rotatably driven from within handle portion (400), as will be discussed in greater detail below. The threading of first threaded section (286) is oriented opposite to the threading of second threaded section (288), such that threaded sections (286, 288) have opposite pitches. The proximal portions of jaws (260, 270) together encompass the distal portion of drive shaft (284). In particular, the proximal portion of first jaw (260) includes threading (268) that meshes with first threaded section (286); while the proximal portion of second jaw (270) includes threading (278) that meshes with second threaded section (288). It should therefore be understood that threading (268) has a pitch that is opposite to the pitch of threading (278). It should also be understood that, due to the relationships and orientations of threaded sections (286, 288) and threading (268, 278), second drive shaft (284) will cause jaws (260, 270) to simultaneously translate away from each other when second drive shaft (284) is rotated in one direction; while second drive shaft (284) will cause jaws (260, 270) to simultaneously translate toward each other when second drive shaft (284) is rotated in the other direction.

In some settings, the rotational position of sheath (280) is fixed relative to shaft (100) when second drive shaft (284) is rotated relative to shaft (100). Thus, sheath (280) substantially holds the rotational position of jaws (260, 270) when second drive shaft (284) is rotated. In some other settings, sheath (280) and second drive shaft (284) are rotated simultaneously relative to shaft (100). In some such instances, sheath (280) and second drive shaft (284) are rotated in the same direction and at the same speed, such that second drive shaft (284) and jaws (260, 270) are rotated in the same direction and at the same speed. Thus, the longitudinal positioning of jaws (260, 270) remains fixed during such rotation. As another merely illustrative variation, sheath (280) and second drive shaft (284) may be rotated simultaneously relative to shaft (100), but at different speeds and/or in different directions. Such a scheme provides a rotation differential between jaws (260, 270) and second drive shaft (284), such that jaws (260, 270) may open or close while second grasping arm (250) is simultaneously being rotated relative to shaft (100).

It should be understood that the opposing thread configuration described above may require relatively low torsional force to rotate second drive shaft (284) to drive jaws (260, 270) toward and away from each other. It should also be understood that the opposing thread configuration described above may provide a relatively high holding force. For instance, when needle grasping features (264, 274) are driven toward each other to secure needle (50) and needle (50) is off-plane for whatever reason (e.g., incidentally oriented slightly obliquely relative to longitudinal axis (130) of shaft (100), etc.), the needle holding forces at grasping features (264, 274) may be self-reinforcing due to opposing forces provided through the opposing thread configuration described above, providing a mechanical advantage to urge needle (50) back into the desired planar orientation, even if tissue or some other structure is resisting such movement of needle (50) into the desired planar orientation. Similarly, the opposing thread configuration described above may provide friction that acts as an anti-backup feature, substantially resisting inadvertent separation of grasping features (264, 274), thereby providing a very secure hold of needle (50). Other suitable components that may be used to provide opposing motion of grasping features (264, 274) (e.g., a pinion with opposing racks, etc.) will be apparent to those of ordinary skill in the art in view of the teachings herein.

It should also be understood that, while second drive shaft (284) rotates about a longitudinal axis (140) that is parallel to longitudinal axis (130) of shaft (100), alternative drive systems that include a rotary member may provide rotation of such a rotary member about an axis that is not parallel to longitudinal axis (130) of shaft (100). For instance, a pinion based drive system may provide rotation of a drive pinion about an axis that is perpendicular to longitudinal axis (130) of shaft (100). Other suitable ways in which one or more components of second grasping arm (250) may be actuated will be apparent to those of ordinary skill in the art in view of the teachings herein. Second grasping arm (250) may be further constructed in accordance with the teachings of U.S. patent application Ser. No. 13/295,203, entitled "Laparoscopic Suturing Instrument with Dual-Action Needle Graspers," filed Nov. 11, 2011, now U.S. Pat. No. 8,702,732, issued Apr. 22, 2014 and/or U.S. patent application Ser. No. 13/295, 210, entitled "Laparoscopic Suturing Instrument with Perpendicular Eccentric Needle Motion," filed Nov. 11, 2011, now U.S. Pat. No. 8,906,043, issued Dec. 9, 2014, the disclosures of which are incorporated by reference herein.

III. Exemplary Operation of End Effector

Figure 5A:
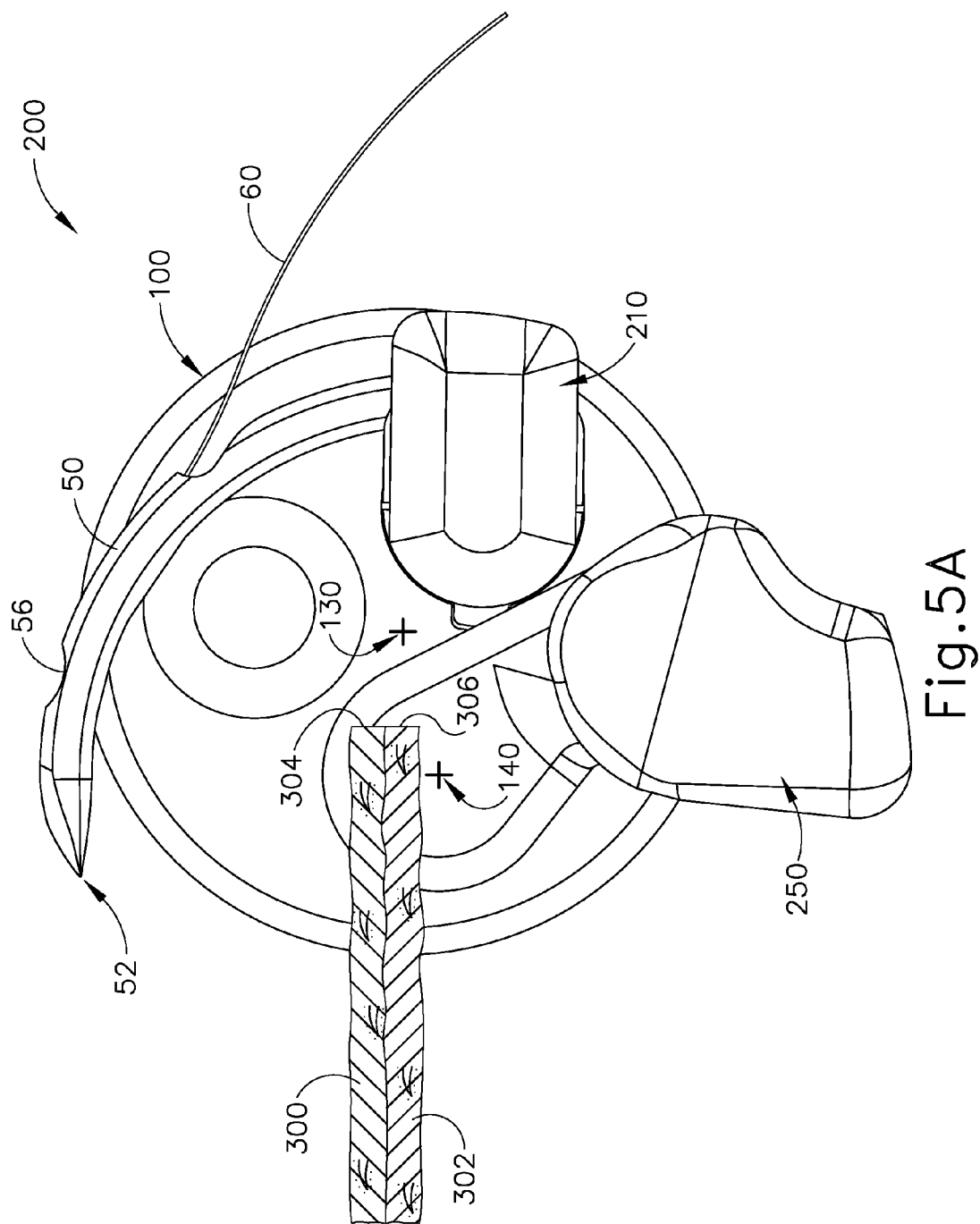
FIG. 5A depicts an end elevation view of the end effector and needle of FIG. 2A, during an exemplary first stage of operation.

FIGS. 5A-5H depict a merely exemplary method for using surgical instrument (10). In particular, FIG. 5A shows end effector (200) positioned adjacent to apposed layers (300, 302) of tissue. End effector (200) is positioned such that longitudinal axis (130) of shaft (100) is substantially parallel to the outer edges (304, 306) of tissue layers (300, 302). In this sense, "substantially parallel" simply means that end effector (200) is oriented in relation to tissue layers (300, 302) in a manner sufficient to enable needle (50) to be passed through tissue layers (300, 302). It should therefore be understood that longitudinal axis (130) need not necessarily be truly parallel with outer edges (304, 306), though longitudinal axis (130) may in fact be truly parallel with outer edges (304, 306) in some instances. It should also be understood that instrument (10) and needle (50) may be used to secure tissue together in an edge-to-edge arrangement rather than securing apposed layers (300, 302) as shown. Other suitable settings in which instrument (10) and needle (50) may be used will be apparent to those of ordinary skill in the art in view of the teachings herein. It should also be understood that the curved configuration of needle (50) may provide a more intuitive operation for the surgeon than a straight needle would, such as by providing better predictability for where sharp tip (52) will come through tissue.

Figure 5B:
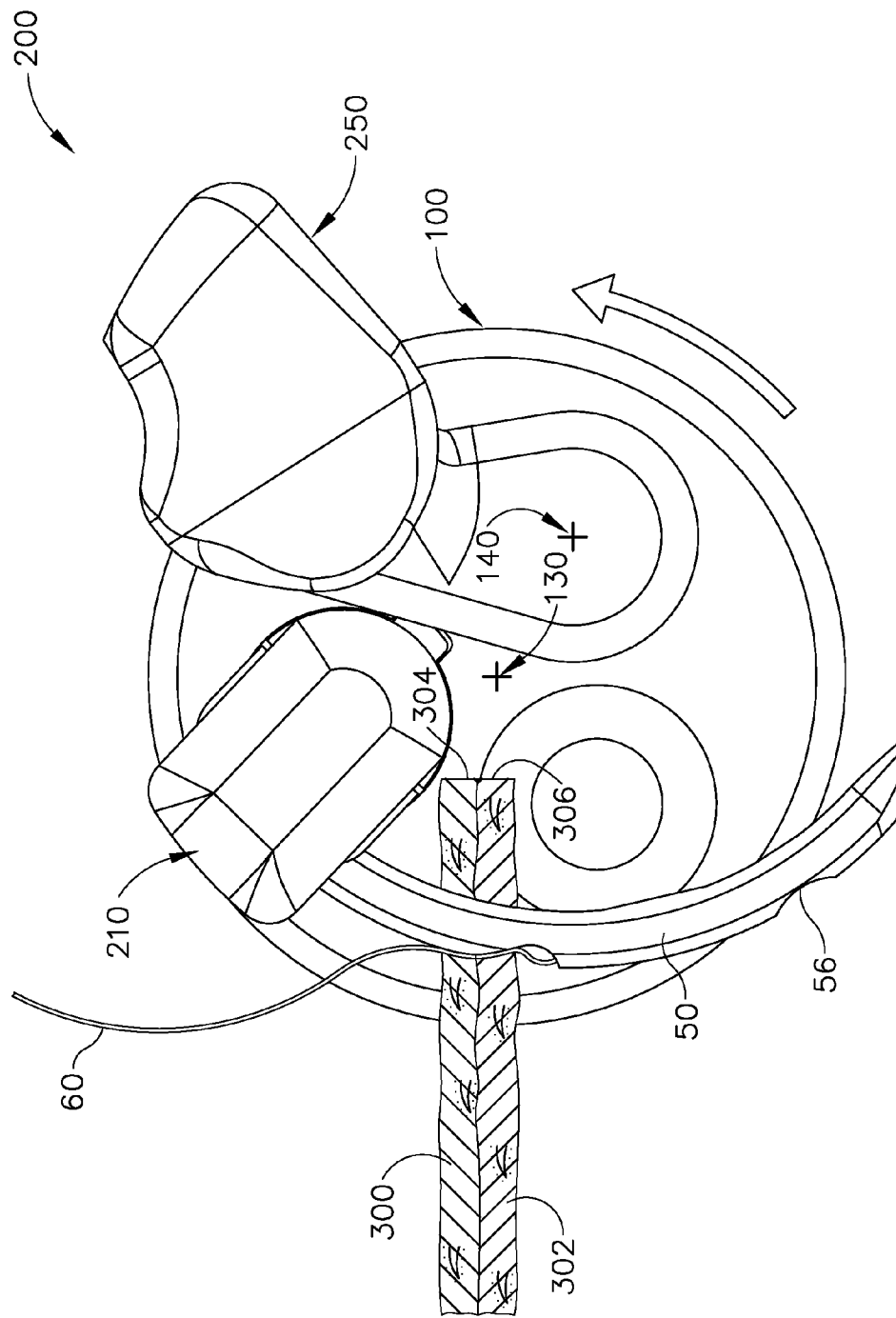
FIG. 5B depicts an end elevation view of the end effector and needle of FIG. 2A, during an exemplary second stage of operation.

As shown in FIG. 5A, first grasping arm (210) is securely holding needle (50), with sharp tip (52) exposed. In particular, grasping portions (224, 234) of jaws (220, 230) hold needle (50) at grasping region (56). Needle (50) is oriented along a plane that is substantially transverse to longitudinal axis (130). Once end effector (200) has been positioned as shown in FIG. 5A, the entire instrument (10) is rotated about longitudinal axis (130) to drive sharp tip (52) through tissue layers (300, 302), as shown in FIG. 5B. In the example shown, the rotational direction for instrument (10) is counterclockwise viewed from the distal end toward the proximal end, though it should be understood that instrument (10) may be rotated clockwise instead (e.g., depending on the orientation of sharp tip (52)). During the transition from the position of FIG. 5A to the position of FIG. 5B, the rotational position of grasping arms (210, 250) relative to shaft (100) remains fixed, such that grasping arms (210, 250) rotate unitarily with shaft (100) about longitudinal axis (130). The longitudinal position of jaws (220, 230, 260, 270) also remains fixed during this transition. As can also be seen in FIG. 5B, needle (50) has started to pull suture (60) through tissue layers (300, 302) at this stage. It should be understood that, in the stages shown in FIGS. 5A-5B, grasping arms (210, 250) and needle (50) are in the same rotational positions relative to shaft (100) as shown in FIG. 2A. It should also be noted that the configuration of end effector (200) and needle (50) may provide the surgeon with enhanced visibility of sharp tip (52) exiting tissue layers (300, 302) during the transition from FIG. 5A to FIG. 5B, particularly with second grasping arm (250) being rotated out of the way at this stage.

After needle (50) has been driven at least partially through tissue layers (300, 302), second grasping arm (250) is rotated about its own axis (140) toward needle (50) as shown in FIG. 5C. Such rotation is provided by rotating sheath (280) relative to shaft (100). The rotational position of shaft (100) relative to longitudinal axis (130) remains fixed during the transition from the configuration shown in FIG. 5B to the configuration shown in FIG. 5C. It should be understood that, in the stage shown in FIG. 5C, grasping arms (210, 250) and needle (50) are in the same rotational positions relative to shaft (100) as shown in FIG. 2B.

In some versions, jaws (260, 270) are already opened by the time second grasping arm (250) starts rotating from the position shown in FIG. 5B to the position shown in FIG. 5C. In other versions, jaws (260, 270) are actively opened during the transition from the position shown in FIG. 5B to the position shown in FIG. 5C, such that jaws (260, 270) are fully open by the time second grasping arm (250) reaches the position shown in FIG. 5C. Once second grasping arm (250) reaches the position shown in FIG. 5C, jaws (260, 270) of second grasping arm (250) close to grasp needle (50) at grasping region (58) with grasping features (264, 274). In addition, jaws (220, 230) of first grasping arm (210) open to release needle (50) from grasping features (224, 234) at grasping region (56). In some versions, jaws (260, 270) of second grasping arm (250) close to grasp needle (50) at substantially the same time as jaws (220, 230) of first grasping needle (210) open to release needle (50). In some other versions, jaws (220, 230) of first grasping arm (210) do not open to release needle (50) until jaws (260, 270) of second grasping arm (250) have closed to grasp needle (50). Various suitable timing schemes and ways in which such schemes may be carried out will be apparent to those of ordinary skill in the art in view of the teachings herein.

Figure 5D:
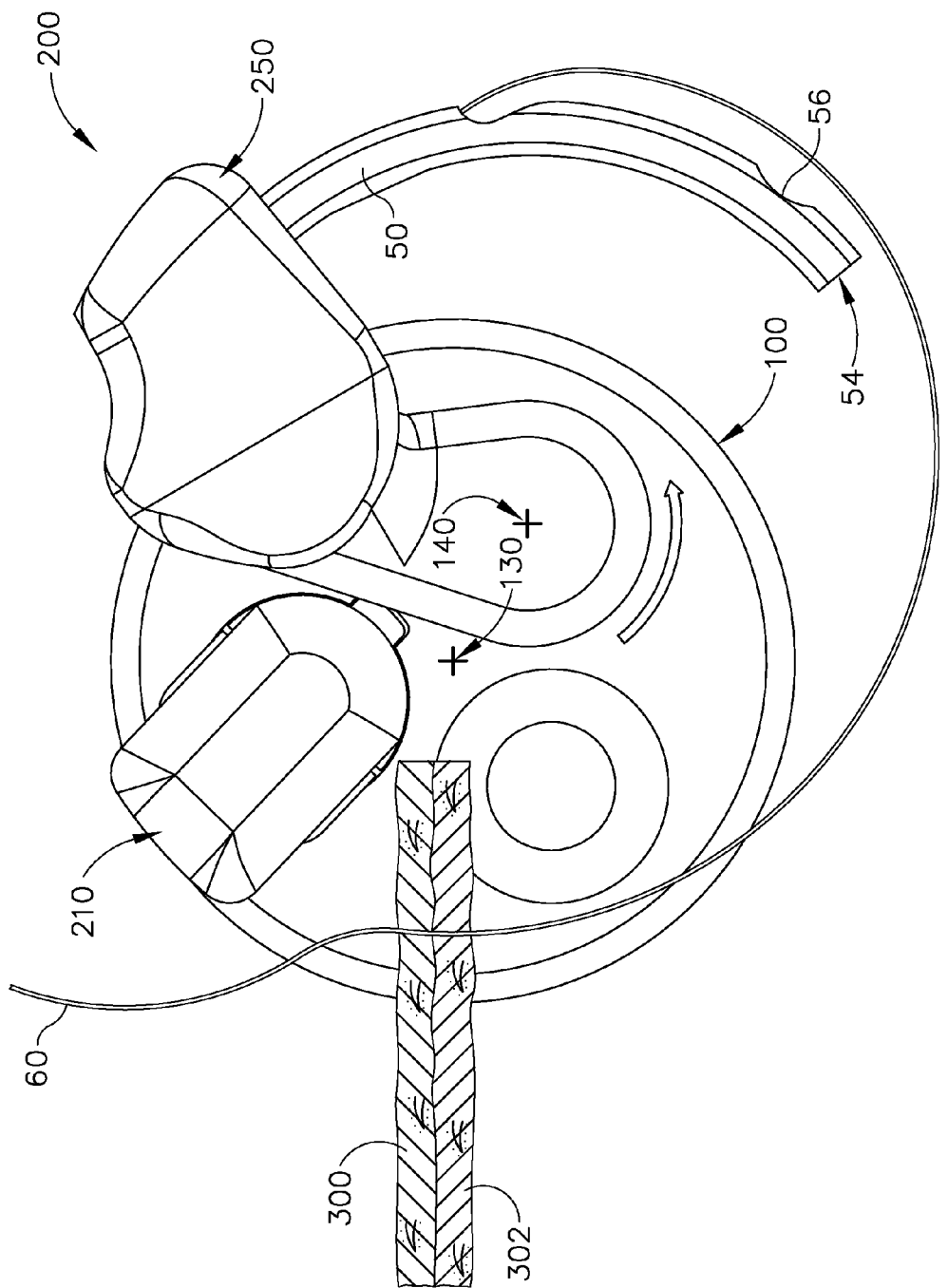
FIG. 5D depicts an end elevation view of the end effector and needle of FIG. 2A, during an exemplary fourth stage of operation.

Once control of needle (50) has been effectively passed from first grasping arm (210) to second grasping arm (250), second grasping arm (250) is rotated about longitudinal axis (140) to the position shown in FIG. 5D. Such rotation is provided by once again rotating sheath (280) relative to shaft (100), as will be described in greater detail below. The rotational position of shaft (100) relative to longitudinal axis (130) continues to be fixed during the transition from the configuration shown in FIG. 5C to the configuration shown in FIG. 5D. It should be understood that, in the stage shown in FIG. 5D, grasping arms (210, 250) and needle (50) are in the same rotational positions relative to shaft (100) as shown in FIG. 2C. As can also be seen in FIG. 5D, grasping arm (250) pulls suture (60) through tissue layers (300, 302) during the transition from FIG. 5C to FIG. 5D.

Figure 5E:
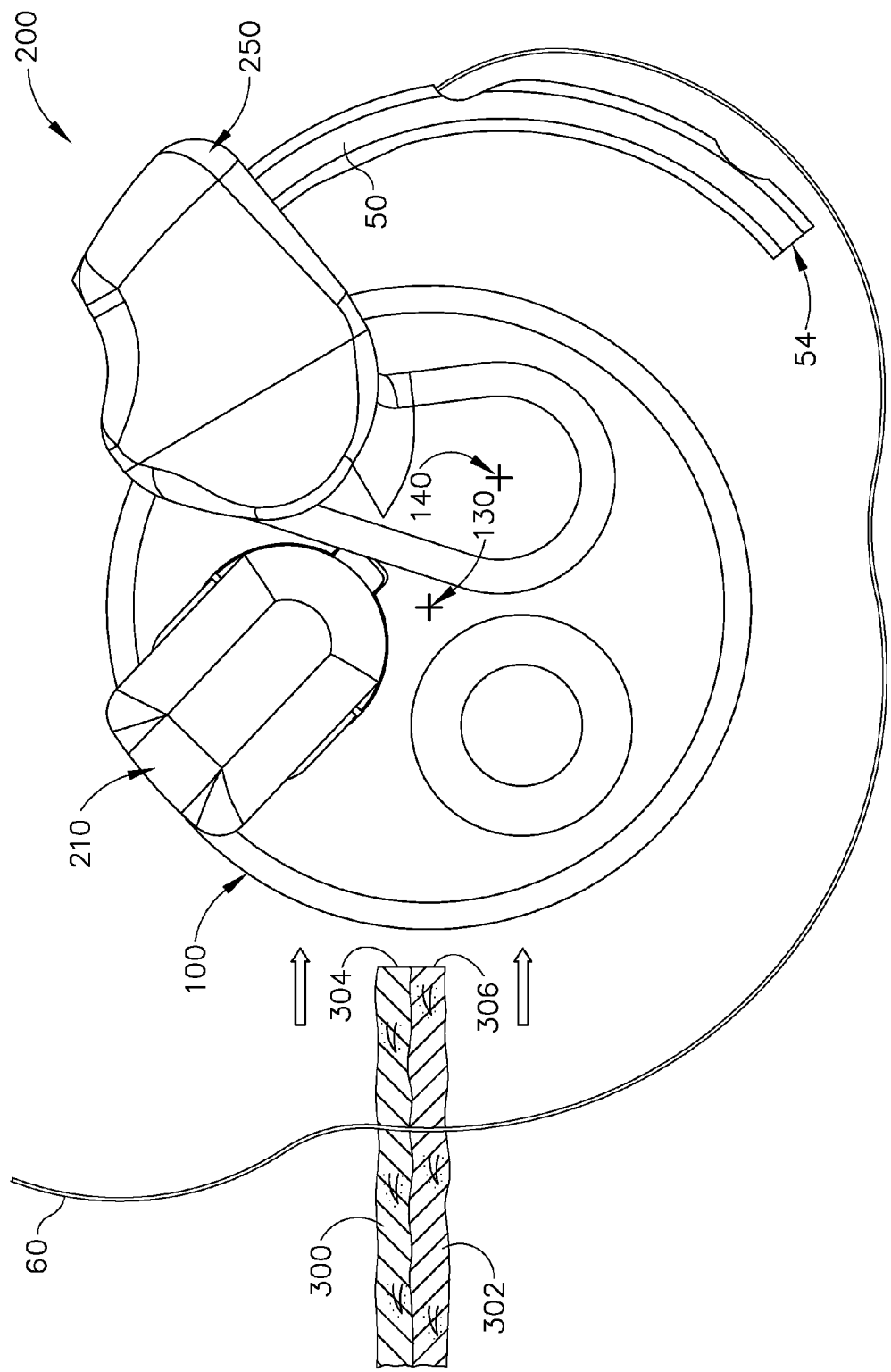
FIG. 5E depicts an end elevation view of the end effector and needle of FIG. 2A, during an exemplary fifth stage of operation.

After reaching the configuration shown in FIG. 5D, the surgeon pulls the entire end effector (200) away from tissue layers (300, 302), along a path that is substantially transverse to longitudinal axis (130), as shown in FIG. 5E. It should be understood that this path may be oblique relative to longitudinal axis (130) and/or edges (304, 306), helical, and/or of any other suitable orientation. It should also be understood that neither arm (210, 250) is rotated relative to shaft (100) in the present example during the transition from the position shown in FIG. 5D to the position shown in FIG. 5E. Thus, in the stage shown in FIG. 5E, grasping arms (210, 250) and needle (50) are still in the same rotational positions relative to shaft (100) as shown in FIG. 2C. In moving instrument (10) away from tissue layers (300, 302) during the transition to the position shown in FIG. 5E, suture (60) is pulled further through tissue layers (300, 302).

Figure 5F:
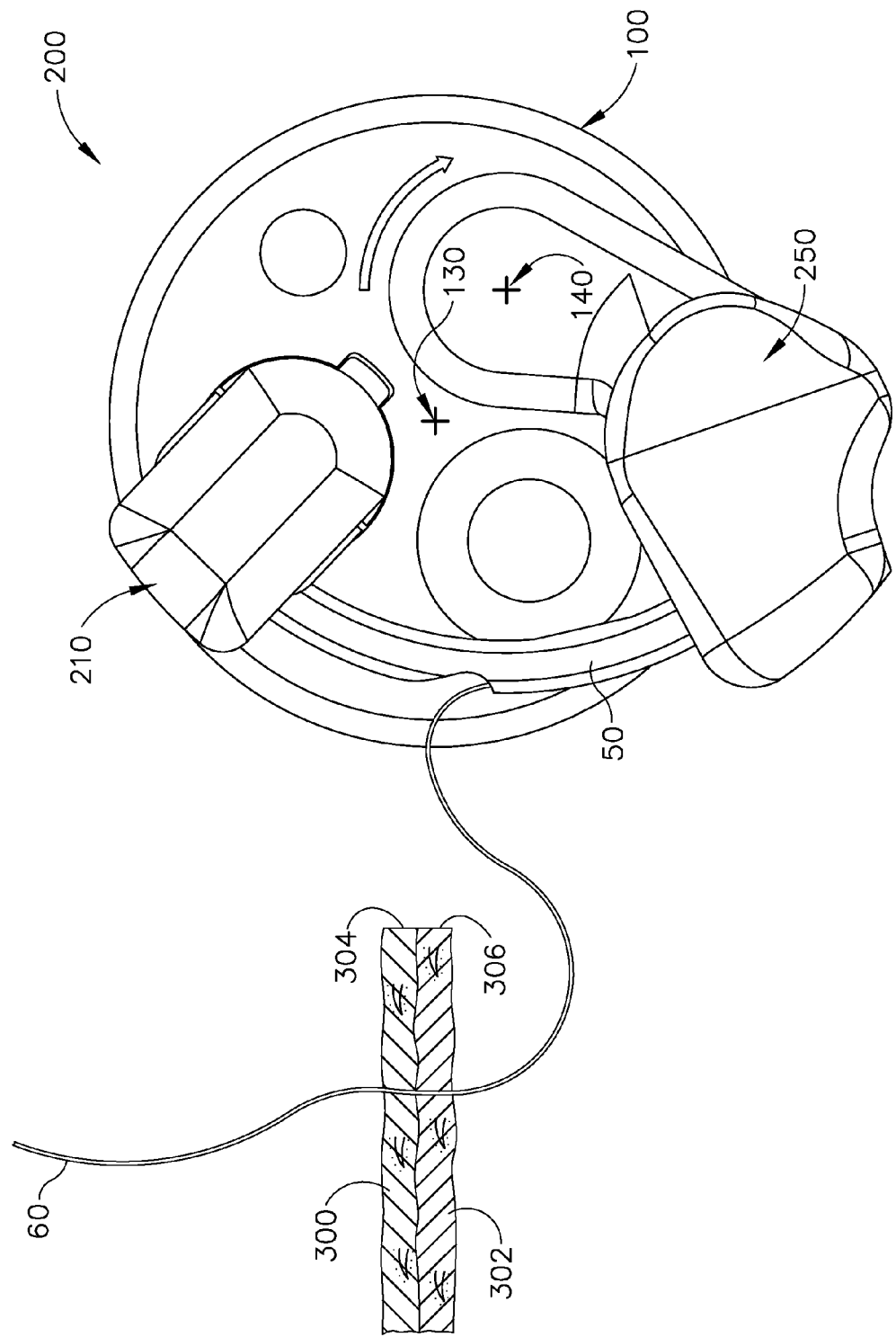
FIG. 5F depicts an end elevation view of the end effector and needle of FIG. 2A, during an exemplary sixth stage of operation.

With end effector (200) positioned sufficiently away from tissue layers (300, 302), second grasping arm (250) is rotated about longitudinal axis (140) to the position shown in FIG. 5F. The rotational position of shaft (100) relative to longitudinal axis (130) remains fixed during the transition from the configuration shown in FIG. 5E to the configuration shown in FIG. 5F. It should be understood that, in the stage shown in FIG. 5F, grasping arms (210, 250) and needle (50) are in the same rotational positions relative to shaft (100) as shown in FIG. 2B. End effector (200) is positioned far enough away from tissue layers (300, 302) during the transition from the position shown in FIG. 5E to the position shown in FIG. 5F such that blunt end (54) of needle (50) does not touch tissue layers (300, 302). The rotation of second grasping arm (250) to the position shown in FIG. 5F places grasping region (58) of needle (50) back between grasping portions (224, 234) of jaws (220, 230) of first grasping arm (210).

In some versions, jaws (220, 230) of first grasping arm (210) are already opened by the time second grasping arm (250) starts rotating from the position shown in FIG. 5E to the position shown in FIG. 5F. In other versions, jaws (220, 230) of first grasping arm (210) are actively opened during the transition from the position shown in FIG. 5E to the position shown in FIG. 5F, such that jaws (220, 230) are fully open by the time second grasping arm (250) reaches the position shown in FIG. 5F. Once second grasping arm (250) reaches the position shown in FIG. 5F, jaws (220, 230) of first grasping arm (210) close to grasp needle (50) at grasping region (56) with grasping portions (224, 234). In addition, jaws (260, 270) of second grasping arm (250) open to release needle (50) from grasping portions (264, 274) at grasping region (58). In some versions, jaws (220, 230) of first grasping arm (210) close to grasp needle (50) at substantially the same time as jaws (260, 270) of second grasping arm (250) open to release needle (50). In some other versions, jaws (260, 270) of second grasping arm (250) do not open to release needle (50) until jaws (220, 230) of first grasping arm (210) have closed to grasp needle (50). Various suitable timing schemes and ways in which such schemes may be carried out will be described in greater detail below while others will be apparent to those of ordinary skill in the art in view of the teachings herein.

Once control of needle (50) has been effectively passed from second grasping arm (250) back to first grasping arm (210), second grasping arm (250) is rotated about longitudinal axis (140) to the position shown in FIG. 5G. Such rotation is provided by once again rotating sheath (280) relative to shaft (100). The rotational position of shaft (100) relative to longitudinal axis (130) continues to be fixed during the transition from the position shown in FIG. 5F to the position shown in FIG. 5G. It should be understood that, in the stage shown in FIG. 5G, grasping arms (210, 250) and needle (50) are in the same rotational positions relative to shaft (100) as shown in FIG. 2A.

Figure 5H:
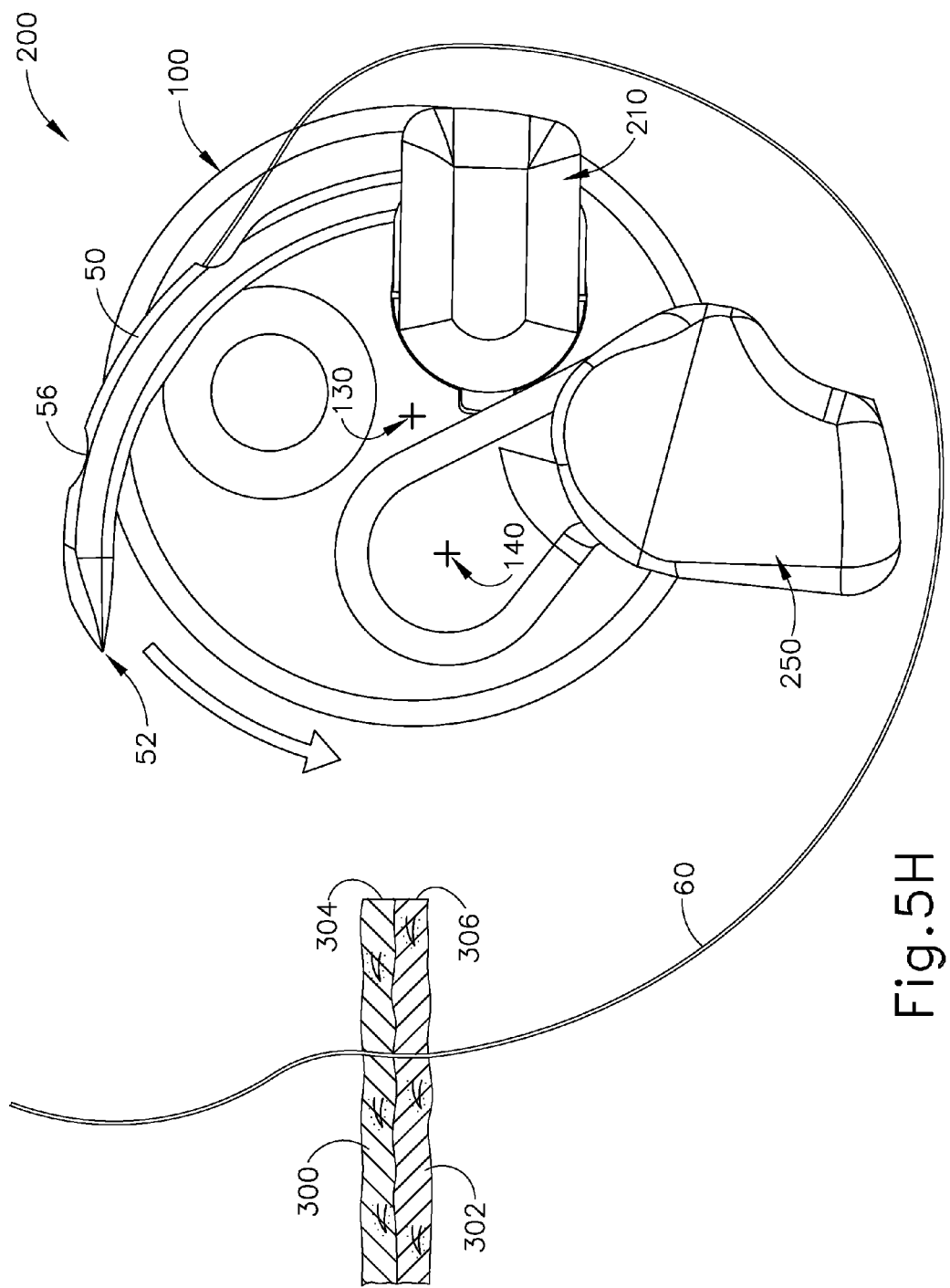
FIG. 5H depicts an end elevation view of the end effector and needle of FIG. 2A, during an exemplary eighth stage of operation.

Once second grasping arm (250) has been rotated away from needle (50) as shown in FIG. 5G, the entire instrument (10) is once again rotated about longitudinal axis (130) to position sharp tip (52) above tissue layers (300, 302), as shown in FIG. 5H. In the example shown, the rotational direction for instrument (10) is again counterclockwise viewed from the distal end toward the proximal end, though it should be understood that instrument (10) may be rotated clockwise instead (e.g., depending on the orientation of sharp tip (52)). During this transition, the rotational position of grasping arms (210, 250) relative to shaft (100) remains fixed, such that grasping arms (210, 250) rotate unitarily with shaft (100) about longitudinal axis (130). The longitudinal position of jaws (220, 230, 260, 270) also remains fixed during this transition. In the stage shown in FIG. 5H, grasping arms (210, 250) and needle (50) remain in the same rotational positions relative to shaft (100) as shown in FIG. 2A.

Having reached the configuration shown in FIG. 5H, end effector (200) may be moved back toward tissue layers (300, 302), such as along a path transverse to longitudinal axis (130), to again reach the position shown in FIG. 5A. The above described cycle may then be repeated as many times as desired until an appropriate number of stitches have been made through tissue layers (300, 302). The free end of suture (50) may then be knotted, clipped, or otherwise secured.

It should be understood that instrument (10) may be advanced distally or proximally along longitudinal axis (130) in each stitching cycle, each stitching cycle being represented by the succession of stages depicted in FIGS. 5A-5H. For instance, instrument (10) may be advanced distally or proximally along axis (130) during the transition from the position shown in FIG. 5E to the position shown in FIG. 5F. As another merely illustrative example, instrument (10) may be advanced distally or proximally along longitudinal axis (130) during the transition from the position shown in FIG. 5G to the position shown in FIG. 5H. Other suitable stages at which instrument (10) may be advanced distally or proximally will be apparent to those of ordinary skill in the art in view of the teachings herein. It should be understood that the distance of each incremental distal or proximal movement of instrument (10) during successive stitching cycles may be selected based on a desired stitch density along the length of the tissue being sutured. It should also be understood that, once stitching is complete, suture (60) may define a generally helical path through tissue layers (300, 302). Other suitable ways in which instrument (10) may be used will be apparent to those of ordinary skill in the art in view of the teachings herein.

As should be apparent to those of ordinary skill in the art, needle (50) of the present example orbits about longitudinal axis (140), which is offset from longitudinal axis (130) of shaft (100) in the present example. This may enable needle (50) to travel about an arc having a radius that is greater than the radius of a trocar through which shaft (100) is inserted. In other words, the circumferential path of needle (50) need not be limited to the circumference of the trocar through which shaft (100) is inserted when the orbital axis of needle (50) is offset from longitudinal axis (130) of shaft (100). Thus, the configuration of end effector (200) in the present example may permit a larger radius needle to be used, and larger stitches to be made, than what would be permitted if the orbital motion of needle (50) were centered about longitudinal axis (130) of shaft (100). In some other versions, needle (50) does move in an orbital fashion about longitudinal axis (130) of shaft (100). Surgical instrument (10) may be further operated in accordance with the teachings of U.S. patent application Ser. No. 13/295,203, entitled "Laparoscopic Suturing Instrument with Dual-Action Needle Graspers," filed Nov. 11, 2011, now U.S. Pat. No. 8,702,732, issued Apr. 22, 2014 and/or U.S. patent application Ser. No. 13/295,210, entitled "Laparoscopic Suturing Instrument with Perpendicular Eccentric Needle Motion," filed Nov. 11, 2011, now U.S. Pat. No. 8,906,043, issued Dec. 9, 2014, the disclosures of which are incorporated by reference herein.

IV. Exemplary Shaft

As noted above, surgical instrument (10) comprises a shaft (100) extending between handle assembly (400) and end effector (100). As shown in FIG. 6, shaft (100) comprises an outer tubular member encasing a pair of sheaths (240, 280) and drive shafts (244, 284). In the present example, a first sheath (240) and first drive shaft (244) extend from handle assembly (400) to first grasping arm (210). First drive shaft (244) is coaxial to and nested within first sheath (240). As noted above, sheath (240) is mechanically ground in the angular direction relative to shaft (100) and first grasping arm (210) via fins (226, 236) and slots (241, 242) described above. Accordingly, sheath (240) remains in a first position while first drive shaft (244) is rotatable therein. When first drive shaft (244) is rotated a first direction, jaws (220, 230) of first grasping arm (210) simultaneously translate away from each other, thereby allowing first grasping arm (210) to receive or catch needle (50). When first drive shaft (244) is rotated in the other direction, jaws (220, 230) of first grasping arm (210) simultaneously translate toward each other, thereby grasping needle (50) with first grasping arm (210).

A second sheath (280) and second drive shaft (284) extend from handle assembly (400) to second grasping arm (250). Second drive shaft (284) is coaxial to and nested within second sheath (280). In the present example, second sheath (280) is mechanically ground in the angular direction relative second grasping arm (250) via fins (266, 276) and slots (281, 282) described above; however, in the present example, second sheath (280) is rotatable relative to shaft (100). Accordingly, second sheath (280) is operable to rotate second grasping arm (250) relative to shaft (100) when second sheath (280) is rotated. In the present example, second drive shaft (284) is rotatable within and relative to second sheath (280). Thus, when second drive shaft (284) is rotated a first direction, jaws (260, 270) of second grasping arm (250) simultaneously translate away from each other, thereby allowing second grasping arm (250) to receive or catch needle (50). When second drive shaft (284) is rotated in the other direction, jaws (260, 270) of second grasping arm (250) simultaneously translate toward each other, thereby grasping needle (50) with second grasping arm (250). In some instances, second drive shaft (284) and second sheath (280) may be simultaneously rotated together relative to shaft (100) to maintain jaws (260, 270) in a substantially fixed longitudinal position while second grasping arm (250) is rotated about longitudinal axis (140).

In some versions, shaft (100), first sheath (240), and/or second sheath (280) may include one or more bushings along a corresponding longitudinal axis (130, 140) to support first sheath (240) and/or second sheath (280) while still permitting rotation of first sheath (240) and/or second sheath (280) relative to shaft (100). By way of example only, such bushings may comprise a plurality of thermoplastic parts disposed about first sheath (240) and/or second sheath (280) at predetermined longitudinal positions. In addition, or in the alternative, shaft (100) may include interiorly mounted bushings.

Of course other features and/or components may be used instead of bushings, such as bearings, pillow blocks, etc.

It should be understood that the foregoing description of the mechanical linkage of handle assembly (400) to end effector (200) is merely exemplary and other components and/or assemblies will be apparent to one of ordinary skill in the art in view of the teachings herein. For example, drive shafts (244, 284) may comprise resilient or bendable drive shafts. In some versions, one or more motors or actuators may be situated proximal to end effector (200) and coupled to one or more of sheaths (240, 280) and/or drive shafts (244, 284) to effect rotation. In such a version, a rotational sensor (not shown) may be disposed within handle assembly (400) to transmit instructions to the one or more motors or actuators. Still other configurations will be apparent to one of ordinary skill in the art in view of the teachings herein.

V. Exemplary Handle Assemblies

To control the operation of end effector (200) and grasping arms (210, 250) in accordance with the operation described in reference to FIGS. 5A-5H, an assembly (or assemblies) needs to control the opening and/or closing of jaws (220, 230, 260, 270) as well as the rotation of second grasping arm (250) relative to shaft (100). In the present example, sheaths (240, 280) and drive shafts (244, 284) are operable to control the opening and/or closing of jaws (220, 230, 260, 270) and the rotation of second grasping arm (250). The rotation of sheaths (240, 280) and/or drive shafts (244, 284) are controlled via handle assembly (400). In some versions, it may be desirable to the user to have manual control over the rotation of sheaths (240, 280) and/or drive shafts (244, 284) via a trigger or toggle button (404). For instance, users may prefer to finely control or reverse the movements of grasping arms (210, 250) shown in FIGS. 5A-5H in some situations. Accordingly, various exemplary manual control assemblies that may be used with handle assembly (400), a trigger, and/or toggle button (404) will now be discussed.

A. Exemplary Trigger-Operated Actuation and Toggle Actuation Handle Assembly FIGS. 7-15 depict a first exemplary handle assembly (500) having a trigger-operated actuation assembly (600) and a toggle actuation assembly (700). In the present example, trigger-operated actuation assembly (600) is operable to rotate both second sheath (280) and second drive shaft (284) shown and described in reference to FIG. 6. Rotation of both second sheath (280) and second drive shaft (284) results in second grasping arm (250) being rotated about longitudinal axis (140), such as the rotation shown in FIG. 5C. Thus, the rotational movement of second grasping arm (250) is controlled from within handle assembly (500). Toggle actuation assembly (700) is operable to rotate both first drive shaft (244) and second drive shaft (284) in opposite directions of rotation such that second needle grasping arm (250) grips needle (50) before or at substantially the same time as first grasping arm (210) relinquishes its grip on needle (50) and vice-versa. Accordingly, toggle actuation assembly (700) is operable to control which grasping arm (210, 250) grips needle (50). In combination, trigger-operated actuation assembly (600) and toggle actuation assembly (700) are operable to control the movement of grasping arms (210, 250) in accordance with the exemplary operation described above. It should be understood that the following operational descriptions can be reversed to undo or reverse the actions described.

i. Exemplary Trigger-Operated Actuation Assembly

Figure 7:
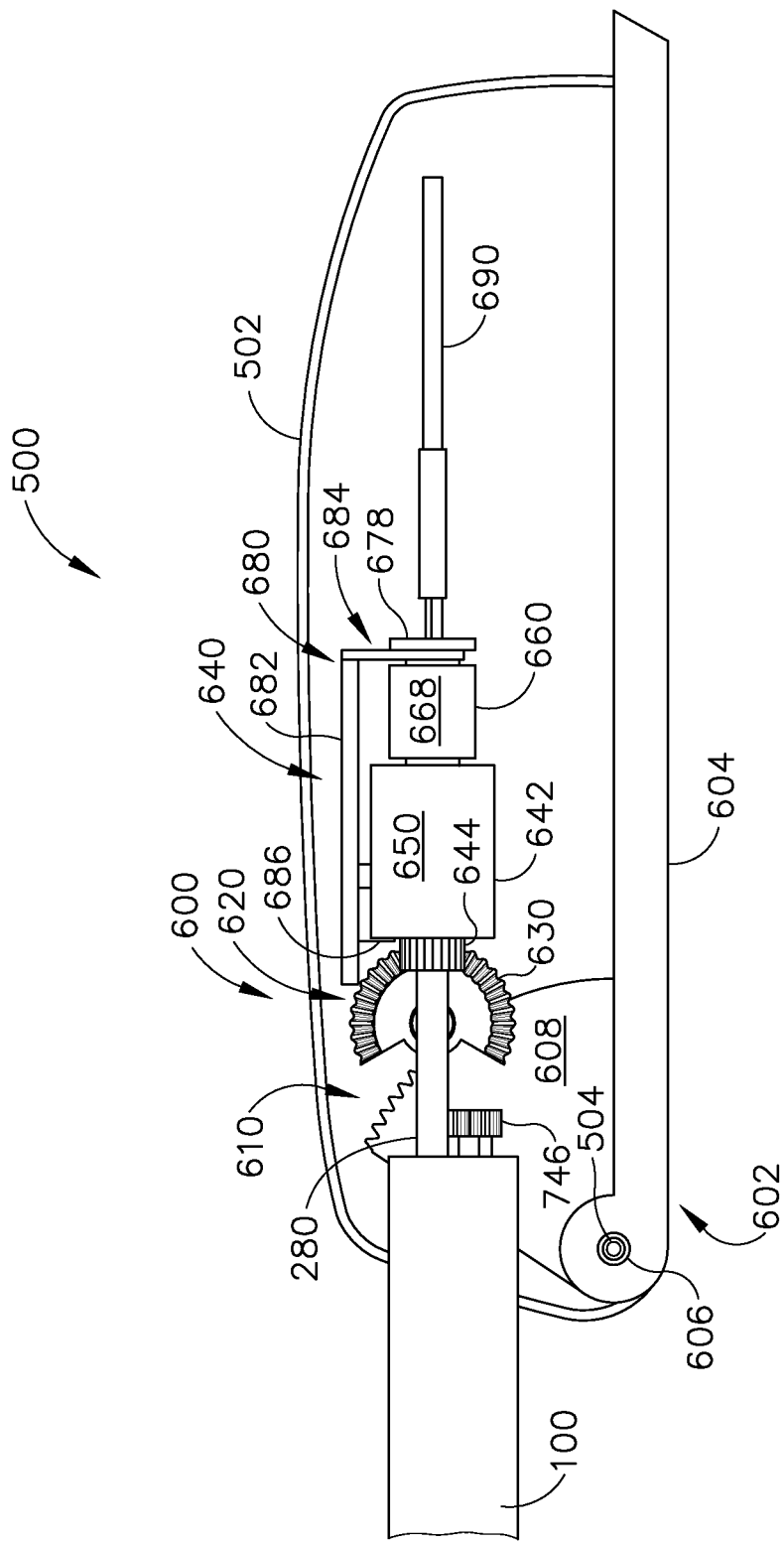
FIG. 7 depicts a side elevation view of an exemplary handle assembly showing an exemplary trigger-operated actuation assembly with an exemplary toggle actuation assembly of FIG. 13 omitted.

FIGS. 7-13 depict an exemplary trigger-operated actuation assembly (600) within a casing (502) of handle assembly (500) with toggle actuation assembly (700) omitted. Trigger-operated actuation assembly (600) comprises a trigger (602), a trigger gear assembly (620), a clutch assembly (640), second sheath (280), second drive shaft (284), and a rear drive shaft (690). As shown in FIG. 7, trigger (602) is pivotably mounted to casing (502) via a pivot (606) and an axle (504) (shown in phantom in FIG. 9) and is pivotable from a first, unactuated position (shown partially in FIG. 10A) to a second, actuated position (shown in FIGS. 7-9 and 10B). An intermediate position between the first, unactuated position and the second, actuated position corresponds to when trigger (602) engages clutch assembly (640), as will be detailed below.

a. Exemplary Trigger

Figure 8:
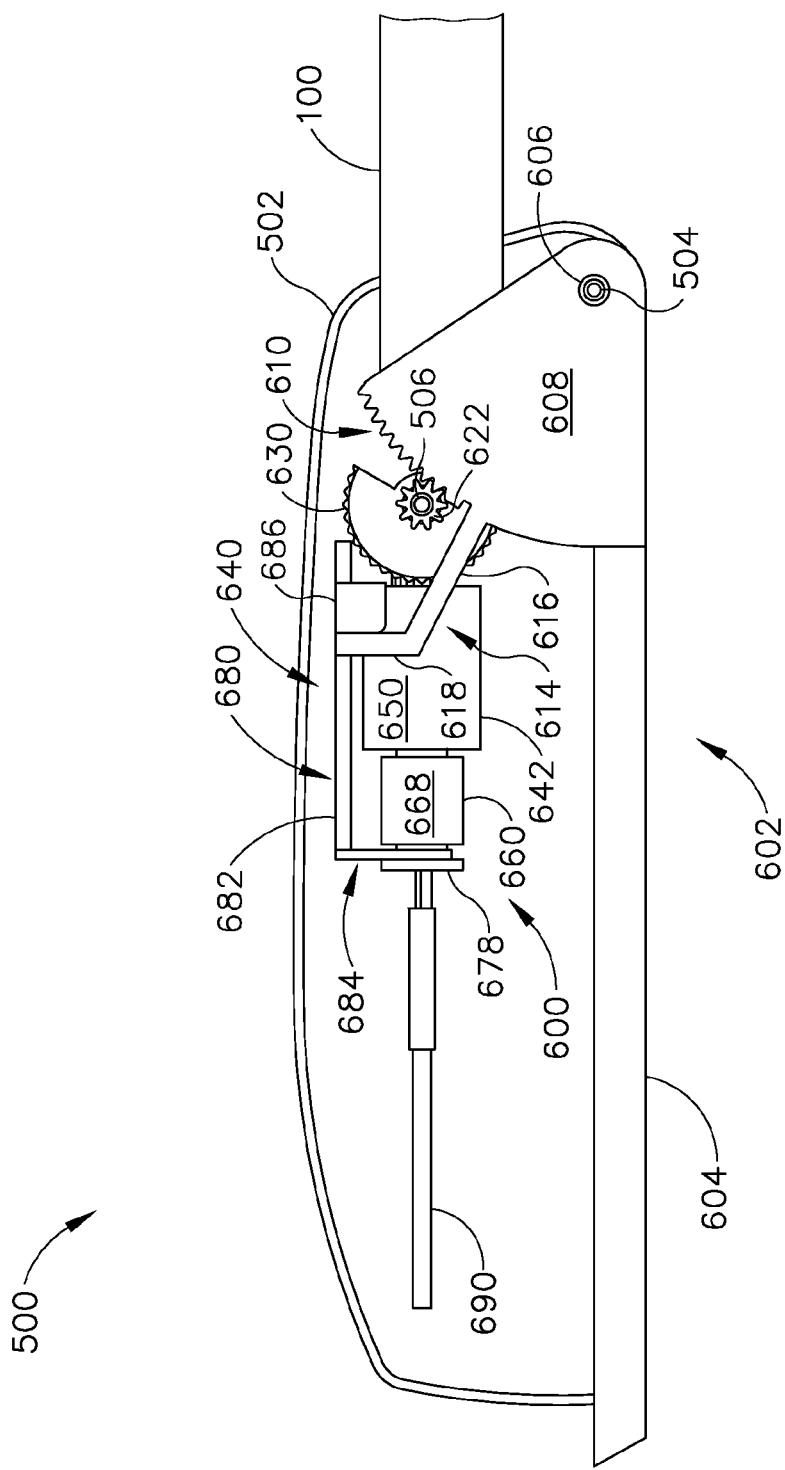
FIG. 8 depicts a reverse side elevation view of the trigger-operated actuation assembly of FIG. 7.

Trigger (602) of the present example comprises a lever (604), a pivot (606), an arcuate toothed member (608), and a clutch arm (614) (shown best in FIG. 8). In the present example, arcuate toothed member (608) comprises a plurality of teeth (610) configured to mesh and interface with trigger gear assembly (620), as will be described in greater detail below, to rotate trigger gear assembly (620). In addition, as shown best in FIGS. 10A-10B, arcuate toothed member (608) includes a cam feature (612) configured to engage a cam surface (628) of trigger gear assembly (620) such that trigger (602) maintains the position of trigger gear assembly (620) when once trigger (602) is pivoted to the intermediate position. Clutch arm (614), shown best in FIG. 8, comprises an extension member (616) and an angled member (618). In the present example, clutch arm (614) extends unitarily from arcuate toothed member (608) and is operable to actuate clutch assembly (640) via angled member (618) when trigger (602) is rotated from the intermediate position to the second, actuated position, as will also be described in greater detail below. Of course it should be understood that trigger (602) is merely exemplary and other configurations will be apparent to one of ordinary skill in the art in view of the teachings herein. For example, in some versions trigger (602) may include a latch that coupled to a feature on handle assembly (500) to retain trigger (602) in the second, actuated position. Furthermore, trigger (602) may include a return spring to rotationally bias trigger (602) toward the first, unactuated position.

b. Exemplary Trigger Gear Assembly

Figure 9:
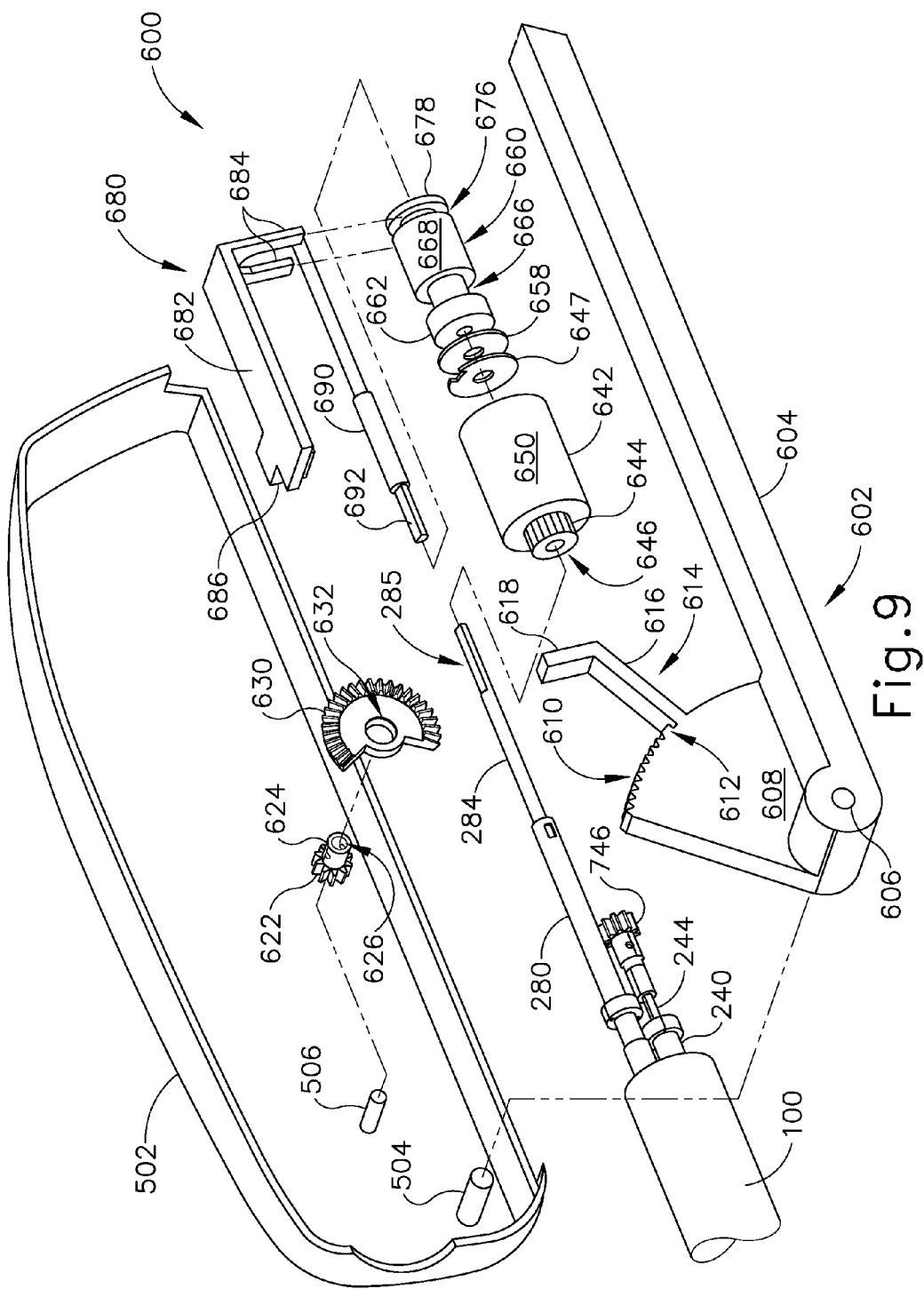
FIG. 9 depicts an exploded view of the trigger-operated actuation assembly of FIG. 7.

Trigger gear assembly (620) of the present example comprises a spur gear (622) and a partial bevel gear (630). As best shown in FIG. 9, spur gear (622) comprises a shaft (624) that is received in a central opening (632) of bevel gear (630). Shaft (624) is fixedly coupled to bevel gear (630) such that rotation of spur gear (622) also rotates bevel gear (630). By way of example only, shaft (624) may include a set screw (not shown) to affix spur gear (622) to bevel gear (630). In some versions, shaft (624) may be adhesively or otherwise fixedly coupled to bevel gear (630). In other versions, spur gear (622) and bevel gear (630) may be unitarily formed. Still further engagements of spur gear (622) with bevel gear (630) will be apparent to one of ordinary skill in view of the teachings herein. In the present example, spur gear (622) and bevel gear (630) have a ratio of approximately 10:1, inclusive, to approximately 15:1, inclusive. Shaft (624) includes a central opening (626) and is configured to rotate about an axle (506) of casing (502) such that trigger gear assembly (620) is carried by and rotatable relative to casing (502). Shaft (624) further includes a cam surface (628) (shown best in phantom in FIG. 10B) configured to engage with cam feature (612) of trigger (602) to maintain the position of trigger gear assembly (620) once trigger (602) is pivoted to the intermediate position. For instance, cam surface (628) may simply comprise a flat surface on the exterior of shaft (624). In the present example, spur gear (622) engages teeth (610) of trigger (602) such that pivoting of trigger (602) rotates spur gear (622). With spur gear (622) fixedly coupled to bevel gear (630), bevel gear (630) also rotates when trigger (602) is actuated. Still further configurations for trigger gear assembly (620) will be apparent to one of ordinary skill in the art in view of the teachings herein.

c. Exemplary Clutch Assembly

Figure 10A:
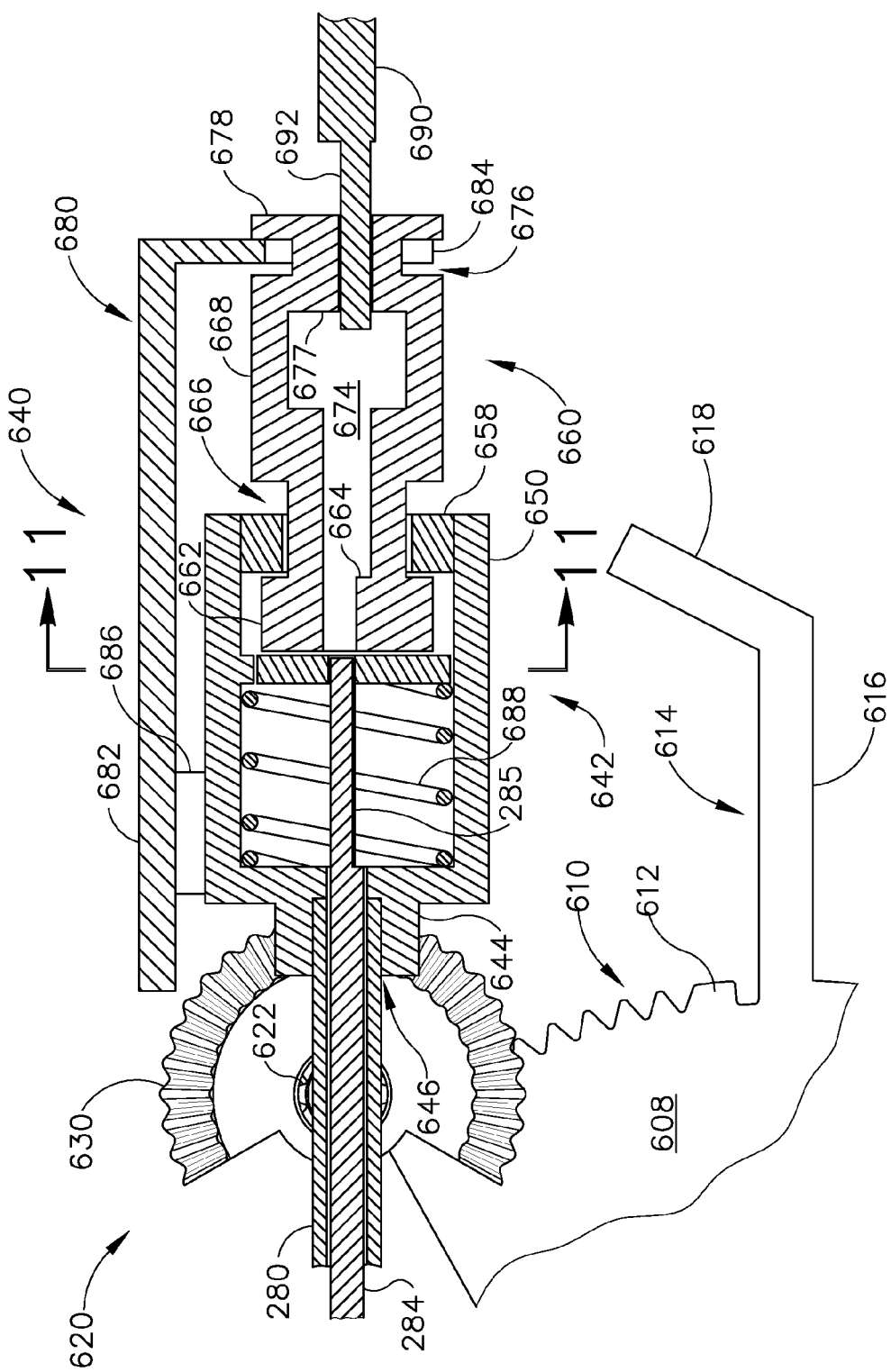
FIG. 10A depicts an enlarged longitudinal cross-sectional view of an exemplary clutch assembly of FIG. 7 shown in a first, unactuated position.
Figure 10B:
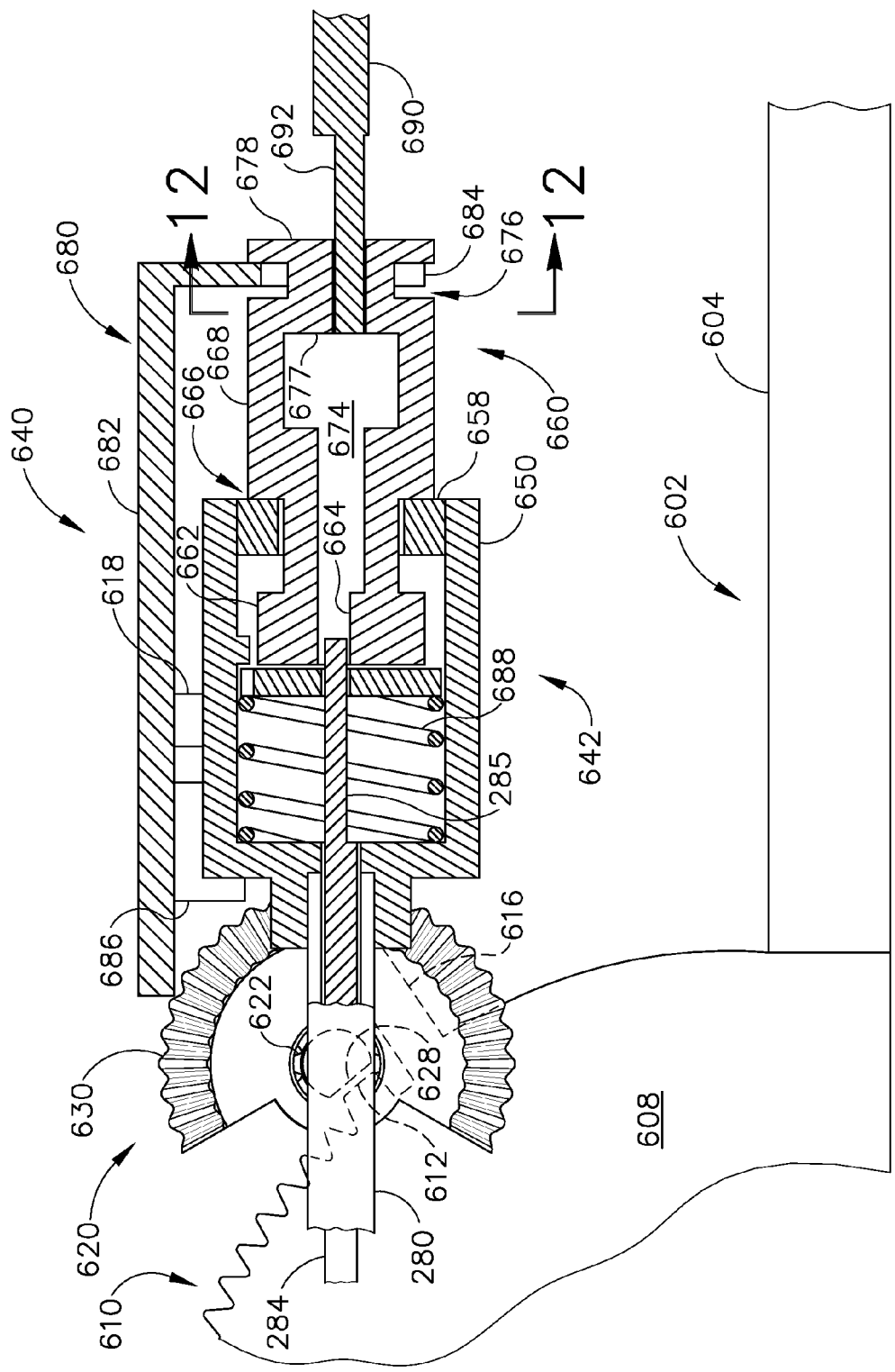
FIG. 10B depicts an enlarged longitudinal cross-sectional view of the clutch assembly of FIG. 10A shown in a second, actuated position.

Clutch assembly (640) of the present example is configured to substantially simultaneously rotate both second sheath (280) and second drive shaft (284) via a geared portion (644) as well as selectively engage or disengage rear drive shaft (690). Rear drive shaft (690) is utilized by toggle actuation assembly (700) and will be described in greater detail below. As shown best in FIGS. 9-10B, clutch assembly (640) comprises a distal member (642), a locking member (647), a retention insert (658), a proximal member (660), an actuation plate (680), and a return spring (688). Distal member (642) of the present example comprises a unitary distal geared portion (644), a main cylinder (650), and a tab (652). Main cylinder (650) extends proximally from distal geared portion (644) and comprises a substantially hollow cylinder configured to slidably receive a distal portion (662) of proximal member (660) therein, as will be described in more detail below. In the present example, tab (652) extends inwardly from main cylinder (650) and is operable to selectively rotationally fix locking member (647) relative to distal member (642). Return spring (688) is disposed within main cylinder (650) and is resiliently biased to urge locking member (647) and proximal member (660) proximally relative to distal member (642). Distal geared portion (644) comprises a cylindrical pinion gear unitarily coupled to a distal end of main cylinder (650) that is configured to engage with bevel gear (630) to rotate distal member (642) when trigger (602) is pivoted. Referring to FIGS. 10A-10B, a longitudinal opening (646) of distal geared portion (644) receives and is fixedly coupled to sheath (280) such that rotation of distal member (642) via distal geared portion (644) also rotates sheath (280). In some versions, sheath (280) may comprise spline features to engage with the interior of distal geared portion (644). In addition, or in the alternative, distal geared portion (644) may include a set screw (not shown) configured to rotationally fix sheath (280) relative to distal member (642). In yet a further version, distal geared portion (644) may be omitted and a separate bevel gear may be coupled to sheath (280). Of course still further engagement features or couplings for sheath (280) to distal member (642) will be apparent to one of ordinary skill in the art in view of the teachings herein.

Figure 11:
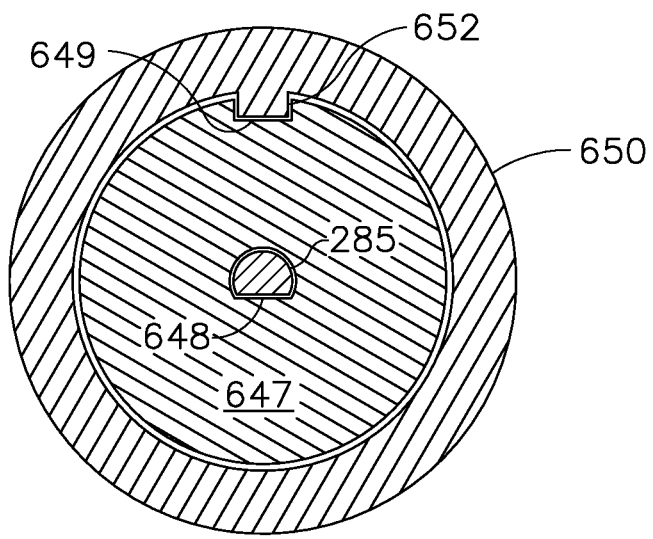
FIG. 11 depicts an enlarged transverse cross-sectional view of the clutch assembly of FIG. 10B taken along section line 11-11 shown in FIG. 10A.

In the present example, distal member (642) is also configured to rotationally engage second drive shaft (284) via locking member (647). In the present example, second drive shaft (284) comprises a keyed portion (285) that extends into distal member (642). As best seen in FIG. 11, keyed portion (285) comprises a semi-circular member configured to engage flats (648, 664), shown in FIGS. 10A-10B, of locking member (647) and proximal member (660), respectively. Locking member (647) further includes a slot (649) that is sized to receive tab (652) therein. In the present configuration, spring (688) urges locking member (647) proximally to engage tab (652) with slot (649). In some versions, a plurality of slots (649) may be disposed about locking member (647) such that tab (652) and slots (649) may engage in multiple orientations. Thus, when tab (652) and slot (649) are engaged, rotation of distal member (642) also rotates locking member (647) and, consequently, second drive shaft (284) via flat (648). Accordingly, when trigger (602) is pivoted and bevel gear (630) rotates distal member (642), second drive shaft (284) and second sheath (280) are simultaneously rotated. Second grasping arm (250) may be rotated about longitudinal axis (140) in accordance with the examples shown in FIGS. 5C, 5D, 5F, and 5G when trigger (602) is pivoted. Since second drive shaft (284) and second sheath (280) are rotated simultaneously by actuating trigger (602), second grasping arm (250) will maintain an open or closed configuration during such rotation. When proximal member (660) is urged distally by actuation plate (680), as will be described in greater detail below, locking member (647) is actuated distally such that tab (652) is disengaged from slot (649). Accordingly, second drive shaft (284) may be rotated relative to distal member (642) as will be described later herein.

Still referring to FIGS. 10A-10B, clutch assembly (640) also includes a proximal member (660) that comprises a distal portion (662), an annular retention recess (666), an intermediate portion (668), an annular plate recess (676) and a proximal flange (678). A longitudinal channel (674) extends through proximal member (660) and is configured to receive keyed portion (285) of second drive shaft (284) at a distal end and a distal keyed end (692) of rear drive shaft (690) at a proximal end. As noted above, distal portion (662) is slidably received in main cylinder (650) of distal member (642) and is biased proximally by spring (688). As shown in FIG. 10B, distal portion (662) is sized such that distal portion (662) does not engage or is otherwise interfered with by tab (652). The interior of distal portion (662) further includes a flat (664) that selectively engages keyed portion (285) of second drive shaft (284) when proximal member (660) is actuated, as will be described below. Distal portion (662) of proximal member (660) is retained within main cylinder (650) of distal member (640) by retention insert (658) and annular retention recess (666). Retention insert (658) of the present example comprises an annular two-piece collar that encircles annular retention recess (666) and is fixedly coupled to a proximal end of main cylinder (650). By way of example only, retention insert (658) may initially be coupled together about annular retention recess (666) then fixedly coupled to main cylinder (650). Retention insert (658) may be fixedly coupled to main cylinder (650) via a set screw, complementary threading, adhesive attachment, etc. When retention insert (658) is fixedly coupled to main cylinder (650) and encircles annular retention recess (666), proximal member (660) is slidable relative to distal member (642) through retention insert (658), but is longitudinally restrained from decoupling from distal member (642) by retention insert (658). Thus, spring (688), locking member (647), and distal portion (662) of proximal member (660) are retained within distal member (650). Of course retention insert (658) and annular retention recess (666) are merely exemplary and may be omitted. In some versions, distal portion (662) may instead include a keyway and main cylinder (650) may include a protrusion, similar to tab (652), such that proximal member (660) is initially insertable into main cylinder (650) when the keyway and protrusion are aligned. Proximal member (660) is then rotated such that the protrusion and keyway are no longer aligned, but distal portion (662) of proximal member (660) is retained within distal member (650) by the protrusion. Of course still further slidable retention couplings for proximal member (660) and distal member (640) will be apparent to one of ordinary skill in the art in view of the teachings herein.

Figure 12:
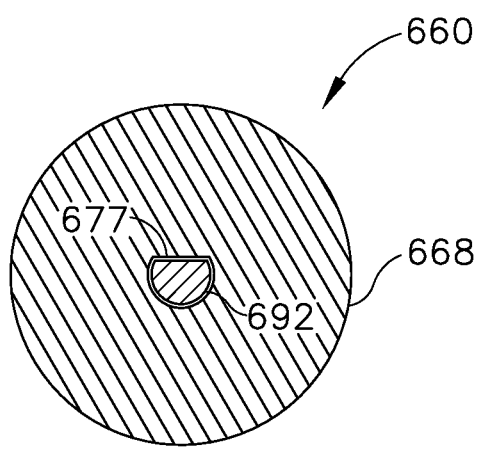
FIG. 12 depicts an enlarged transverse cross-sectional view of the clutch assembly of FIG. 10B taken along section line 12-12 shown in FIG. 10B.

Intermediate portion (668) extends proximally from annular retention recess (666) and terminates at annular plate recess (676). In the present example, annular plate recess (676) is configured to engage forks (684) of actuation plate (680), as will be described in greater detail below. Proximal flange (678) extends from annular plate recess (676) and is configured to longitudinally retain forks (684) within annular plate recess (676). In the example shown, longitudinal channel (674) narrows to a semi-circular channel by another flat (677), as best shown in FIG. 12. Flat (677) engages distal keyed end (692) of rear drive shaft (690) such that rear drive shaft (690) is engaged and rotatable with proximal member (660). Of course it should be understood that flat (677) may be omitted and the proximal end of longitudinal channel (674) may include a spline feature to rotationally couple rear drive shaft (690) with proximal member (660). Still further configurations for proximal member (660) will be apparent to one of ordinary skill in the art in view of the teachings herein.

Referring back to FIG. 9, actuation plate (680) is configured to engage and longitudinally actuate proximal member (660) relative to distal member (642). In the present example, actuation plate (680) includes a longitudinal plate (682), a pair of forks (684) extending substantially perpendicularly to longitudinal plate (682), and an engagement tab (686) extending transversely from longitudinal plate (682). As shown in FIG. 9, forks (684) engage with annular plate recess (676) such that longitudinal actuation of actuation plate (680) also longitudinally actuates proximal member (660). Of course forks (684) are merely optional and other engagement features will be apparent to one of ordinary skill in the art in view of the teachings herein. By way of example only, such engagement features may include adhesive attachment, mechanical features, etc. Engagement tab (686) extends outwardly from longitudinal plate (682) and is configured to be actuatable by clutch arm (614). When trigger (602) is actuated from the intermediate position to the second, actuated position, angled member (618) of clutch arm (614) abuts a proximal edge of engagement tab (686) and longitudinally actuates actuation plate (680) distally via engagement tab (686), as shown in FIG. 8. With forks (684) engaged with proximal member (660), actuation plate (680) is thereby operable to longitudinally actuate proximal member (660) relative to distal member (640). It should be understood that actuation of proximal member (660) distally will also actuate locking member (647) as well. Still further arrangements for actuation plate (680) will be apparent to one of ordinary skill in the art in view of the teachings herein.

d. Operation of Clutch Assembly

FIG. 10A shows clutch assembly (640) in a first, unactuated position. In this position, trigger (602) is also shown in the first, unactuated position such that arcuate toothed member (608) has not rotated trigger gear assembly (620) and clutch arm (614) has not actuated actuation plate (680) via engagement tab (686). As trigger (602) is pivoted about axle (504), teeth (610) of arcuate toothed member (608) mesh with and rotate trigger gear assembly (620). As noted above, trigger gear assembly (620) engages with distal member (642) of clutch assembly (640) and simultaneously rotates second drive shaft (284) and second sheath (280). Thus, as trigger (602) is pivoted, second grasping arm (250) is rotated about longitudinal axis (140) relative to shaft (100), such as the motions shown in FIGS. 5C, 5D, 5F, and 5G. It should be understood that, in the present example, trigger gear assembly (620) is configured such that keyed portion (285) of second drive shaft (284) rotationally aligns with flat (664) of proximal member (660) at the end of the rotation of second grasping arm (250).

When trigger (602) reaches the intermediate position, clutch arm (614) abuts engagement tab (686) of actuation plate (680), as shown in FIG. 8. In this position, teeth (610) no longer engage spur gear (622) and cam feature (612) is engaged with cam surface (628) of trigger gear assembly (620). Thus, cam feature (612) maintains the rotational position of trigger gear assembly (620), and consequently second grasping arm (250), once trigger (602) has fully rotated second grasping arm (250). As trigger (602) continues to pivot to the second, actuated position, cam feature (612) slides against cam surface (628) while clutch arm (614) actuates engagement tab (686) and translates actuation plate (680) distally. With forks (686) engaged with proximal member (660), actuation plate (680) actuates proximal member (660) and locking member (647) distally. Slot (649) of locking member (647) thereby disengages from tab (652) while keyed portion (285) of second drive shaft (284) inserts into and engages with flat (664) of distal portion (662) of proximal member (660), shown in FIG. 10B. Thus, when trigger (602) is in the second, actuated position, proximal member (660) rotationally couples second drive shaft (284) to rear drive shaft (690). Accordingly, when rear drive shaft (690) is rotated, as will be described below, second drive shaft (284) is also rotated. In the second, actuated position, cam feature (612) and cam surface (628) cooperatively retain trigger gear assembly (620) from rotating, thereby maintaining the rotational position of sheath (280) while second drive shaft (284) is rotated therein. It should be understood that the foregoing exemplary clutch assembly (640) is merely exemplary and other clutch assemblies, such as clutch assembly (1150) described below, may be used by one of ordinary skill in the art in view of the teachings herein.

ii. Exemplary Toggle Actuation Assembly

Once second grasping arm (250) is in the rotational position depicted in FIG. 5C, it may be desirable to transfer control of needle (50) from first grasping arm (210) to second grasping arm (250), as shown and described in reference to FIGS. 5C-5D. As discussed above, jaws (260, 270) of second grasping arm (250) are closed about a portion of needle (50) and jaws (220, 230) of first grasping arm (210) are opened to release needle (50) while first sheath (240) and second sheath (280) remain rotationally stationary. To effectuate this operation, first drive shaft (244) is rotated in a first direction and second drive shaft (284) is rotated in a second direction, opposite the first direction. In some versions, second drive shaft (284) is rotated first to grasp needle (50) with second grasping arm (250) while first grasping arm (210) still grasps needle (50). Once second grasping arm (250) has closed or substantially closed to grasp needle (50), first drive shaft (244) is rotated to release needle (50) from the grasp of first grasping arm (210). Accordingly, needle (50) in this example is always grasped by at least one arm (210, 250) or the other (210, 250) during the transfer. In the present example, toggle actuation assembly (700) is provided within handle assembly (500) to operate first drive shaft (244) and second drive shaft (284) to transfer needle (50) from one arm (210, 250) to the other (210, 250). Of course it should be understood that toggle actuation assembly (700), when reversed from the below description, can transfer needle (50) in the opposite direction.

Figure 13:
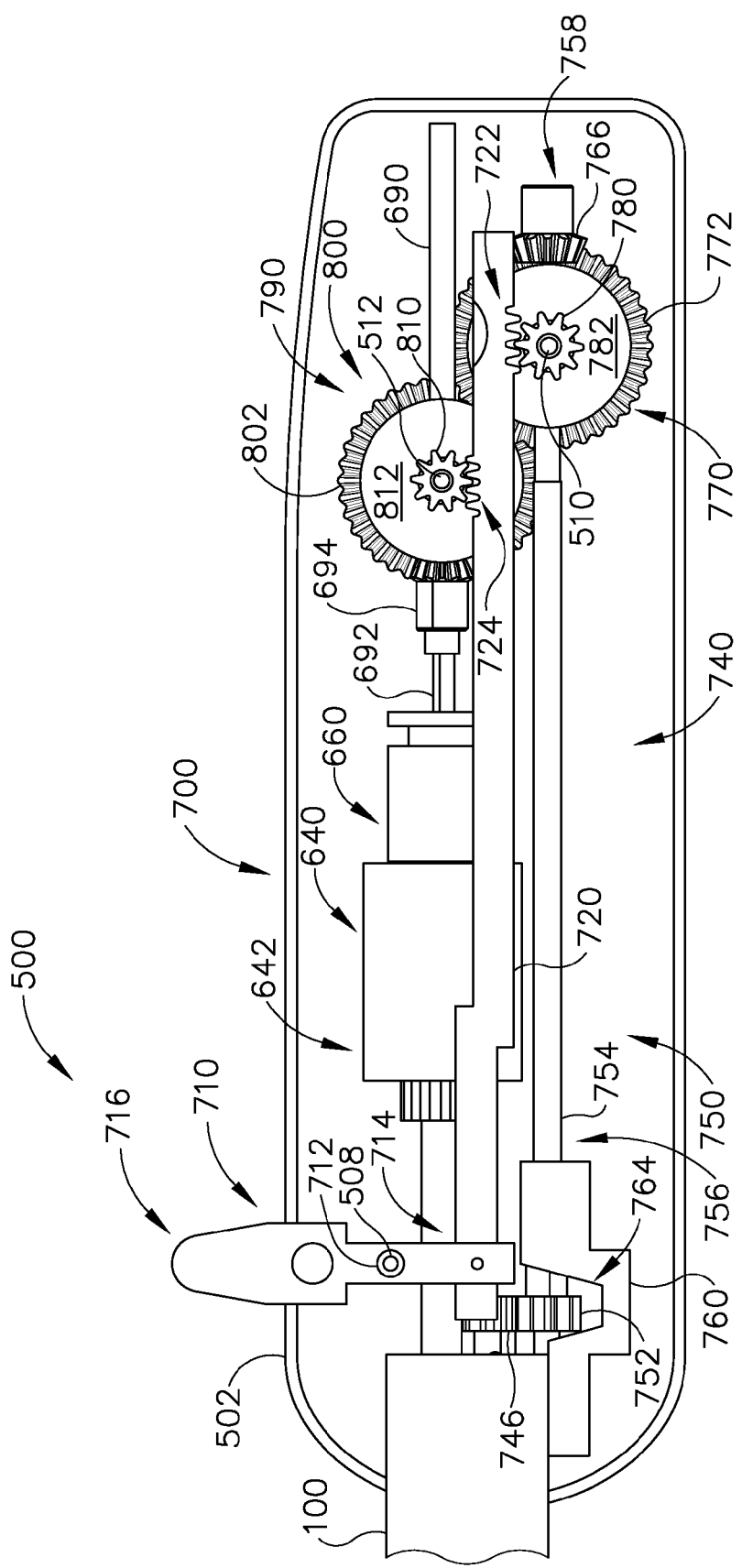
FIG. 13 depicts a side elevation view the handle assembly of FIG. 7 showing an exemplary toggle actuation assembly with the trigger-operated actuation assembly of FIG. 7 omitted.
Figure 14:
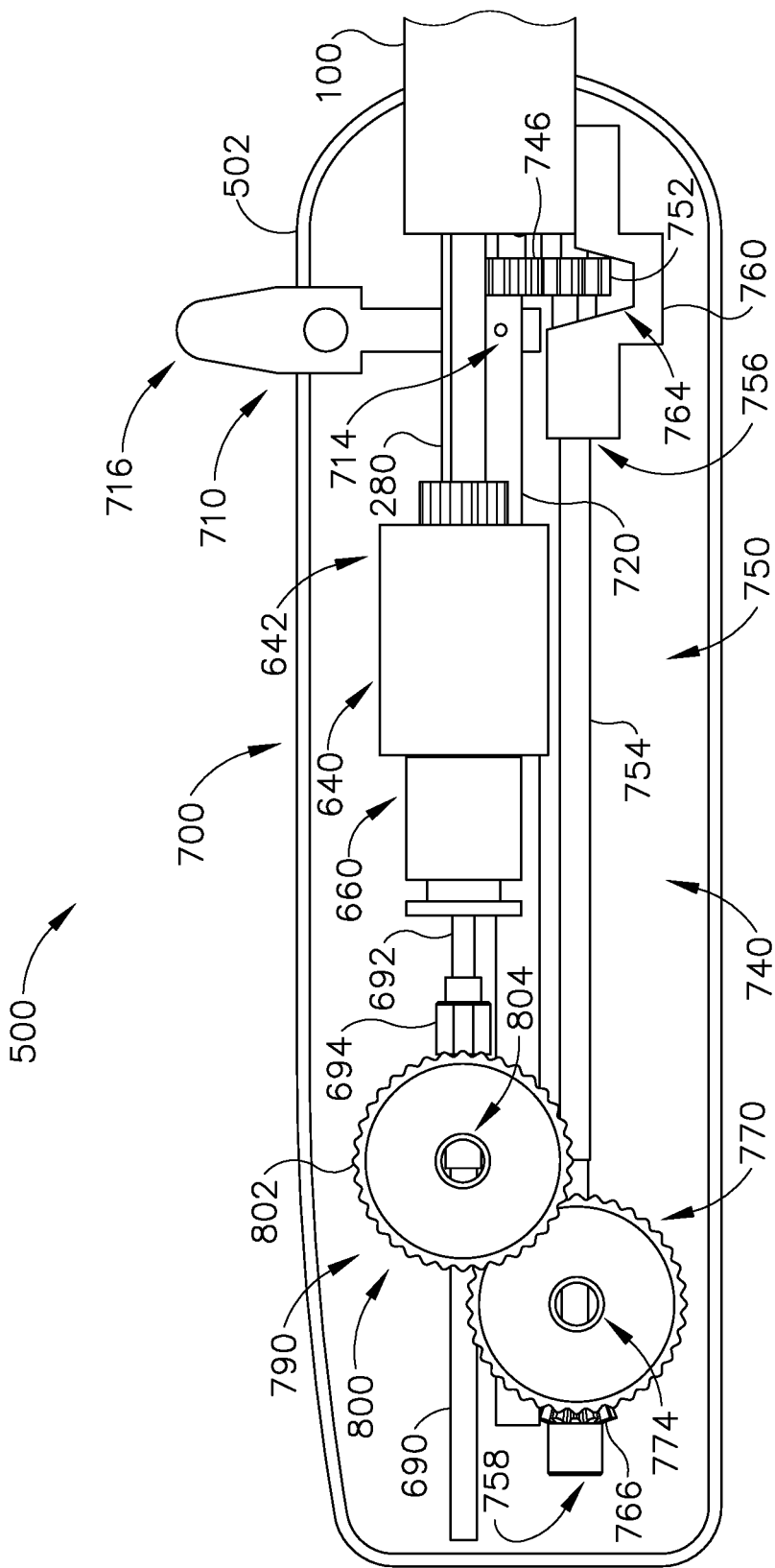
FIG. 14 depicts a reverse side elevation view of the toggle actuation assembly of FIG. 13.
Figure 15:
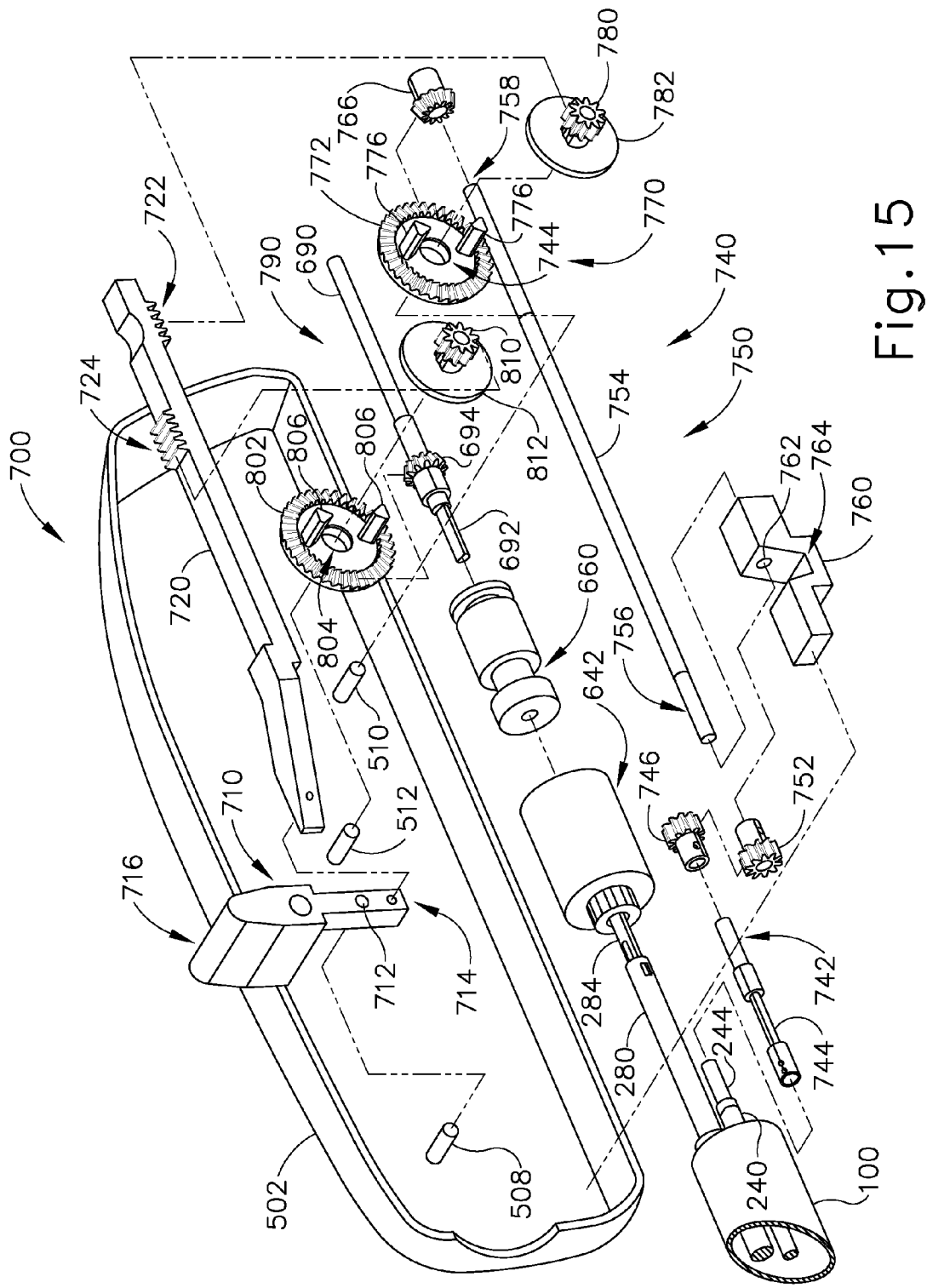
FIG. 15 depicts an exploded view of the toggle actuation assembly of FIG. 13.

FIGS. 13-15 depict an exemplary toggle actuation assembly (700) within handle assembly (500) having trigger-operated actuation assembly (600) omitted for clarity. Toggle actuation assembly (700) of the present example comprises a toggle (710), a rack (720), a first drive train (740), and a second drive train (790).

a. Exemplary Toggle and Rack

Toggle (710) is pivotably mounted to casing (502) via axle (508) and pivot (712) and is operable to longitudinally actuate rack (720) relative to first drive train (740) and second drive train (790). Toggle (710) is rotatably coupled at a first end (714) to rack (720) and is operable by a user at a second end (716) that protrudes from casing (502). Rack (720) comprises a longitudinally extending member having a first rack gear section (722) and a second rack gear section (724). In the present example, first rack gear section (722) is oriented downwardly and is configured to engage first drive train (740). Second rack gear section (724) is positioned distal of first rack gear section (722) and is oriented upwardly to engage second drive train (790). Second rack gear section (724) is longitudinally positioned relative to first rack gear section (722) such that second rack gear section (724) engages second drive train (790) followed by first rack gear section (722) engaging first drive train (740) when rack (720) is actuated distally by toggle (710). In this arrangement, second rack gear section (724) is operable to rotate second drive shaft (284) via second drive train (790), described in greater detail below, to cause second grasping arm (250) to grip needle (50) prior to first rack gear section (722) rotating first drive shaft (244) via first drive train (740), described in greater detail below, to cause first grasping arm (210) to release needle (50). In some versions, second rack gear section (724) and first rack gear section (722) may be positioned to simultaneously rotate second drive shaft (284) and first drive shaft (244). In some other versions, second rack gear section (724) and first rack gear section (722) may be positioned to initially rotate second drive shaft (284) and subsequently rotate first drive shaft (244) while second drive shaft (284) is still rotating. Of course further configurations for rack (720) and/or toggle (710) will be apparent to one of ordinary skill in the art in view of the teachings herein.

b. Exemplary First Drive Train

First drive train (740) is operable to rotate first drive shaft (244) when first rack gear section (722) engages first drive train (740). As seen best in FIG. 15, first drive train (740) of the present example comprises a first drive shaft assembly (742), a transfer axle assembly (750), and a first gear assembly (770). First drive shaft assembly (742) comprises an intermediate shaft (744) that is fixedly coupled to first drive shaft (244) at a first end and a spur gear (746) that is fixedly coupled to a second end of intermediate shaft (744). Spur gear (746) of the present example meshes with and engages a second spur gear (752) of transfer axle assembly (750).

Transfer axle assembly (750) comprises second spur gear (752), a transfer axle (754), a mounting member (760), and a first rear bevel gear (766). As shown in FIGS. 13-14, mounting member (760) is fixedly coupled to shaft (100) and supports a distal end (756) of transfer axle (754) by an opening (762) formed through a rear portion of mounting member (760). In some versions transfer axle (756) is vertically aligned with second drive shaft (244) while in others transfer axle (756) is offset from the vertical plane in which second drive shaft (244) lies. Mounting member (760) of the present example further includes a recessed portion (764) sized to permit second spur gear (752) to rotate when second spur gear (752) is fixedly coupled to distal end (756) of transfer axle (754) that is inserted through opening (762). First rear bevel gear (766) is fixedly coupled to a proximal end (758) of transfer axle (754) and is configured to mesh with and engage first bevel gear (772) of first gear assembly (770).

Referring back to FIG. 15, first gear assembly (770) comprises a first bevel gear (772) and a first pinion gear (780). First bevel gear (772) is rotatably mounted to casing (502) on an axle (510) that is inserted through a central opening (774) in first bevel gear (772). First bevel gear (772) further includes a pair of standoffs (776) that offset first pinion gear (780) from first bevel gear (772). In the present example, standoffs (776) are fixedly coupled to a plate (782) of first pinion gear (780) such that first bevel gear (772) and first pinion gear (780) are rotationally fixed relative to each other. Accordingly, first pinion gear (780) is operable to rotate first rear bevel gear (766) when first bevel gear (772) meshes with and engages first rear bevel gear (766). In this configuration, standoffs (776) extend around transfer axle (754) such that first bevel gear (772) is on a first side of transfer axle (754) and first pinion gear (780) is on an opposite side. Referring to FIG. 13, first pinion gear (780) engages with first rack section (722) such that actuation of rack member (720) rotates first gear assembly (770), which in turn rotates first drive shaft (244), thereby opening or closing jaws (220, 230) of first grasping arm (210), described in greater detail above. It should be understood that first sheath (240) is rotationally fixed relative to casing (502) throughout all stages of operation, to provide a mechanical ground relative to first drive shaft (244). Of course still further configurations and assemblies for first drive train (740) will be apparent to one of ordinary skill in the art in view of the teachings herein.

c. Exemplary Second Drive Train

Second drive train (790) comprises rear drive shaft (690) and a second gear assembly (800). As described above, rear drive shaft (690) extends into clutch assembly (640) and comprises a distal keyed end (692). In addition, as shown in FIGS. 13 and 15, a second rear bevel gear (694) is fixedly coupled to rear drive shaft (690) and is configured to engage with second gear assembly (800) such that rotation imparted by second gear assembly (800) causes distal keyed end (692) to rotate as well. Second gear assembly (800) comprises a second bevel gear (802) and a second pinion gear (810). Second bevel gear (802) is rotatably mounted to casing (502) on an axle (512) that is inserted through a central opening (804) in second bevel gear (802). Second bevel gear (802) further includes a pair of standoffs (806) that offset second pinion gear (810) from second bevel gear (802). In the present example, standoffs (806) are fixedly coupled to a plate (812) of second pinion gear (810) such that second bevel gear (802) and second pinion gear (810) are rotationally fixed relative to each other. Accordingly, second pinion gear (810) is operable to rotate second rear bevel gear (694) when second bevel gear (802) meshes with and engages second rear bevel gear (694). In this configuration, standoffs (806) extend around rear drive shaft (690) such that second bevel gear (802) is on a first side of rear drive shaft (690) and second pinion gear (810) is on an opposite side. Referring to FIG. 13, second pinion gear (810) engages with second rack section (724) such that actuation of rack member (720) rotates second gear assembly (800), which in turn rotates second drive shaft (284) when clutch assembly (640) is engaged, thereby opening or closing jaws (260, 270) of second grasping arm (250), described in greater detail above. It should be understood that second sheath (280) is rotationally fixed relative to casing (502) via engagement of cam feature (612) with cam surface (624) during this particular stage of operation, such that second sheath (280) provides a mechanical ground relative to second drive shaft (284). Of course still further configurations and assemblies for second drive train (800) will be apparent to one of ordinary skill in the art in view of the teachings herein.

d. Exemplary Operation of Toggle Actuation Assembly

Once clutch assembly (640) has engaged rear drive shaft (690) with second drive shaft (284), as shown in FIG. 10B, a user actuates toggle (710) to transfer needle (50) from first grasping arm (210) to second grasping arm (250), as shown and described in reference to FIGS. 5C-5D. In the present example, toggle (710) is initially in a forward position such that rack sections (722, 724) are positioned proximally of pinion gears (780, 810). In this position, jaws (260, 270) of second grasping arm (250) are in an open position and disposed about needle (50). Jaws (220, 230) of first grasping arm (210) are in a closed position and grasp needle (50) with first grasping arm (210). As toggle (710) is rotated rearwardly, in the present example, initially second rack section (724) engages second pinion gear (810) to rotate rear drive shaft (690). The rotation of rear drive shaft (690) is transferred through proximal member (660) to second drive shaft (284) when proximal member (660) is engaged with keyed portion (285) of second drive shaft (284). Thus, as toggle (710) is pivoted, second drive shaft (284) is rotated to close second grasping arm (250) to grasp needle (50).

As toggle (710) continues to be pivoted rearwardly, first rack section (722) engages first pinion gear (780) to rotate transfer axle (256). Second spur gear (752) of transfer axle (256) engages with spur gear (746) on intermediate shaft (744), thereby rotating first drive shaft (244). Thus, as toggle (710) continues pivoting, first drive shaft (244) is rotated to open first grasping arm (210) to release needle (50) after second grasping arm (250) grasps needle (50). Accordingly, toggle actuation assembly (700) is operable to transfer grip of needle (50) from first grasping arm (210) to second grasping arm (250). It should be understood from the foregoing that toggle actuation assembly (700) is operable to rotate first drive shaft (244) in a first direction and second drive shaft (284) in a second direction that is opposite the first direction. Of course, in some versions, threaded sections (246, 248, 286, 288) and threading (228, 238, 268, 278), described above, may be configured such that drive shafts (244, 284) may be rotated in the same direction while one set of jaws (220, 230, 260, 270) closes and another set of jaws (220, 230, 260, 270) opens. Still further configurations will be apparent to one of ordinary skill in the art in view of the teachings herein.

In some versions, trigger (602) may then be released to disengage clutch assembly (640) and to rotate second grasping arm (250) away from first grasping arm (210), such as that shown in FIG. 5D. The user may then proceed in accordance with the operation described above in reference to FIGS. 5E-5H. In some versions, the rotation of drive shafts (244, 284) is a 360 degree rotation such that the components of toggle actuation assembly (700) are in the same position regardless of which grasping arm (210, 250) grasps needle (50). Such rotation may ensure that keyed portion (285) of second drive shaft (284) and distal keyed end (692) of rear drive shaft (690) remain aligned with the components of clutch assembly (640). It should be understood that actuating toggle (710) forwardly will reverse the above-described actions and transfer needle (50) from second grasping arm (250) to first grasping arm (210). Trigger (602) may then be pivoted back to the first, unactuated position to reset instrument (10).

In some versions, one or more brake assemblies (not shown) retain transfer axle (754) and/or rear drive shaft (690) in a fixed position until toggle (710) is actuated. In addition, or in the alternative, a retention feature (not shown) may be associated with proximal member (660) and/or actuation plate (680) such that rack (720) is prevented from actuating unless the retention feature is released by proximal member (660) and/or actuation plate (680) actuating distally relative to distal member (642) of clutch assembly (640). Accordingly, such a feature may resist a user's attempt to move toggle (710) until clutch assembly (640) is engaged. Further still, a feature may selectively lock trigger (602) in the second, actuated position until toggle actuation assembly (700) is actuated. Of course further configurations for toggle actuation assembly (700) will be apparent to one of ordinary skill in the art in view of the teachings herein.

B. Exemplary Alternative Handle Assembly with Alternative Trigger-Operated Actuation Assembly and Toggle Actuation Assembly FIGS. 16-20 depict an exemplary alternative handle assembly (1000) having an exemplary alternative trigger-operated actuation assembly (1100) and an exemplary alternative toggle actuation assembly (1200). As with the above-described trigger-operated actuation assembly (600), alternative trigger-operated actuation assembly (1100) is also operable to rotate both second sheath (280) and second drive shaft (284) shown and described in reference to FIG. 6. Rotation of both second sheath (280) and second drive shaft (284) results in second grasping arm (250) being rotated about longitudinal axis (140), such as the rotation shown in FIGS. 5C, 5D, 5F, and 5G. Thus, the rotational movement of second grasping arm (250) is controlled from within handle assembly (1000). Toggle actuation assembly (1200) is operable to rotate both first drive shaft (244) and second drive shaft (284) in opposite directions of rotation such that second needle grasping arm (250) grips needle (50) before or at substantially the same time as first grasping arm (210) relinquishes its grip on needle (50) and vice-versa. Accordingly, toggle actuation assembly (1200) is operable to control which grasping arm (210, 250) grips needle (50). In combination, trigger-operated actuation assembly (1100) and toggle actuation assembly (1200) are operable to control the movement of grasping arms (210, 250) in accordance with the exemplary operation described above. It should be understood that the following operational descriptions can be reversed to undo or reverse the actions described.

i. Exemplary Alternative Trigger-Operated Actuation Assembly

Figure 16:
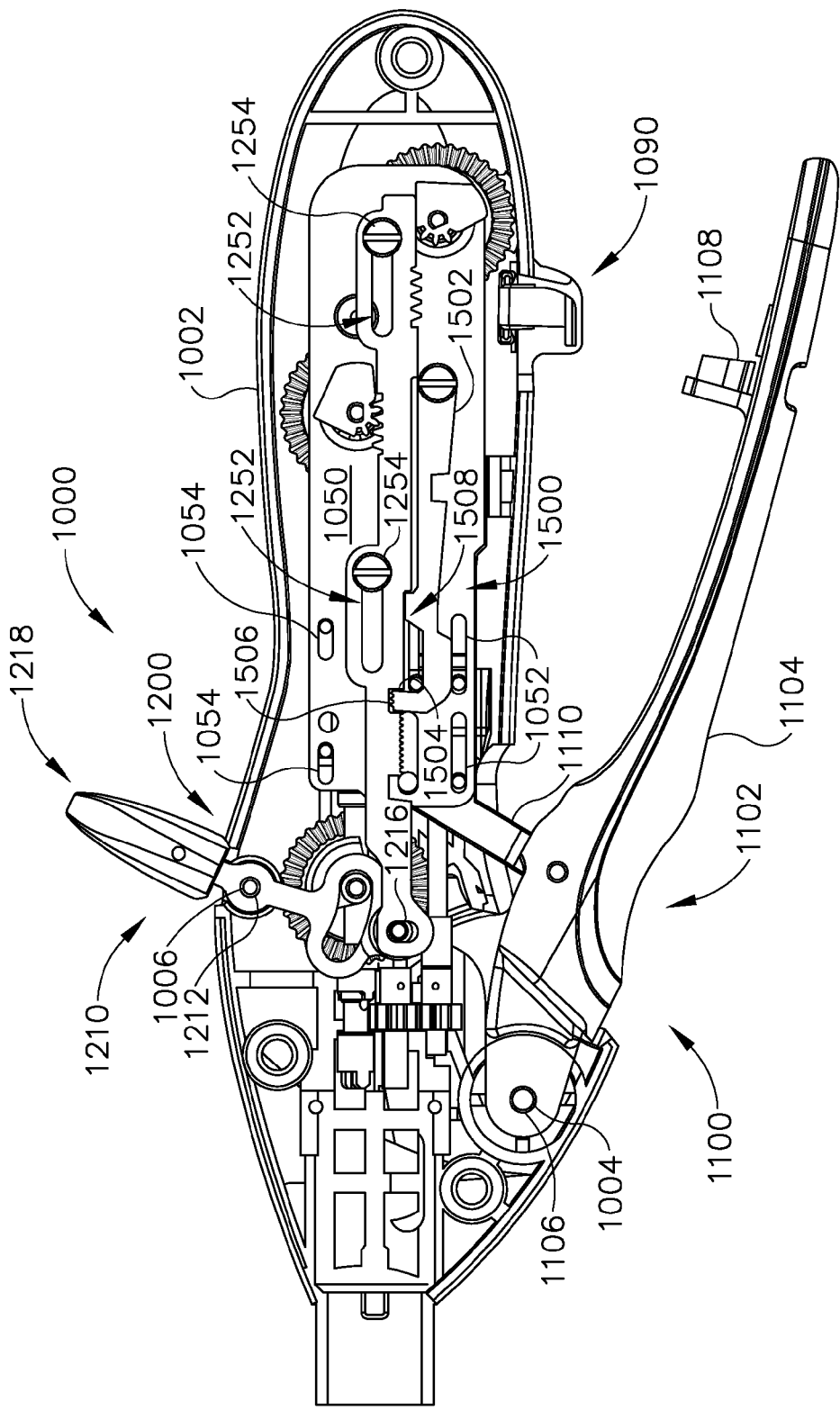
FIG. 16 depicts a side elevation view of an exemplary second handle assembly showing an exemplary trigger-operated actuation assembly and an exemplary toggle actuation assembly.

Similar to the trigger-operated actuation assembly (600) described above, alternative trigger-operated actuation assembly (1100) comprises a trigger (1102), a trigger gear assembly (1120), a clutch assembly (1150), second sheath (280), second drive shaft (284), and a rear drive shaft (1190). As shown in FIG. 16, trigger (1102) is pivotably mounted to a casing (1002) via a pivot (1106) and an axle (1004). Trigger (1102) is pivotable from a first, unactuated position, shown in FIGS. 17A and 18A, to a second, actuated position, shown in FIGS. 17B and 18B.

a. Exemplary Trigger

Figure 17A:
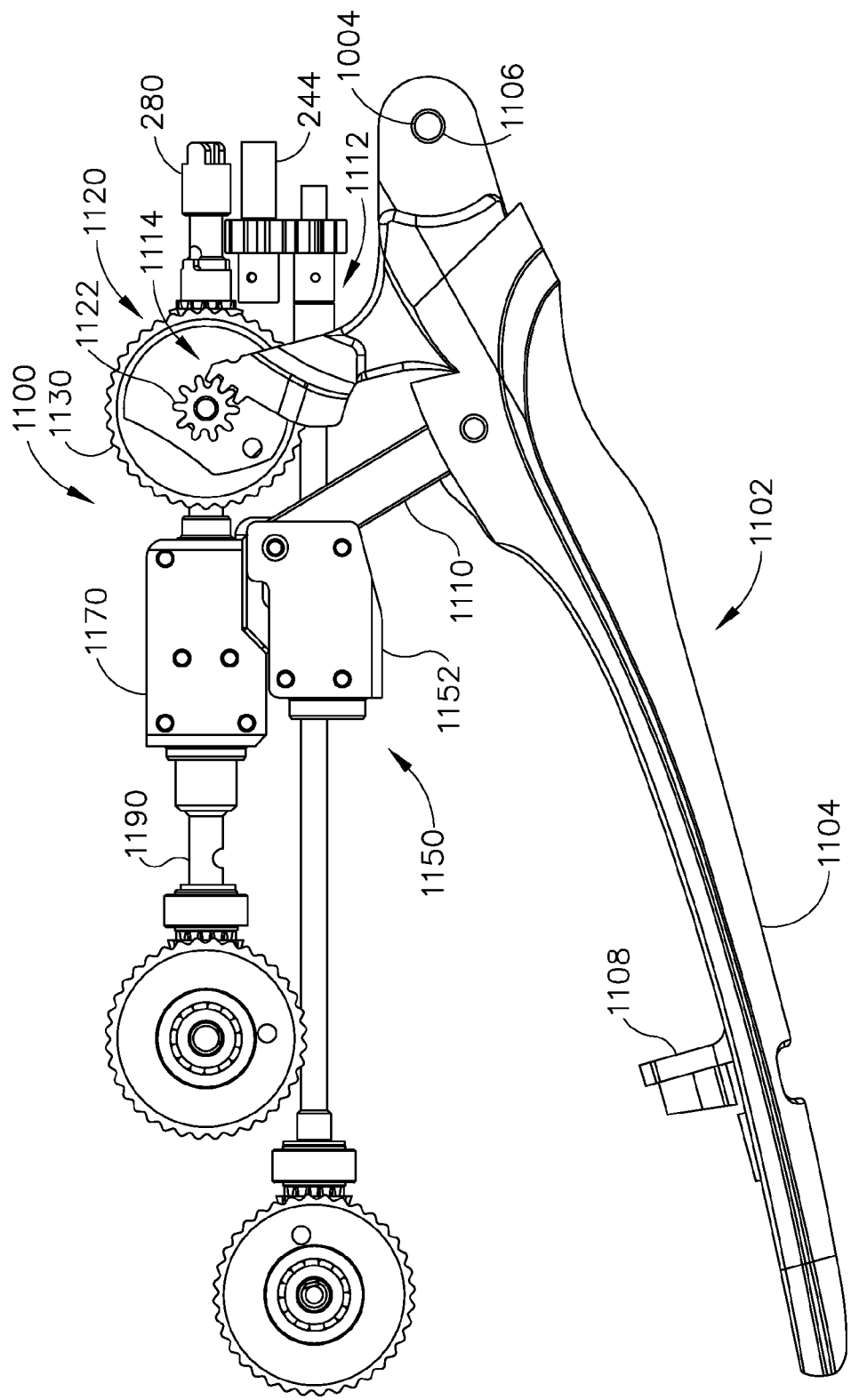
FIG. 17A depicts a reverse side elevation view of the handle assembly of FIG. 16 showing only the trigger-operated actuation assembly in an unactuated position.
Figure 17B:
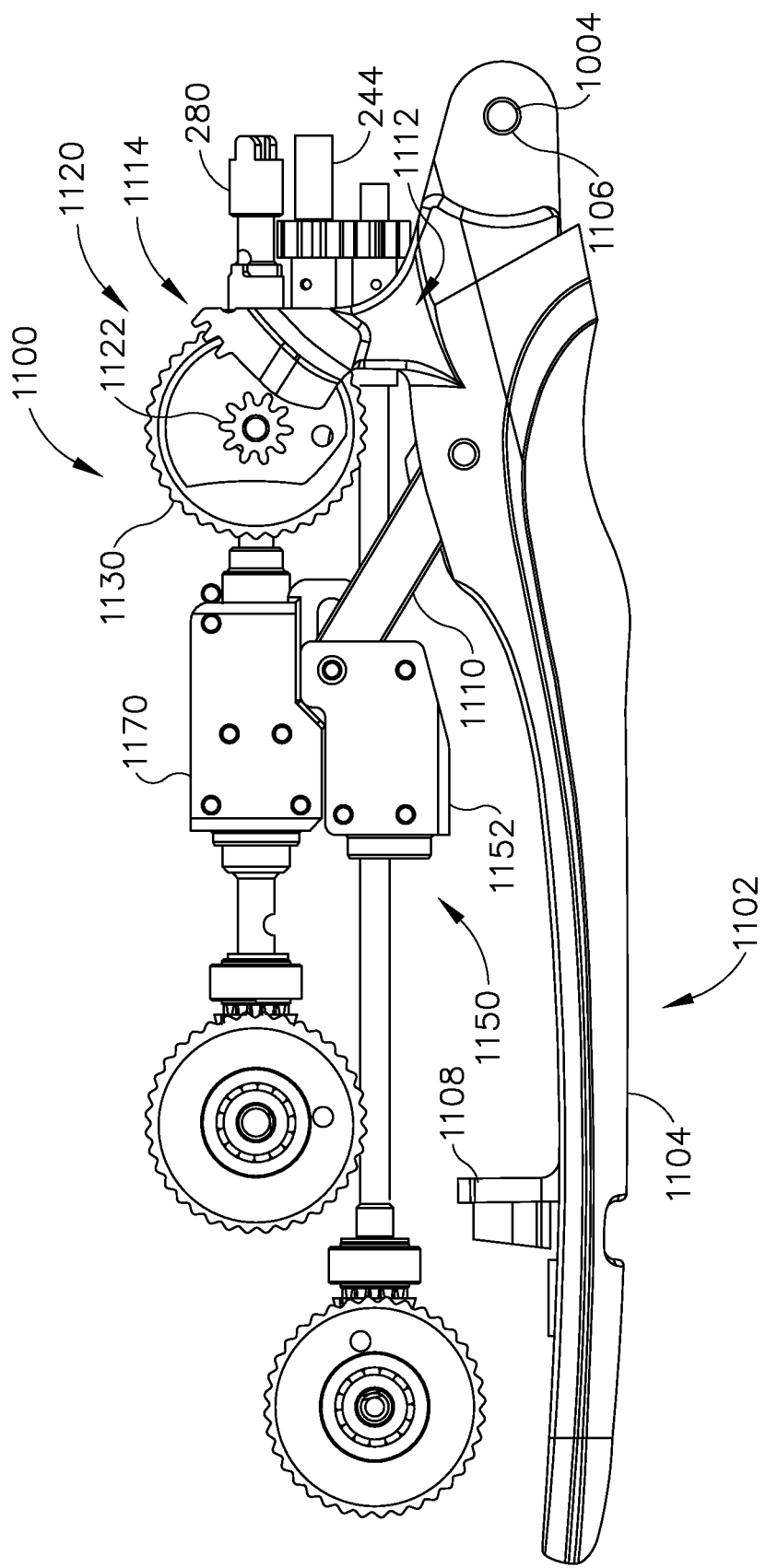
FIG. 17B depicts a reverse side elevation view of the trigger-operated actuation assembly of FIG. 17A shown in an actuated position.

Trigger (1102) of the present example includes a lever (1104), a pivot (1106), a clutch linkage (1110), and a geared member (1112). Lever (1104) comprises a handle capable of being actuated by a hand of a user. A latching member (1108) is located at a proximal end of lever (1104) and is configured to selectively couple to latch (1090) on handle assembly (1000). In the present example, latching member (1108) couples with latch (1090) to secure trigger (1102) relative to handle assembly (1000) when trigger (1102) is pivoted to the second, actuated position. Accordingly, trigger-operated actuation assembly (1100) may be selectively locked in the second, actuated position via latching member (1108). As shown in FIGS. 17A-17B, geared member (1112) extends from lever (1104) and includes teeth (1114) configured to mesh with and engage trigger gear assembly (1120) such that trigger (1102) is operable to rotate trigger gear assembly (1120), as will be described in greater detail below. Clutch linkage (1110) comprises an elongate member that is pivotably coupled to lever (1104) at a first end and to a first clutch member (1152) at a second end such that clutch linkage (1110) is operable to linearly actuate first clutch member (1152) as trigger (1102) is pivoted from the first position to the second position. Clutch linkage (1110) and clutch assembly (1150) will be described in greater detail below. In some versions, trigger (1102) may be resiliently biased by a spring toward the first, unactuated position shown in FIG. 17A. Of course further configurations for trigger (1102) will be apparent to one of ordinary skill in the art in view of the teachings herein.

b. Exemplary Trigger Gear Assembly

Similar to trigger gear assembly (620) described above, trigger gear assembly (1120) is operable to rotate both second sheath (280) and second drive shaft (284) to rotate second grasping arm (250). Accordingly, trigger (1102) is operable to rotate second grasping arm (250) in accordance with the example shown in FIG. 5C. As shown best in FIGS. 18A-18B and 22, trigger gear assembly (1120) comprises a spur gear (1122) and a bevel gear (1130) that are fixedly coupled to a shaft member (1140) such that spur gear (1122) and bevel gear (1130) are rotatably fixed relative to each other. Shaft member (1140) is rotatably mounted to casing (1102) such that shaft member (1140) is rotatable relative to casing (1102). Shaft member (1140) further includes a brake portion (1142) as will be described in greater detail below. As shown in FIGS. 17A-17B, spur gear (1122) meshes with and engages teeth (1114) of geared member (1112) such that the pivoting motion of trigger (1102) rotates trigger gear assembly (1120). Bevel gear (1130) meshes with a second spur gear (1132) that is fixedly coupled to second sheath (280) such that the rotation of bevel gear (1130) rotates second spur gear (1132) and second sheath (280). In the present example, spur gear (1122) and bevel gear (1130) have a ratio of approximately 10:1, inclusive, to approximately 15:1, inclusive. Thus, as trigger (1102) is pivoted, bevel gear (1130) rotates second sheath (280).

It should be understood that in the present example, teeth (1114) are provided such that actuation of trigger (1102) only rotates trigger gear assembly (1120) a predetermined amount (e.g., during only part of the pivotal range of travel of trigger (1102)) such that second grasping arm (250) is pivoted about longitudinal axis (140) as shown in FIGS. 5C, 5D, 5F, and 5G. As shown in FIGS. 17A-17B, there is no engagement of teeth (1114) and spur gear (1122) during part of the range of travel of trigger (1102) that follows the rotation of second grasping arm (250). As will be described in greater detail below, the range of motion where teeth (1114) are no longer engaged with spur gear (1122) corresponds to when clutch linkage (1110) is actuating first clutch member (1152) and second clutch member (1170) proximally relative to a pair of frames (1050). In some versions, spur gear (1122) may comprise a geared portion and one or more cam surfaces, similar to that of first pinion member (1340) and/or second pinion gear (1420) described below. The geared portion may be configured to engage with teeth (1114) for a predetermined angular range while cam surfaces are configured to engage with the flat portion of geared member (1112) once trigger gear assembly (1120) rotates second grasping arm (250) the predetermined amount. Of course other configurations will be apparent to one of ordinary skill in the art in view of the teachings herein.

In the present example, a sheath engagement member (1134) is fixedly coupled to a proximal end of outer sheath (280) and is partially disposed within a distal end of a second clutch member (1170). As will be described below in reference to clutch assembly (1150), a clutch shuttle (1180) (shown in FIGS. 19A-19B) is interiorly engaged with second drive shaft (284) and also engaged at a distal end (1184) with an operative end (1136) of sheath engagement member (1134) in this first, unactuated position such that rotation of second sheath (280) also rotates second drive shaft (284). Thus, as trigger (1102) pivotally engages with and rotates trigger gear assembly (1120), second sheath (280) and second drive shaft (284) are simultaneously rotated to rotate second grasping arm (250) about longitudinal axis (140), as shown and described in reference to FIGS. 5C and 5F. If trigger (1102) is released, second grasping arm (250) is rotated back, such as that shown and described in reference to FIGS. 5D and 5G.

Figure 18A:
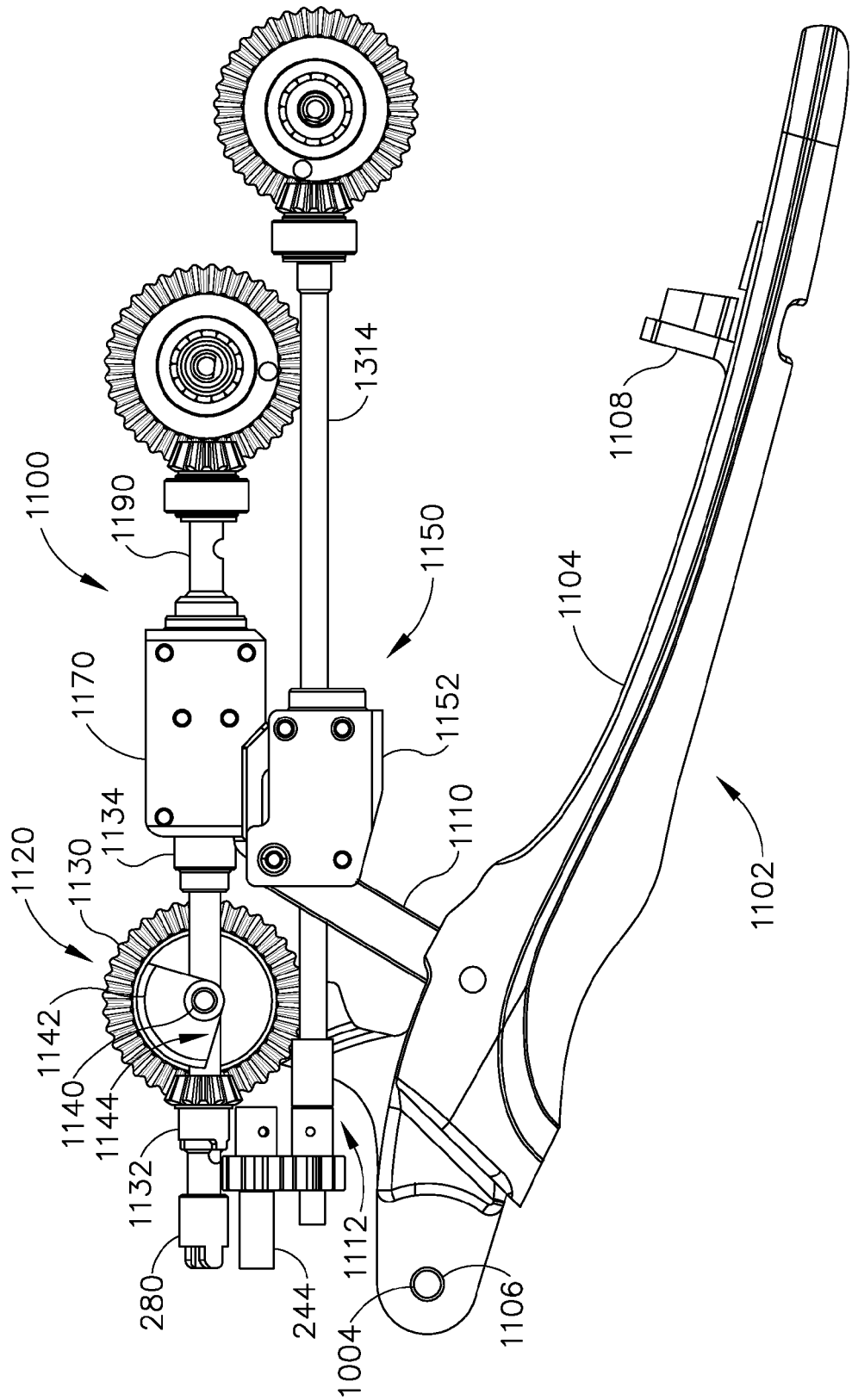
FIG. 18A depicts a side elevation view of the trigger-operated assembly of FIG. 17A shown in an unactuated position.
Figure 18B:
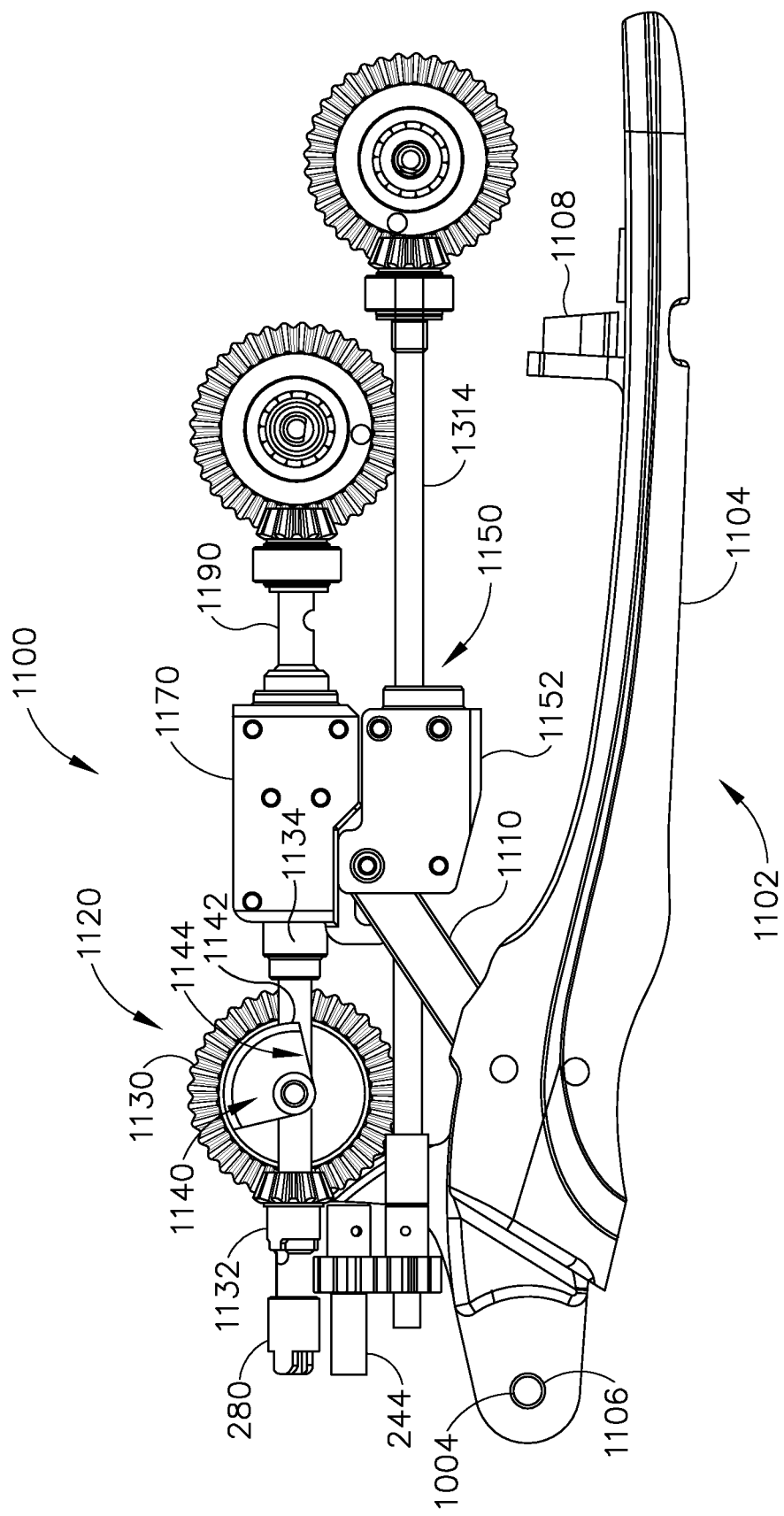
FIG. 18B depicts a side elevation view of the trigger-operated assembly of FIG. 18A shown in an actuated position.
Figure 22:
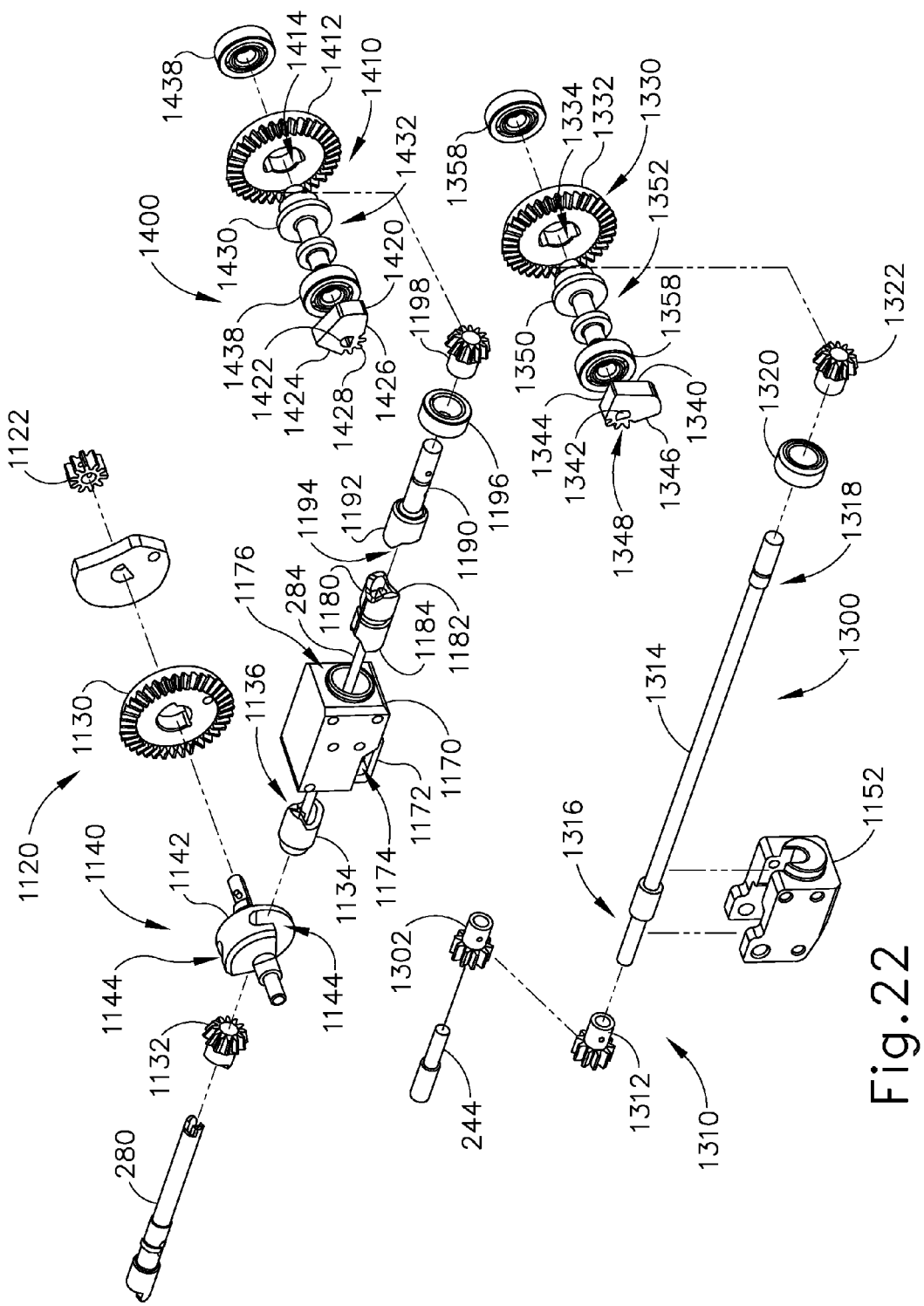
FIG. 22 depicts an exploded view of the drive trains of the trigger-operated actuation assembly and the toggle actuation assembly of FIG. 16.

FIGS. 18A-18B depict the opposing side of trigger gear assembly (1120) showing brake portion (1142) of shaft member (1140) disposed about second sheath (280). Referring briefly to FIG. 22, brake portion (1142) comprises a pair of U-shaped channels (1144) configured to fit around and resist rotation of second sheath (280). In some versions, a frictional material may be disposed in channels (1144) to frictionally resist rotation of second sheath (280). As shown in FIG. 18A, when trigger (1102) is in the first, unactuated position, a first channel (1144) of brake portion (1142) is substantially engaged with sheath (280) such that rotation of sheath (280) is resisted by brake portion (1142). As trigger (1102) is pivoted, and therefore trigger gear assembly (1120) is rotated clockwise relative to that shown in FIG. 18A, shaft member (1140) is rotated to disengage brake portion (1142) and permit rotation of second sheath (280) via bevel gear (1130). As trigger gear assembly (1120) is rotated, a second channel (1144) engages second sheath (280) to resist rotation of second sheath (280) after the rotation imparted by bevel gear (1130). Of course other camming features and cam surfaces, latches, locks, or other features for resisting rotation of sheath (280) will be apparent to one of ordinary skill in the art in view of the teachings herein.

c. Exemplary Clutch Assembly

Figure 19A:
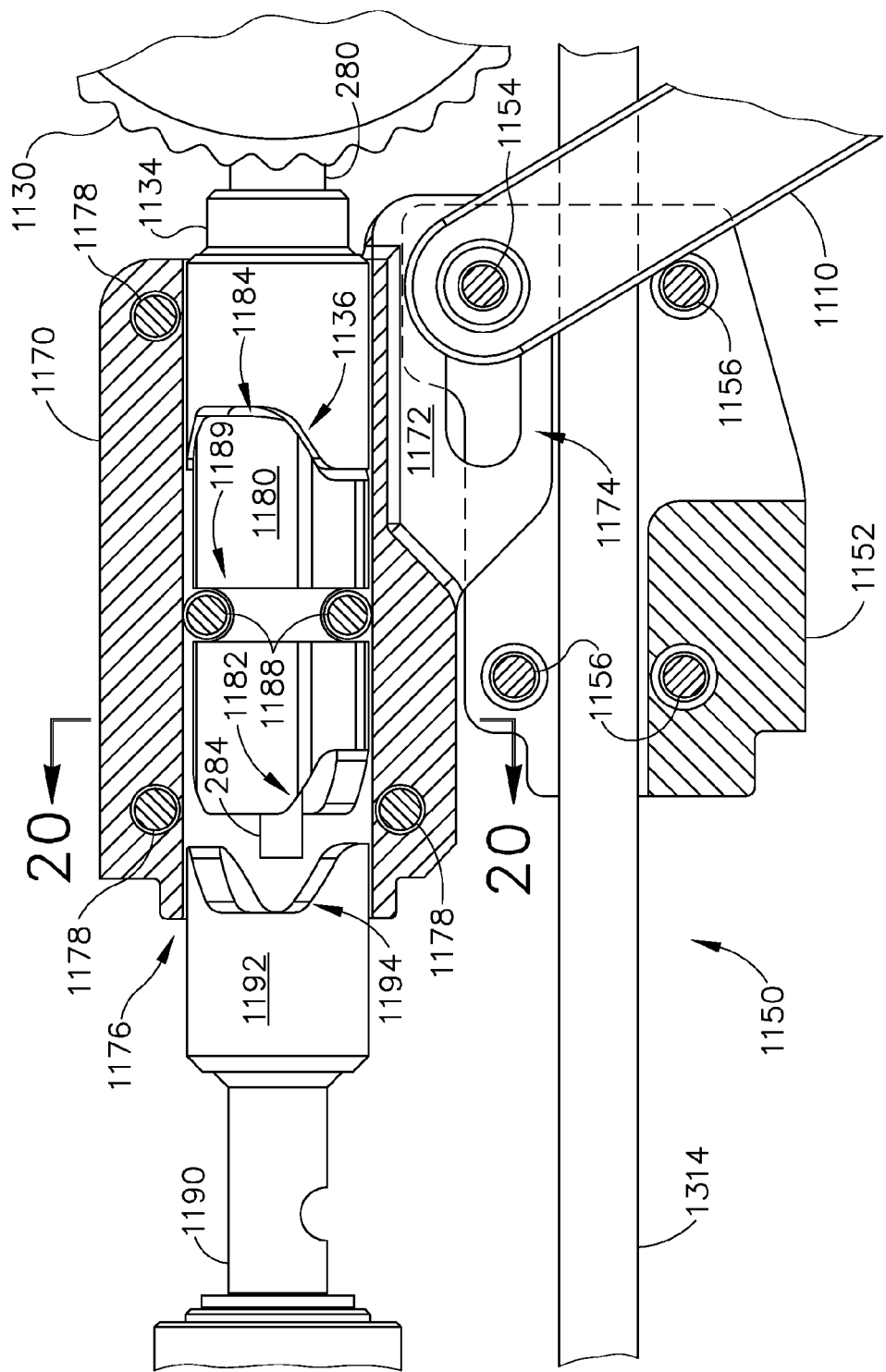
FIG. 19A depicts an enlarged partial cross-sectional view of an exemplary clutch assembly of the trigger-operated assembly of FIG. 17A shown in an unactuated position.
Figure 19B:
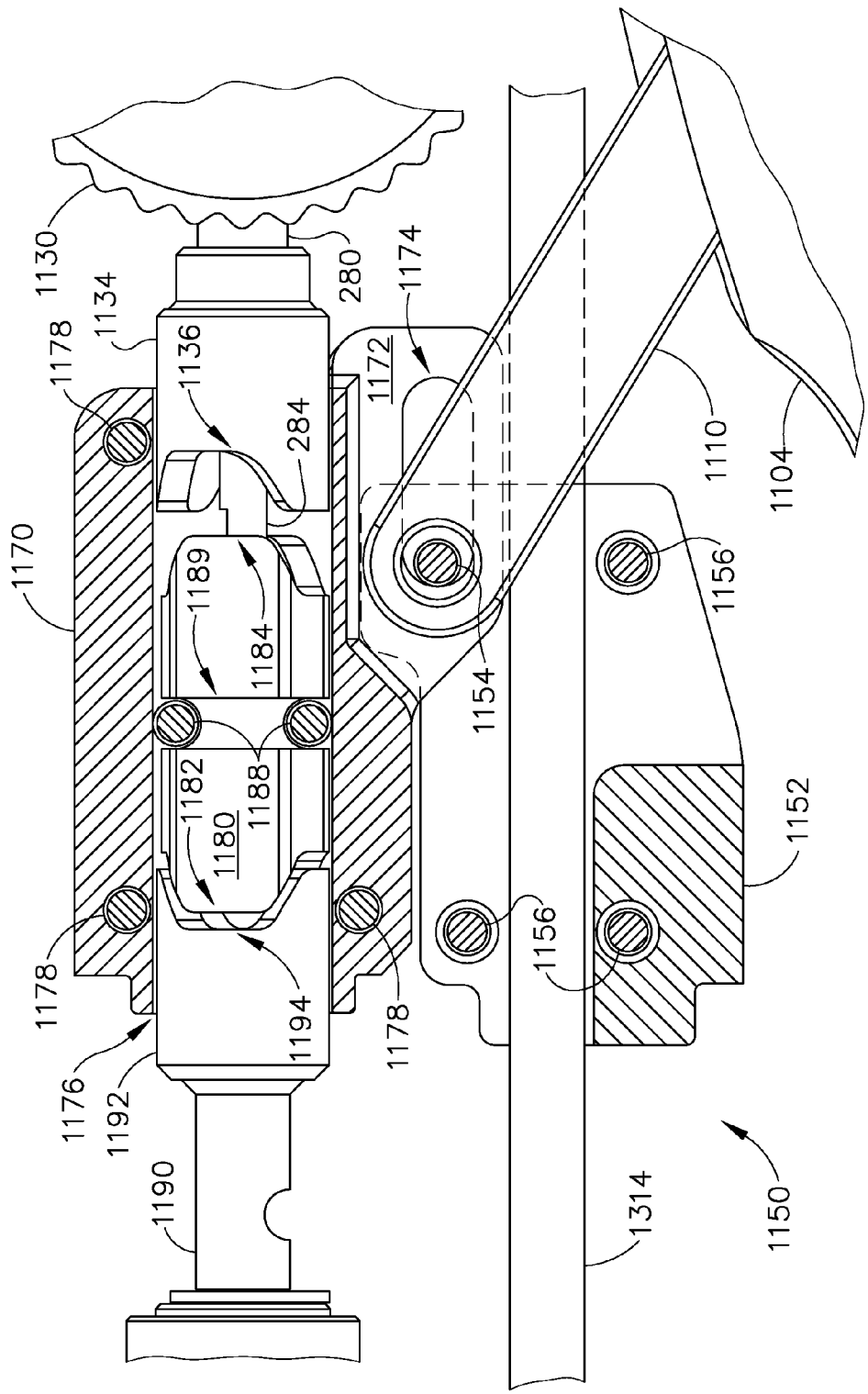
FIG. 19B depicts an enlarged partial cross-sectional view of the clutch assembly of FIG. 19A shown in an actuated position.

FIGS. 19A-19B depict a partial cross-sectional view of an exemplary clutch assembly (1150) of trigger-operated actuation assembly (1100). Clutch assembly (1150) comprises a first clutch member (1152), a second clutch member (1170), a clutch shuttle (1180), sheath engagement member (1134) fixedly coupled to second sheath (280), and a rear shaft engagement member (1192) fixedly coupled to rear drive shaft (1190). As shown best in FIG. 20, first clutch member (1152) comprises a longitudinally actuatable member slidably disposed about a transfer axle (1314) of toggle actuation assembly (1200). First clutch member (1152) is pivotably coupled to a first end of clutch linkage (1110) by a coupling pin (1154). Coupling pin (1154) of the present example is disposed within a longitudinal slot (1174) of second clutch member (1170) and permits first clutch member (1152) to slide proximally a predetermined distance relative to second clutch member (1170) as trigger (1102) is pivoted from the first, unactuated position. In the present example, the predetermined distance corresponds to the predetermined amount of rotation of trigger (1102) that rotates second grasping arm (250) about longitudinal axis (140) until teeth (1114) disengage from spur gear (1122), as described above. After this predetermined distance, first clutch member (1152) engages with second clutch member (1170) to slide clutch shuttle (1180), as will be described in greater detail below. Additional pins (1156) extend transversely through first clutch member (1152) and are inserted into longitudinal slots (1052) formed in a pair of frames (1050) (shown in FIG. 16) to restrict the movement of first clutch member (1152) to the longitudinal direction. In some versions, frames (1050) may be omitted and longitudinal tracks may be formed in casing (1002).

Second clutch member (1170) of the present example is positioned above first clutch member (1152) and is associated with first clutch member (1152) via a slotted portion (1172) having longitudinal slot (1174). As noted above, coupling pin (1154) is inserted transversely through longitudinal slot (1174). Thus, when coupling pin (1154) reaches the proximal end of slot (1174), coupling pin (1154) and clutch linkage (1110) are operable to actuate second clutch member (1170) proximally. In the present example, longitudinal slot (1174) has a longitudinal length that is sized to correspond to the predetermined distance described above such that coupling pin (1154) engages and actuates second clutch member (1170) after second grasping arm (250) is rotated via trigger gear assembly (1120). Of course this is merely optional and longitudinal slot (1174) may have other lengths and/or may simply be a coupling point. Second clutch member (1170) further includes a central longitudinal bore (1176). As shown in FIGS. 19A-19B, bore (1176) is sized to receive clutch shuttle (1180) therein as well as operative ends (1136, 1194) of engagement members (1134, 1192). In the present example, second clutch member (1170) is longitudinally slidably mounted to frames (1050) via transverse pins (1178) disposed in slots (1054) formed through frames (1050). Of course, as noted above, frames (1050) may be omitted and longitudinal slots may be formed in casing (1002).

Figure 20:
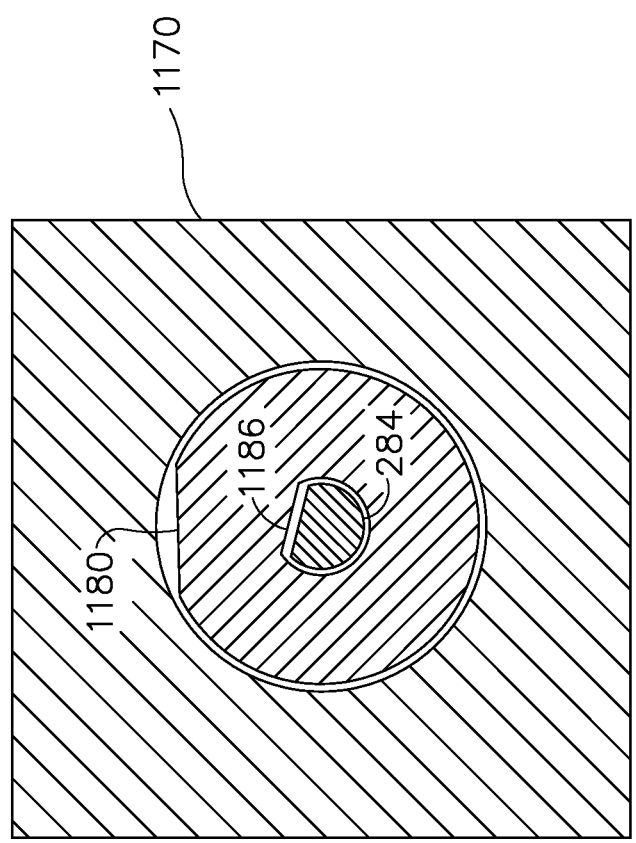
FIG. 20 depicts cross-sectional view of an exemplary clutch shuttle of FIG. 19A taken along section line 20-20 in FIG. 19A.

Clutch shuttle (1180) of the present example comprises a proximal end (1182), a distal end (1184), a D-shaped central bore (1186) (shown in FIG. 20), and a middle annular recess (1189). Clutch shuttle (1180) is disposed within bore (1176) of second clutch member (1170) and is longitudinally secured relative to second clutch member (1170) via the combination of a pair of transverse shuttle pins (1188) and a middle annular recess (1189). As shown in FIGS. 19A-19B, while transverse shuttle pins (1188) and middle annular recess (1189) secure clutch shuttle (1180) longitudinally, it should be understood that clutch shuttle (1180) is rotatable about its longitudinal axis within second clutch member (1170). FIG. 20 depicts a cross-section of clutch shuttle (1180) showing D-shaped central bore (1186) and a keyed portion (285) of second drive shaft (284) inserted therein. Thus, when clutch shuttle (1180) is rotated, second drive shaft (284) is also rotated as keyed portion (285) and D-shaped central bore (1186) engage each other. In addition, it should be understood that clutch shuttle (1180) of the present example is longitudinally actuatable along keyed portion (285) while remaining engaged with second drive shaft (284). Accordingly, when second clutch member (1170) is actuated proximally via first clutch member (1152), clutch shuttle (1180) remains engaged with second drive shaft (284). In other words, clutch shuttle (1180) is engaged with second drive shaft (284) throughout the entire range of travel of trigger (1102).

Distal end (1184) of clutch shuttle (1180) is configured to rotatably engage with operative end (1136) of sheath engagement member (1134) such that clutch shuttle (1180) is rotatable with sheath engagement member (1134) (and therefore second sheath (280)). By way of example only, distal end (1184) has a pair of tabs that engage with corresponding recesses of sheath engagement member (1134). In some versions, distal end (1184) and sheath engagement member (1134) may include spline features to rotatably engage. Similar to distal end (1184), proximal end (1182) of clutch shuttle (1180) is likewise configured to rotatably engage with operative end (1194) of rear shaft engagement member (1192) such that clutch shuttle (1180) is rotatable with rear shaft engagement member (1192) (and therefore rear drive shaft (1190)). By way of example only, proximal end (1182) has a pair of tabs that engage with corresponding recesses of rear shaft engagement member (1192). In some versions, proximal end (1182) and rear shaft engagement member (1192) may include spline features to rotatably engage. Of course further configurations for clutch shuttle (1180) will be apparent to one of ordinary skill in the art in view of the teachings herein.

Referring back to FIG. 19A, when clutch shuttle (1180) is in a first, unactuated position, distal end (1184) of clutch shuttle (1180) is rotatably engaged with operative end (1136) of sheath engagement member (1134) such that rotation of second sheath (280) also rotates second drive shaft (284) when trigger gear assembly (1120) is rotated. Accordingly, as noted above, trigger gear assembly (1120) and clutch shuttle (1180) rotate both second sheath (280) and second drive shaft (284) substantially simultaneously when trigger (1102) is pivoted through a first range of travel, thereby resulting in second grasping arm (250) rotating in accordance with that shown in FIGS. 5C, 5D, 5F, and 5G. As trigger (1102) is pivoted through the first range of travel, clutch linkage (1110) of the present example longitudinally actuates first clutch member (1152) while coupling pin (1154) slides within longitudinal slot (1174) of second clutch member (1170). Once coupling pin (1154) abuts a proximal end of longitudinal slot (1174), continued pivoting of trigger (1102) through a second range of travel causes clutch linkage (1110) to actuate second clutch member (1170) with first clutch member (1152). As shown in the sequence shown in FIGS. 19A-19B, the actuation of second clutch member (1170) disengages distal end (1184) of clutch shuttle (1180) from sheath engagement member (1134) and engages proximal end (1182) of clutch shuttle (1180) with rear shaft engagement member (1192). Thus, second sheath (280) is substantially disengaged from clutch shuttle (1180) and rear drive shaft (1190) is substantially engaged with clutch shuttle (1180) during the second range of travel of trigger (1102). As shown in FIG. 19B, second drive shaft (284) is rotatably engaged with rear drive shaft (1190) via clutch shuttle (1180) and is no longer rotatably engaged with second sheath (280). In this configuration, grasping arms (210, 250) may then be actuated by toggle actuation assembly (1200) to transfer the grip of needle (50) from one arm (210, 250) to the other. Still other constructions for trigger-operated actuation assembly (1100) will be apparent to one of ordinary skill in the art in view of the teachings herein.

ii. Exemplary Alternative Toggle Actuation Assembly

As described above, once second grasping arm (250) is in the rotational position depicted in FIG. 5C, it may be desirable to transfer control of needle (50) from first grasping arm (210) to second grasping arm (250), as shown and described in reference to FIGS. 5C-5D. To do so, jaws (260, 270) of second grasping arm (250) are closed about a portion of needle (50) and jaws (220, 230) of first grasping arm (210) are opened to release needle (50). To accomplish this, first drive shaft (244) is rotated in a first direction and second drive shaft (284) is rotated in a second direction, opposite the first direction. In some versions, second drive shaft (284) is rotated first to grasp needle (50) with second grasping arm (250) while first grasping arm (210) still grasps needle (50). Once second grasping arm (250) has closed or substantially closed to grasp needle (50), first drive shaft (244) is rotated to release needle (50) from the grasp of first grasping arm (210). Accordingly, needle (50) in is always grasped by at least one arm (210, 250) or the other (210, 250) throughout the transfer. Similarly to toggle actuation assembly (700), toggle actuation assembly (1200) is provided within handle assembly (1000) to operate first drive shaft (244) and second drive shaft (284) to transfer needle (50) from one arm (210, 250) to the other (210, 250). Of course it should be understood that toggle actuation assembly (1200), when reversed from the below description, can transfer needle (50) in the opposite direction.

Figure 21A:
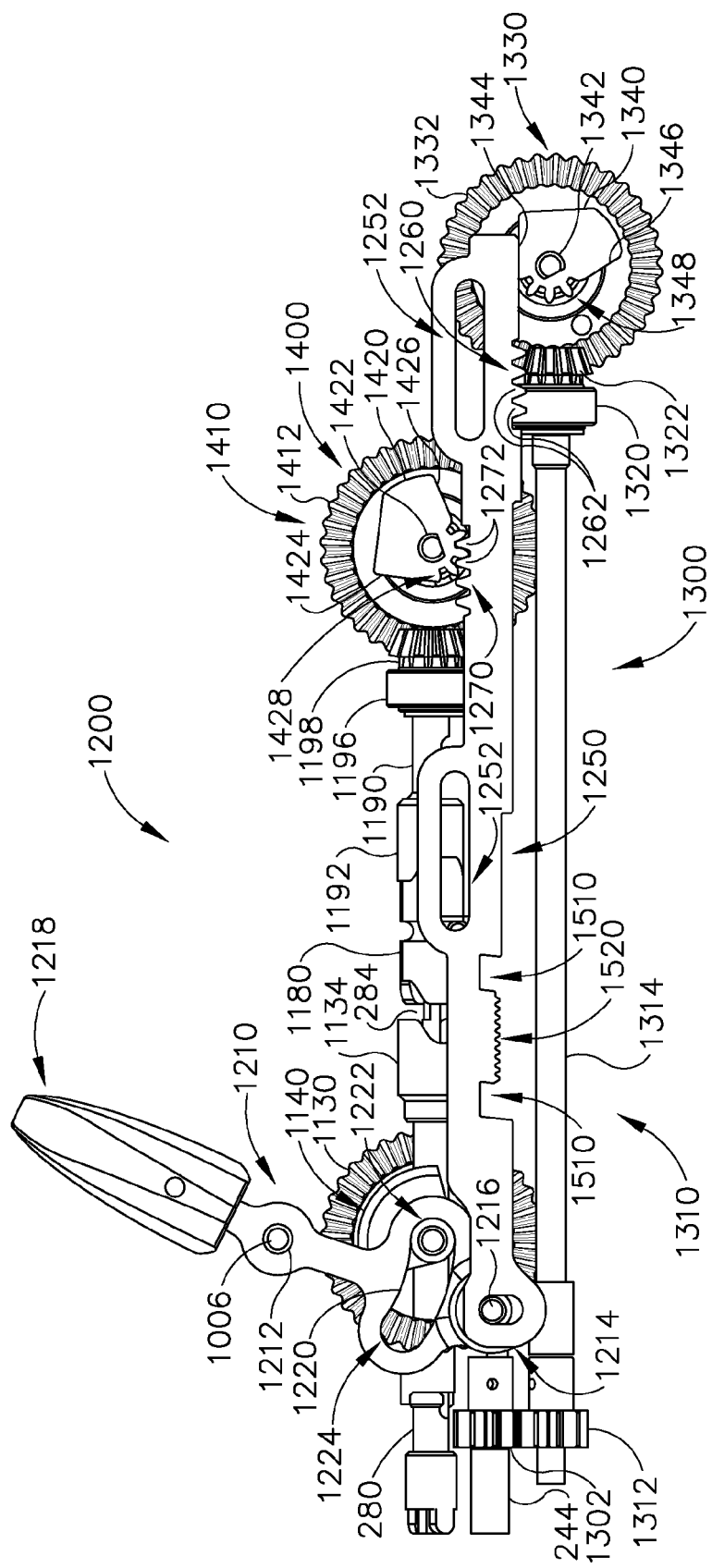
FIG. 21A depicts a side elevation view of the handle assembly of FIG. 16 showing only the toggle actuation assembly shown in a first position.

FIGS. 16 and 21A-23 depict an exemplary alternative toggle actuation assembly (1200) within handle assembly (1000). In FIGS. 21A-21C, portions of trigger-operated actuation assembly (1100) has been omitted for clarity purposes only. Toggle actuation assembly (1200) of the present example comprises a toggle (1210), a rack (1250), a first drive train (1300), and a second drive train (1400).

a. Exemplary Toggle and Rack

Toggle (1210) is pivotably mounted to casing (1002) via axle (1006) and pivot (1212) and is operable to longitudinally actuate rack (1250) relative to first drive train (1300) and second drive train (1400). Toggle (1210) is rotatably coupled at a first end (1214) to rack (1250) via a pin (1216) and is operable by a user at a second end (1218) that protrudes from casing (1002), as shown in FIG. 16. Toggle (1210) of the present example further includes an arcuate slot (1220) that is configured to permit a portion of shaft member (1140) therethrough. In the present example, arcuate slot (1220) is sized such that a proximal end (1222) and distal end (1224) limit the range of motion of toggle (1210) to that shown in FIGS. 21A-21C.

Rack (1250) of the present example comprises a longitudinally extending member having a first rack gear section (1260) and a second rack gear section (1270). As shown in FIG. 16, a pair of screws (1254) couple to frame (1050) and are slidingly received in longitudinal slots (1252) to limit rack (1250) to longitudinal motion within handle assembly (1000). Rack (1250) of the present example further includes a pair of notches (1510) and teeth (1520) configured to engage with a locking feature (1500), as will be described in greater detail below.

In the present example, first rack gear section (1260) comprises a plurality of teeth (1262) and is oriented downwardly to engage first drive train (1300). Second rack gear section (1270) also comprises a plurality of teeth (1272) and is oriented upwardly to engage second drive train (1400). Second rack gear section (1270) is positioned distal of first rack gear section (1260) such that second rack gear section (1270) engages second drive train (1400) followed by first rack gear section (1260) engaging first drive train (1300) when rack (1250) is actuated distally by toggle (1210). In this arrangement, second rack gear section (1270) is operable to rotate second drive shaft (284) via second drive train (1400), described in greater detail below, to cause second grasping arm (250) to grip needle (50) prior to first rack gear section (1260) rotating first drive shaft (244) via first drive train (1300), described in greater detail below, to cause first grasping arm (210) to release needle (50). In some versions, second rack gear section (1270) and first rack gear section (1260) may be positioned to simultaneously rotate second drive shaft (284) and first drive shaft (244). In some other versions, second rack gear section (1270) and first rack gear section (1260) may be positioned to initially rotate second drive shaft (284) and subsequently rotate first drive shaft (244) while second drive shaft (284) is still rotating. Of course further configurations for rack (1250) and/or toggle (1210) and/or drive shaft (244, 284) rotation timing will be apparent to one of ordinary skill in the art in view of the teachings herein.

b. Exemplary First Drive Train

First drive train (1300) is operable to rotate first drive shaft (244) when first rack gear section (1260) engages first drive train (1300). As shown best in FIG. 22, first drive train (1300) of the present example comprises a first spur gear (1302), a transfer axle assembly (1310), and a first gear assembly (1330). First spur gear (1302) is fixedly coupled to first drive shaft (244) and is configured to mesh with and engage second spur gear (1312) of transfer axle assembly (1310).

Figure 21B:
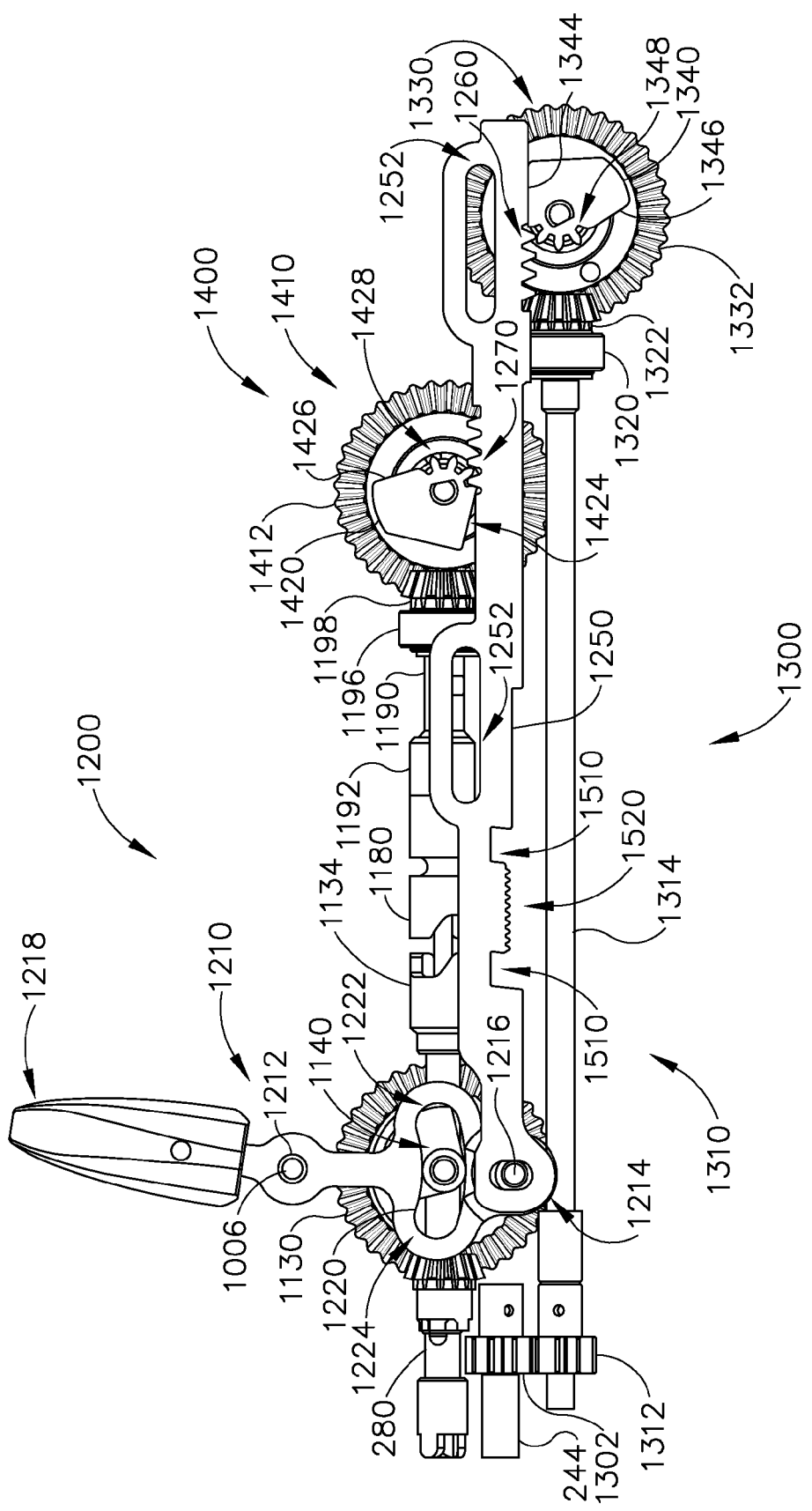
FIG. 21B depicts a side elevation view of the toggle actuation assembly of FIG. 21A shown in a second position.
Figure 21C:
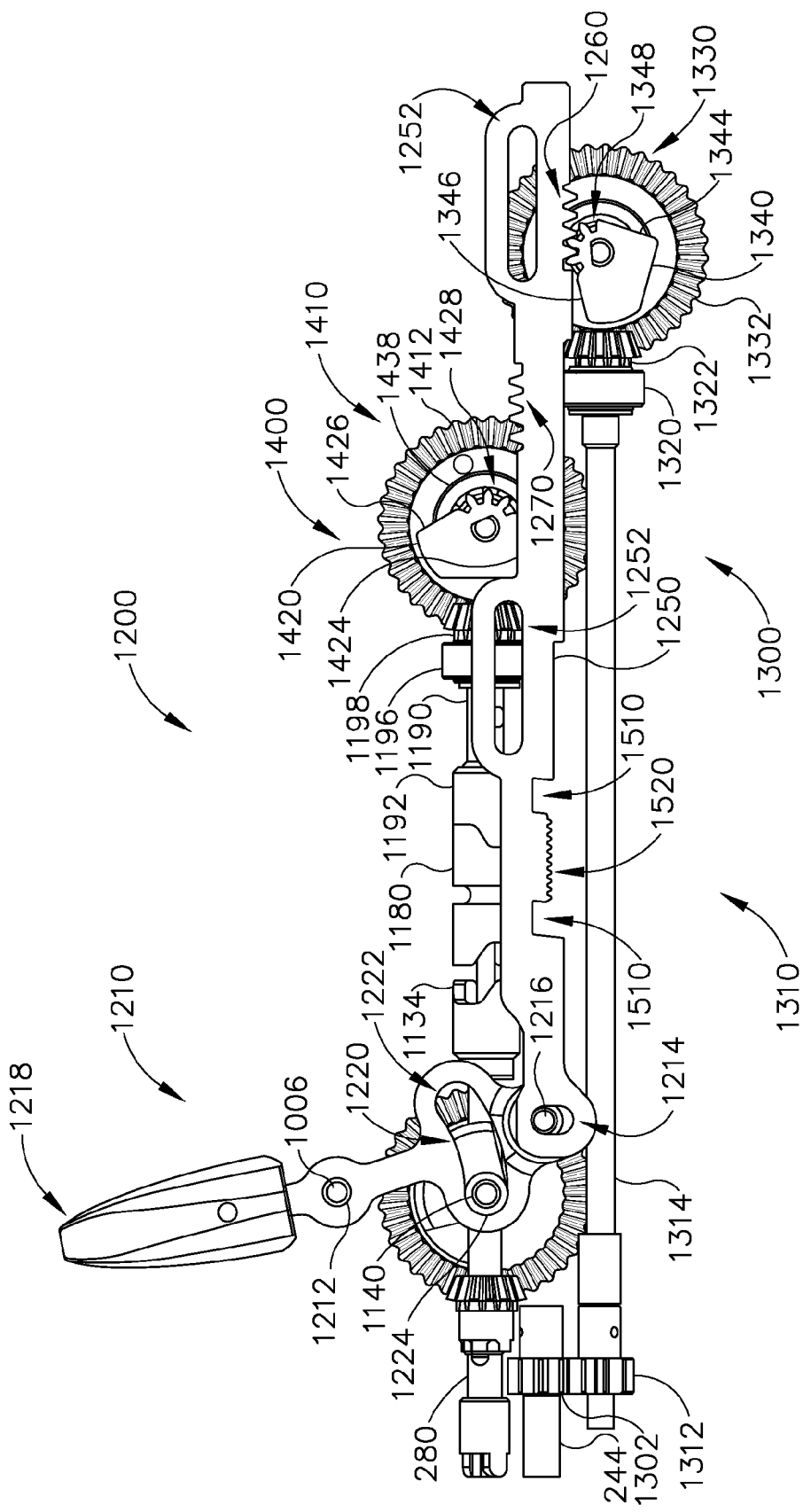
FIG. 21C depicts a side elevation view of the toggle actuation assembly of FIG. 21A shown in a third position.

Transfer axle assembly (1310) comprises second spur gear (1312), a transfer axle (1314), a bearing (1320), and a first rear bevel gear (1322). In the present example, transfer axle assembly (1310) is rotatably supported by bearing (1320) at a proximal end (1318) of transfer axle (1314) and by first clutch member (1152) near distal end (1316) of transfer axle (1314). Second spur gear (1312) is fixedly coupled to distal end (1316) and, in the present example, lies in the same vertical plane as first spur gear (1302), as shown in FIGS. 21A-21C. In some versions transfer axle assembly (1310) may be offset from the vertical plane in which second drive shaft (244) lies, yet still is engaged with first spur gear (1302). Transfer axle (1314) terminates at its proximal end (1318) with first rear bevel gear (1322) fixedly coupled thereto. First rear bevel gear (1322) is configured to mesh with and engage first bevel gear (1332) of first gear assembly (1330).

Referring to FIG. 22, first gear assembly (1330) comprises a first bevel gear (1332) and a first pinion member (1340) that are rotatably coupled together via a common shaft member (1350). First bevel gear (1332) is rotatably coupled to a first end of shaft member (1350) via a keyed central opening (1334) in first bevel gear (1332). First pinion member (1340) is likewise rotatably coupled to a second end of shaft member (1350) via a keyed opening (1342). In the present example, shaft member (1350) is rotatably mounted to handle assembly (1000) by a pair of bearings (1358). Shaft member (1350) also includes a central spacing portion (1352) to accommodate first rear bevel gear (1322) without interference from rack (1250) and/or first pinion member (1340). Referring to FIGS. 21A-21C, first pinion member (1340) comprises a geared portion (1348), a first surface (1344), and a second surface (1346). As shown in FIG. 21A, first surface (1344) comprises a flat surface that slides along a corresponding flat surface of rack (1250) as toggle (1210) is initially actuated. As shown in FIG. 21B, geared portion (1348) is configured to engage with first rack gear section (1260) such that actuation of rack (1250) rotates first gear assembly (1330), which in turn rotates first drive shaft (244), thereby opening or closing jaws (220, 230) of first grasping arm (210), described in greater detail above. At the rotational end of geared portion (1348), second surface (1346) includes a flat surface that abuts rack (1250) at the end of the range of motion of toggle (1210) as shown in FIG. 21C. It should be understood that the engagement of first surface (1344) with rack (1250) and the engagement of second surface (1346) with rack (1250) substantially prevent rotation of first gear assembly (1330), thereby substantially locking the rotational position of first drive shaft (244) relative to first sheath (240). In some versions, first surface (1344) and/or second surface (1346) may be sized or configured to frictionally or otherwise lock against rack (1250) when toggle actuation assembly (1200) is pivoted to the positions shown in FIGS. 21A and/or 21C. In addition, or in the alternative, the locking of first surface (1344) and/or second surface (1346) against rack (1250) may provide tactile feedback through toggle (1210). The specific operation of first drive train (1300) will be described in greater detail below. While one merely exemplary configuration for first drive train (1300) has been described, still further configurations and assemblies for first drive train (1300) will be apparent to one of ordinary skill in the art in view of the teachings herein.

c. Exemplary Second Drive Train

Second drive train (1400) comprises rear drive shaft (1190), described above, and a second gear assembly (1410). As described above, rear drive shaft (1190) is fixedly coupled to rear shaft engagement member (1192) at a distal end that extends into bore (1176) of second clutch member (1170). As shown in FIG. 22, a bearing (1196) rotatably supports rear drive shaft (1190). A second rear bevel gear (1198) is fixedly coupled to a proximal end of rear drive shaft (1190) and is configured to engage with second gear assembly (1410) such that rotation imparted by second gear assembly (1410) rotates rear drive shaft (1190) (and consequently second drive shaft (284) when clutch shuttle (1180) is engaged).

Second gear assembly (1410) comprises a second bevel gear (1412) and a second pinion member (1420) that are rotatably coupled together via a common shaft member (1430). Similar to first gear assembly (1330), second bevel gear (1412) is rotatably coupled to a first end of shaft member (1430) via a keyed central opening (1414) in second bevel gear (1412). Second pinion member (1420) is likewise rotatably coupled to a second end of shaft member (1430) via a keyed opening (1422). In the present example, shaft member (1430) is rotatably mounted to handle assembly (1000) by a pair of bearings (1438). Shaft member (1430) also includes a central spacing portion (1432) to accommodate second rear bevel gear (1198) without interference from rack (1250) and/or second pinion member (1420). Similar to first pinion member (1340), second pinion member (1420) comprises a geared portion (1428), a first surface (1424), and a second surface (1426). As shown in FIG. 21A, second surface (1426) comprises a flat surface that abuts rack (1250) at the end of the range of motion of toggle (1210). As shown in FIG. 21B, geared portion (1428) is configured to engage with second rack gear section (1270) such that actuation of rack (1250) rotates second gear assembly (1410), which in turn rotates second drive shaft (284), thereby opening or closing jaws (260, 270) of second grasping arm (250), described in greater detail above. At the rotational end of geared portion (1428), first surface (1424) includes a flat surface that slides along a corresponding flat surface of rack (1250) as toggle (1210) continues to actuate, as shown in FIG. 21C. It should be understood that the engagement of first surface (1424) with rack (1250) and the engagement of second surface (1426) with rack (1250) substantially prevent rotation of second gear assembly (1400), thereby substantially locking the rotational position of second drive shaft (284) relative to second sheath (280). In some versions, first surface (1424) and/or second surface (1426) may be sized or configured to frictionally or otherwise lock against rack (1250) when toggle actuation assembly (1200) is pivoted to the positions shown in FIGS. 21A and/or 21C. In addition, or in the alternative, the locking of first surface (1424) and/or second surface (1426) against rack (1250) may provide tactile feedback through toggle (1210). The specific operation of second drive train (1400) will be described in greater detail below. While one merely exemplary configuration for second drive train (1400) has been described, still further configurations and assemblies for second drive train (1400) will be apparent to one of ordinary skill in the art in view of the teachings herein.

d. Exemplary Operation of Toggle Actuation Assembly

Once clutch shuttle (1180) has engaged rear drive shaft (1190) with second drive shaft (284), a user actuates toggle (1210) to transfer needle (50) from first grasping arm (210) to second grasping arm (250), as shown and described in reference to FIGS. 5C-5D. In the present example, toggle (1210) is initially in a forward position, shown in FIG. 21A, such that rack sections (1260, 1270) are positioned proximally of pinion members (1340, 1420). In this position, jaws (260, 270) of second grasping arm (250) are in an open position and disposed about needle (50). Jaws (220, 230) of first grasping arm (210) are in a closed position and grasp needle (50) with first grasping arm (210). As noted above, the engagement of first surface (1344) of first pinion gear (1340) with rack (1250) provides a positive lock to securely hold jaws (220, 230) in the closed position while rack (1250) is in the longitudinal position shown in FIG. 21A. As toggle (1210) is pivoted rearwardly, shown in FIG. 21B, initially second rack section (1270) engages second pinion member (1420) to rotate rear drive shaft (1190). The rotation of rear drive shaft (1190) is transferred through clutch shuttle (1180) to second drive shaft (284) when clutch shuttle (1180) is engaged with rear shaft engagement member (1192). It should be noted that second sheath (280) remains rotationally fixed in place at this stage by channel (1144) engaged with second sheath (280). Thus, as toggle (1210) is pivoted, second drive shaft (284) is rotated relative to second sheath (280) to close second grasping arm (250) to grasp needle (50). As shown in FIG. 21B, first surface (1344) remains engaged with rack (1250) throughout the rotation of second drive shaft (284) such that jaws (220, 230) remain in the closed position about needle (50) at this stage. It should be understood that in the present example there is a point where both first surface (1344) of first pinion gear (1340) and first surface (1424) of second pinion gear (1420) are both engaged with rack (1250) to lock both jaws (220, 230) of first grasping arm (210) and jaws (260, 270) of second grasping arm (250) about needle (50).

As toggle (1210) continues to be pivoted rearwardly, as shown in FIG. 21C, first rack section (1260) eventually engages first pinion member (1340) to disengage first surface (1344) and to rotate transfer axle (1314). It should be understood that first surface (1424) of second pinion gear (1420) remains positively locked against rack (1250) such that needle (50) remains grasped by jaws (260, 270) of second grasping arm (250). As rack section (1260) engages first pinion member (1340), second spur gear (1312) of transfer axle (1314) engages with spur gear (1302) to rotate first drive shaft (244) while first sheath (240) is fixed in place relative to casing (1002). Thus, as toggle (1210) continues pivoting to the position shown in FIG. 21C, first drive shaft (244) is rotated relative to first sheath (240) to open first grasping arm (210) and release needle (50) after second grasping arm (250) grasps needle (50). Accordingly, toggle actuation assembly (1200) is operable to transfer grip of needle (50) from first grasping arm (210) to second grasping arm (250). It should be understood from the foregoing that toggle actuation assembly (1200) is operable to rotate first drive shaft (244) in a first direction and second drive shaft (284) in a second direction that is opposite the first direction. Of course, in some versions, threaded sections (246, 248, 286, 288) and threading (228, 238, 268, 278), described above, may be configured such that drive shafts (244, 284) may be rotated in the same direction while one set of jaws (220, 230, 260, 270) closes and another set of jaws (220, 230, 260, 270) opens. Still further configurations will be apparent to one of ordinary skill in the art in view of the teachings herein.

In some versions, a user may disengage latching member (1108) from latch (1090) to pivot trigger (1102) and disengage clutch shuttle (1180) from rear drive shaft (1190). Accordingly, second grasping arm (250) may be rotated away from first grasping arm (210), such as that shown in FIG. 5D, as trigger (1102) is pivoted back to the first, unactuated position. The user may then proceed in accordance with the operation described above in reference to FIGS. 5E-5H. In some versions, the rotation of drive shafts (244, 284) is a 360 degree rotation such that the components of toggle actuation assembly (1200) are in the substantially same position regardless of which grasping arm (210, 250) is grasping needle (50). Such rotation may ensure that proximal end (1182) and/or distal end (1184) of clutch shuttle (1180) remain aligned with one or both engagement members (1134, 1192). Of course it should be understood that proximal end (1182) and distal end (1184) of the present clutch shuttle (1180) are configured to self-align via the tabs that couple to engagement members (1134, 1192), though this is merely optional. It should be understood that actuating toggle (1210) in the reverse of FIGS. 21A-21C will reverse the above-described actions and transfer needle (50) from second grasping arm (250) to first grasping arm (210). Trigger (1102) may then be pivoted back to the first, unactuated position to reset the instrument.

Figure 23:
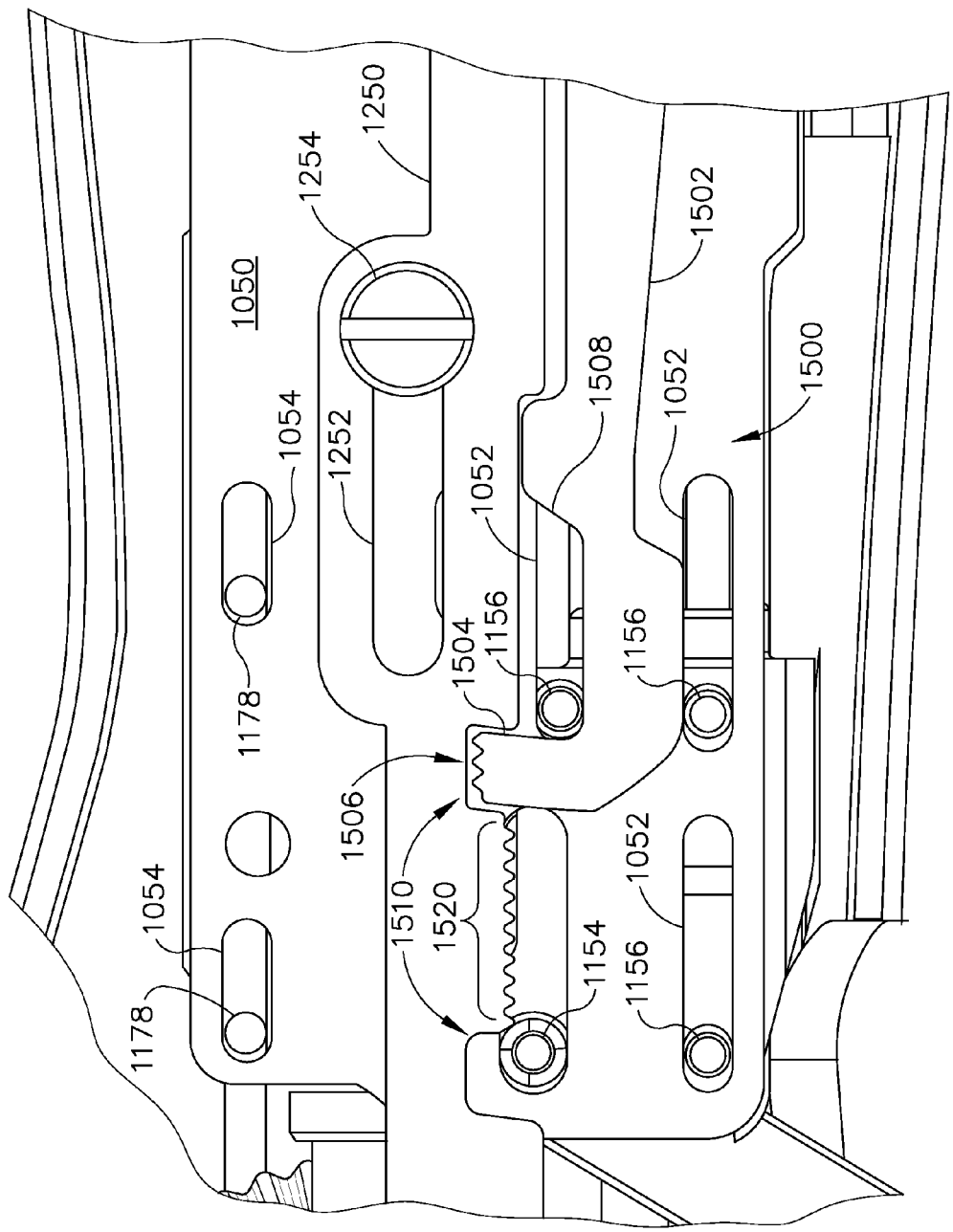
FIG. 23 depicts an enlarged side elevation view of an exemplary handle assembly having a lock assembly.

In some versions, a locking feature (1500) is resiliently rotatably mounted to frame (1050) and is configured to engage with rack (1250) to prevent rack (1250) from actuating unless locking feature (1500) is released, as shown in FIGS. 16 and 23. In the present example, locking feature (1500) is configured to release when clutch assembly (1150) has been actuated. Such a locking feature (1500) may be provided to reduce inadvertent actuation of rack (1250) by toggle (1210) when clutch assembly (1150) has not been engaged. In the present example, locking feature (1500) comprises a pivotable lock arm (1502) having a set of teeth (1506) on the end of a perpendicular finger (1504). As noted above, rack (1250) includes a pair of notches (1510) and teeth (1520) configured to engage with finger (1504) and/or teeth (1506), respectively. A camming surface (1508) extends from lock arm (1502) and is configured to pivot lock arm (1502) away from engagement with notches (1510) and/or teeth (1520) when a pin (1156) of first clutch member (1152) encounters camming surface (1508).

As shown in FIG. 23, when first clutch member (1152) has not been actuated by trigger (1102), finger (1504) is within a notch (1510) and substantially prevents rack (1250) from actuating distally. As first clutch member (1152) is actuated distally, pin (1156) slides within longitudinal slot (1052) until pin (1156) encounters camming surface (1508). As first clutch member (1152) continues to actuate distally, arm (1502) is pivoted away from rack (1250) to disengage finger (1504) from notch (1510). A spring (not shown) biases arm (1502) back towards rack (1250). While first clutch member (1152) is in the second, actuated position, arm (1502) remains disengaged from rack (1250). Thus, only while first clutch member (1152) is actuated (and therefore clutch shuttle (1180) is engaged with rear drive shaft (1190)), is rack (1250) longitudinally actuatable by toggle (1210). If the clutch assembly (1150) disengages while the user is actuating rack (1250), teeth (1506, 1520) engage to maintain the position of rack (1250). In some versions, teeth (1506, 1520) may comprise ratcheting teeth to provide a ratchet for rack (1250). Once toggle (1210) has been pivoted to the rearward-most position, shown in FIG. 21C, finger (1504) is again aligned with a notch (1510) and subsequently engages with notch (1510) when clutch assembly (1150) is disengaged. In some versions, a disengagement feature (not shown), such as a lever extending out of casing (1002), is provided to manually disengage locking feature (1500). Such a disengagement feature may be used to allow a user to open first or second grasping arm (210, 250) via toggle (1210) to initially load or remove needle (50). Of course other configurations locking feature (1500) will be apparent to one of ordinary skill in the art in view of the teachings herein. By way of example only, a cam may extend from either first clutch member (1152) or second clutch member (1170) to disengage a spring-loaded tab from one or more recesses in rack (1250).

C. Exemplary Button Toggle Assembly

Figure 24:
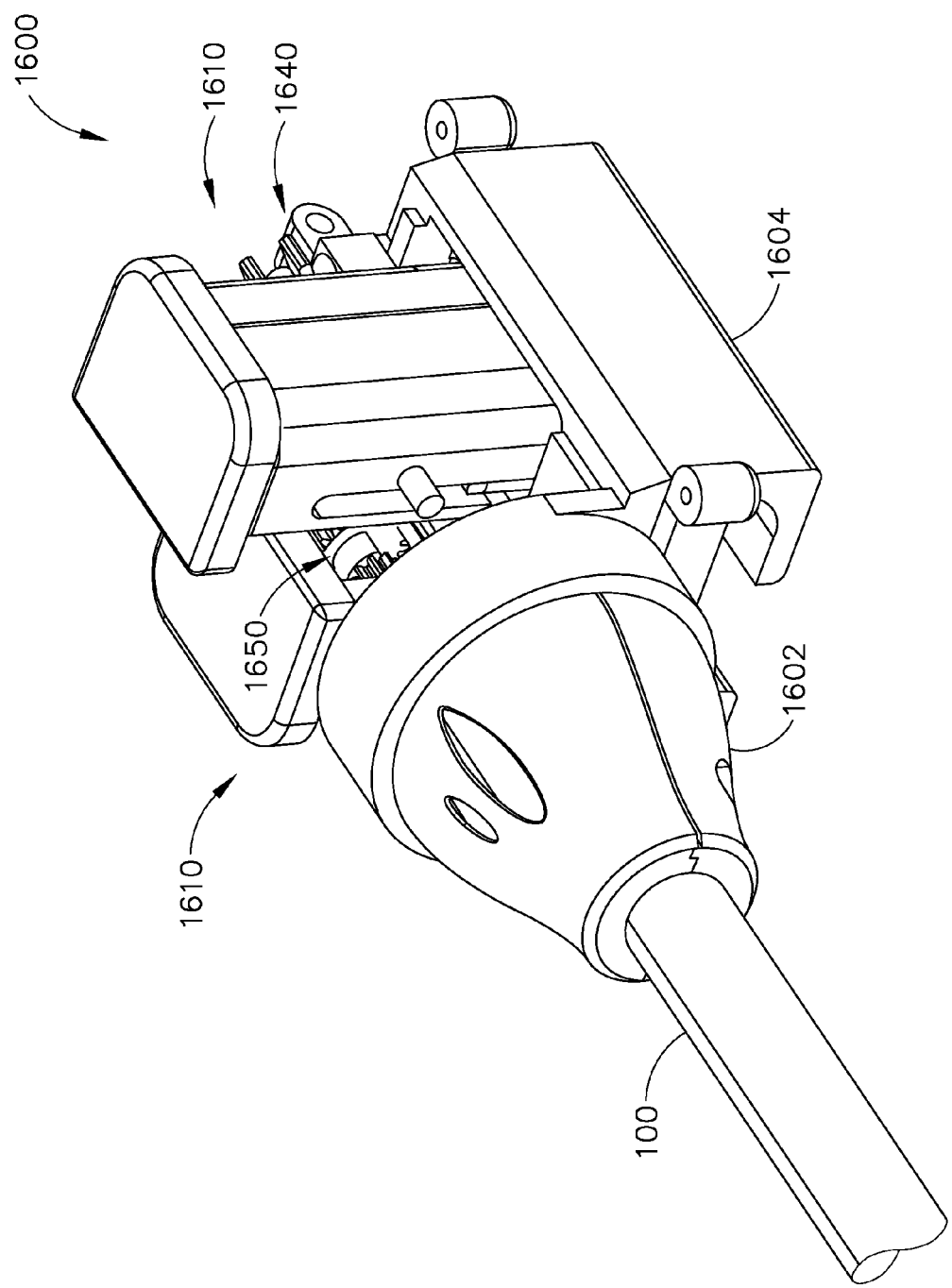
FIG. 24 depicts a perspective view of an exemplary button toggle assembly.
Figure 25:
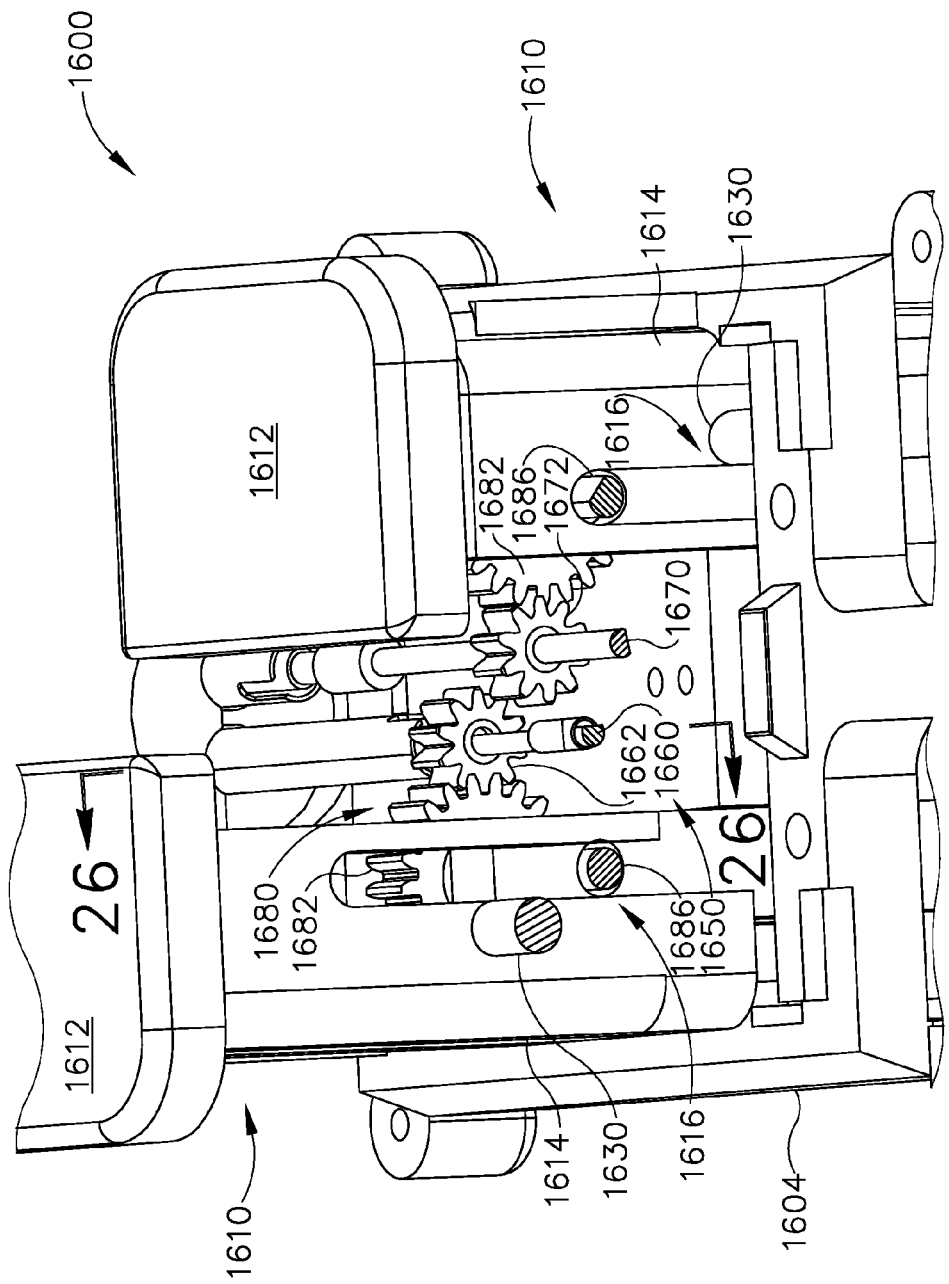
FIG. 25 depicts a rear perspective cross-sectional view of the button toggle assembly of FIG. 24 with a rear portion removed to show an exemplary gear assembly.

In some instances, it may be preferable to transfer control of needle (50) from first grasping arm (210) to second grasping arm (250) using a side-by-side assembly. Such an arrangement may be useful to reduce the overall length of instrument (10). Accordingly, one merely exemplary button toggle assembly (1600) is depicted in FIGS. 24-27. As shown in FIG. 24, button toggle assembly (1600) is coupled to a proximal end of shaft (100) via a nosecone (1602). Button toggle assembly (1600) comprises a base (1604), a pair of toggle buttons (1610), a rotatable guide member (1640), and an actuation assembly (1650). Referring to FIG. 25, each button (1610) includes a top member (1612), a main body (1614), a pair of vertical tracks (1616), a rack (1620) (shown in FIG. 26), and a guide pin (1630). Top member (1612) comprises a flat surfaced member that is operable by a user to depress a corresponding button (1610). In some versions, top member (1612) may include a frictional or slip-resistant material to provide additional grip to a user. Main body (1614) extends downwardly from top member (1612) and, in the present example, comprises a substantially U-shaped member with the open end oriented inwardly toward actuation assembly (1650). Each main body (1614) is slidably mounted to base (1604) via vertical tracks (1616) and an axle (1686) of actuation assembly (1650) extending through main body (1614). Main bodies (1614) also each include a guide pin (1630) that extends proximally and is configured to engage with rotatable guide member (1640), as will be discussed in greater detail below. Of course other buttons (1610) may be constructed as will be apparent to one of ordinary skill in the art in view of the teachings herein.

Figure 26:
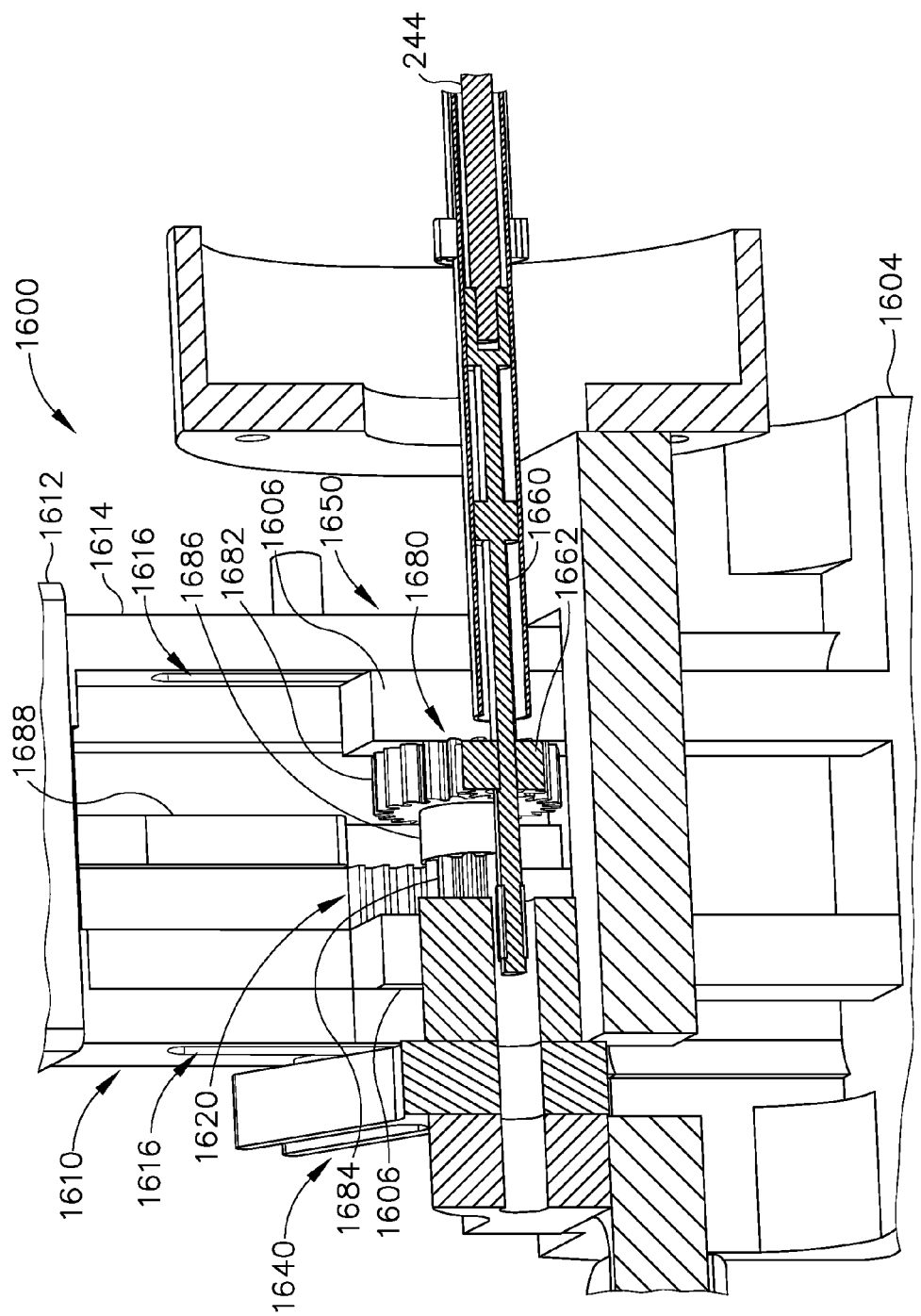
FIG. 26 depicts a side perspective cross-sectional view of the button toggle assembly of FIG. 24 taken along section 26-26 of FIG. 25.

Actuation assembly (1650) is operable to rotate first and second drive shafts (244, 284) to transfer control of needle (50) from first grasping arm (210) to second grasping arm (250). As shown in FIG. 25, actuation assembly (1650) comprises a first adapter shaft (1660), a second adapter shaft (1670), and a pair of pinion assemblies (1680). Referring to FIG. 26, first adapter shaft (1660) is rotatably coupled at a first end to first drive shaft (244) and includes a first intermediate gear (1662) fixedly coupled to first adapter shaft (1660) at a point proximal to first drive shaft (244). First intermediate gear (1662) is configured to mesh with and engage with a second intermediate gear (1682) of pinion assembly (1680). In the example shown in FIGS. 25-26, second intermediate gear (1682) and a pinion gear (1684) are fixedly coupled to an axle (1686). Axle (1686) is rotatably mounted to base (1604) via vertical protrusions (1606), as shown in FIG. 26. Pinion gear (1684) engages with rack (1620) of a first button (1610) such that when button (1610) is moved upwardly or downwardly, rack (1620) engages and turns pinion gear (1684), thereby rotating first drive shaft (244) via first adapter shaft (1660). In the present example, button (1610) further includes a boss (1688) on button (1610) that engages a substantially flat cam surface of axle (1686) to substantially prevent rotation of axle (1686) when rack (1620) is not engaged with pinion gear (1684). Accordingly, boss (1688) may reduce inadvertent rotation of first drive shaft (244) when button (1610) is not being actuated. Of course, in some versions pinion assembly (1680) may be omitted and first intermediate gear (1662) may directly engage with rack (1620).

In the present example, second adapter shaft (1670) and a second pinion assembly (1680) are substantially identical to the assembly described above. Second adapter shaft (1670) is rotatably coupled at a first end to second drive shaft (284) and includes a first intermediate gear (1672) fixedly coupled to second adapter shaft (1670) at a point proximal to second drive shaft (284). First intermediate gear (1672) is configured to mesh with and engage with a second intermediate gear (1682) of a second pinion assembly (1680). Similar to that described above, second intermediate gear (1682) and a pinion gear (1684) are fixedly coupled to an axle (1686). Axle (1686) is rotatably mounted to base (1604) via vertical protrusions (1606), as shown in FIG. 26. Pinion gear (1684) engages with rack (1620) of a second button (1610) such that when button (1610) is moved upwardly or downwardly, rack (1620) engages and turns pinion gear (1684), thereby rotating second drive shaft (284) via second adapter shaft (1670). In the present example, button (1610) further includes a boss (1688) on second button (1610) that engages a substantially flat cam surface of axle (1686) to substantially prevent rotation of axle (1686) when rack (1620) is not engaged with pinion gear (1684). Accordingly, boss (1688) may also reduce inadvertent rotation of second drive shaft (284) when button (1610) is not being actuated. Of course, in some versions pinion assembly (1680) may be omitted and first intermediate gear (1672) may directly engage with rack (1620). Still other configurations for actuation assembly (1650) will be apparent to one of ordinary skill in the art in view of the teachings herein.

Figure 27:
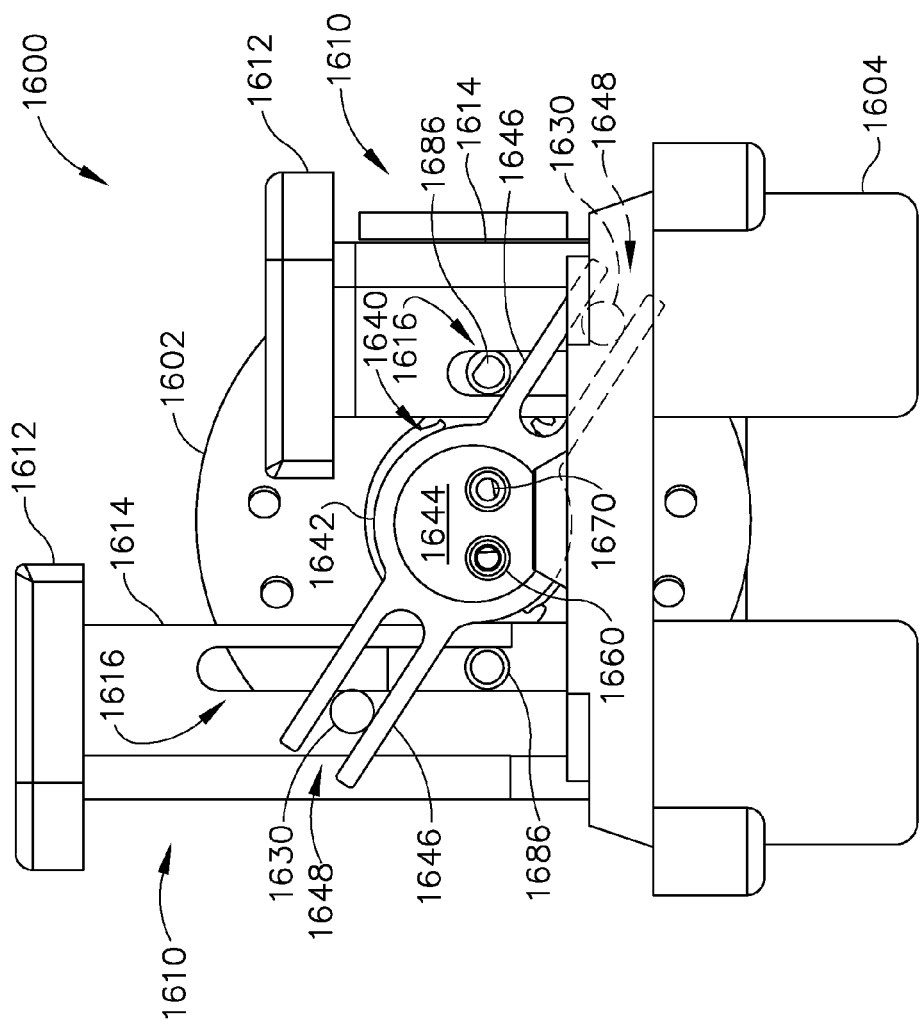
FIG. 27 depicts a rear elevation view of the button toggle assembly of FIG. 24.

As demonstrated by the foregoing, buttons (1610) are operable to rotate first and second drive shafts (244, 284) via racks (1620). It should be understood that when the button (1610) associated with first drive shaft (244) is depressed toward base (1604), first drive shaft (244) rotates a first direction. In the present example, such rotation is operable to cause first grasping arm (210) to grab needle (50). To release needle (50) from second grasping arm (250), second drive shaft (284) of the present example rotates in a second direction that is opposite to the first direction. Accordingly, in the present arrangement, second button (1610) is configured to actuate vertically when first button (1610) is depressed. Thus, buttons (1610) are configured to simultaneously actuate in opposing directions. As shown in FIG. 27, a rotatable guide member (1640) is configured to engage guide pins (1630) of buttons (1610) to achieve this motion. In the example shown, guide member (1640) comprises a rotatable center (1642) disposed about an axle (1644) and a pair of forked members (1646) extending outwardly from center (1642). A recess (1648) of each forked member (1646) receives guide pin (1630). Accordingly, as a first button (1610) is actuated downwardly, rotatable guide member (1640) urges the second button (1610) upwardly via forked member (1646) and guide pin (1630) and vice-versa when second button (1610) is depressed.

While one merely exemplary button toggle assembly (1600) has been described, other toggle assemblies (1600) will be apparent to one of ordinary skill in the art in view of the teachings herein. For example, in one version, a single central button having opposing racks may be configured to simultaneously rotate both adapter shafts (1660, 1670) in opposing directions. Such a single central button may selectively lock into place relative to base (1604) when actuated downwardly in a similar fashion to a clicking pen. In yet a further alternative, a single slider may include a pair of racks that engage actuation assembly (1650) such that the sliding motion of the slider rotates first drive shaft (244) in a first direction while second drive shaft (284) is rotated in an opposite direction.

D. Exemplary Vertical Rack Assembly

Figure 28:
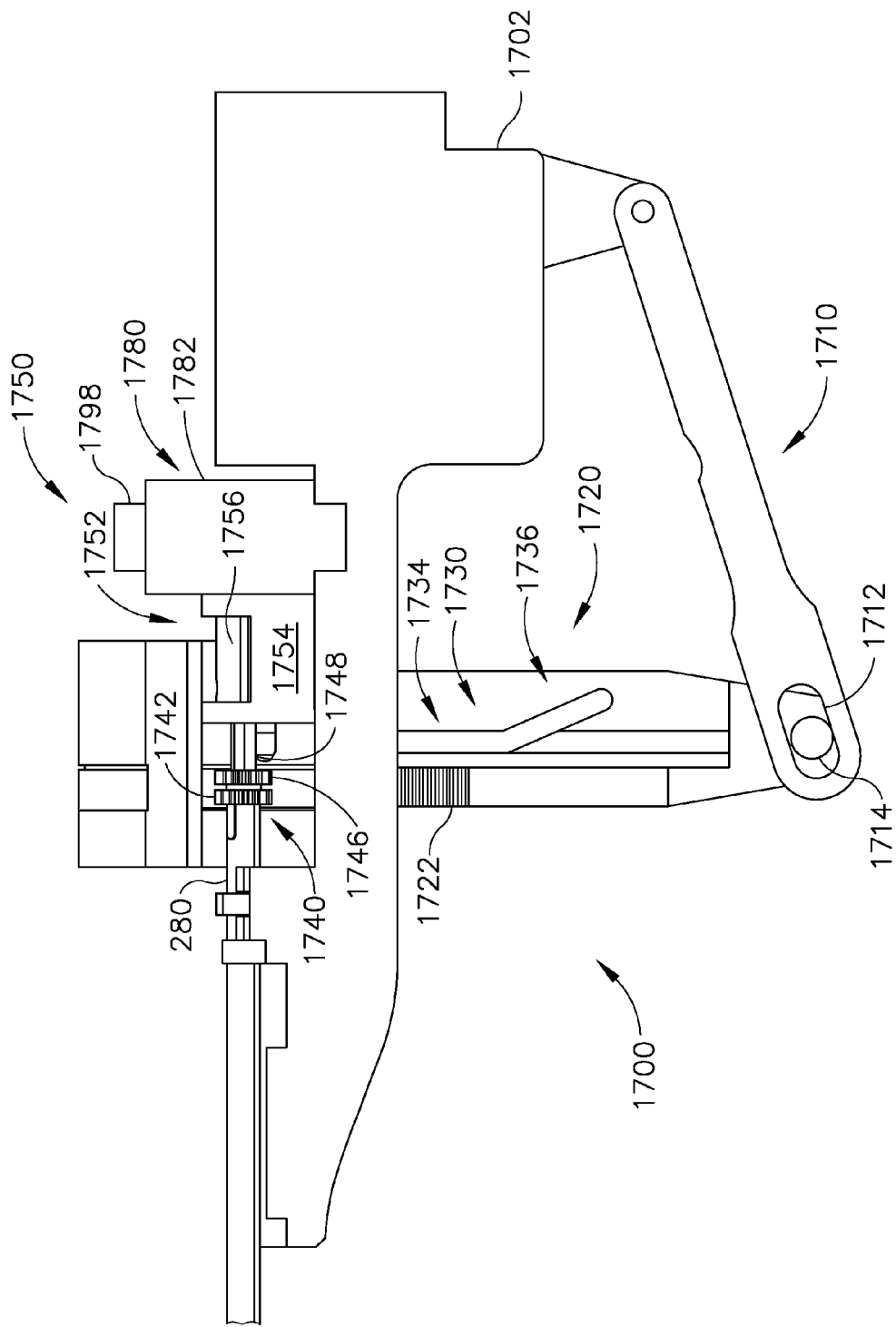
FIG. 28 depicts a side elevation view of an exemplary vertical rack assembly.

While the foregoing example described an alternative assembly to rotate first and second drive shafts (244, 284), in some versions it may be preferable to have a vertically actuatable assembly to rotate second grasping arm (250) and/or to disengage a clutch coupled to one or more of the drive shafts (244, 284) similar to clutches assemblies (640, 1250) described above. One merely exemplary vertical rack assembly (1700) is depicted in FIGS. 28-30C. As shown in FIG. 28, vertical rack assembly (1700) comprises a pivotable arm (1710), a rack assembly (1720), a pinion assembly (1740), and a clutch assembly (1750). In the present example, pivotable arm (1710) is pivotably mounted at a first end to a base (1702) and at a second end to rack assembly (1720). Accordingly, in the present example, pivotable arm (1710) may operate similarly to a trigger such that a user may grasp pivotable arm (1710) to actuate rack assembly (1720). In the example shown, pivotable arm includes a slot (1712) that receives a pin (1714) of rack assembly (1720) therein and is sized such that pin (1714) slides within slot (1712) as rack assembly (1720) is actuated upwardly or downwardly relative to base (1702). In some versions, pivotable arm (1710) may be resiliently biased to maintain rack assembly (1720) in a first, unactuated position, such as that shown in FIG. 28. Of course other components, constructions, and/or features for pivotable arm (1710) will be apparent to one of ordinary skill in the art in view of the teachings herein.

Rack assembly (1720) of the present example includes a rack (1722), a slot (1730), and pin (1714) located at a first end of rack assembly (1720). As best seen in FIGS. 30A-30C, slot (1730) includes three portions, a first angled portion (1732), a second vertical portion (1734), and a third angled portion (1736). Slot (1730) and the different portions (1732, 1734, 1736) are configured to control the longitudinal motion of clutch assembly (1750) via a riding pin (1760) (shown best in FIG. 29) that extends transversely from clutch assembly (1750) and into slot (1730), as will be described in greater detail below. Rack (1722) comprises a plurality of teeth configured to engage with and rotate pinion assembly (1740). In the present example, rack (1722) is positioned substantially in alignment with vertical portion of slot (1734) such that pinion assembly (1740) engages rack (1722) only when clutch assembly (1750) is disengaged, as will be described below. Still other configurations for rack assembly (1720) will be apparent to one of ordinary skill in the art in view of the teachings herein.

Figure 29:
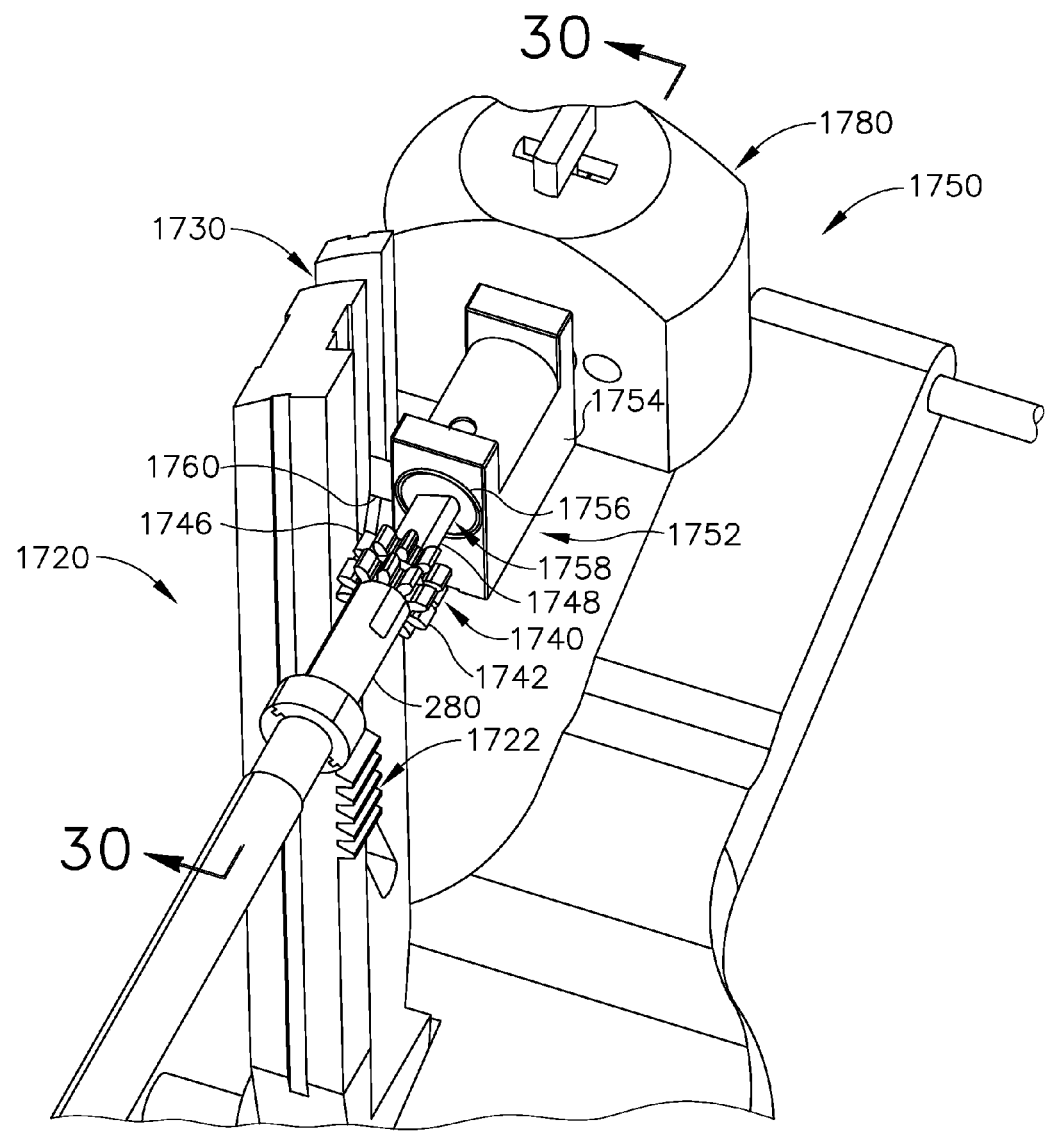
FIG. 29 depicts an enlarged perspective view of the vertical rack assembly of FIG. 28 with portions of the assembly removed to show an exemplary second driveshaft and clutch.
Figure 30A:
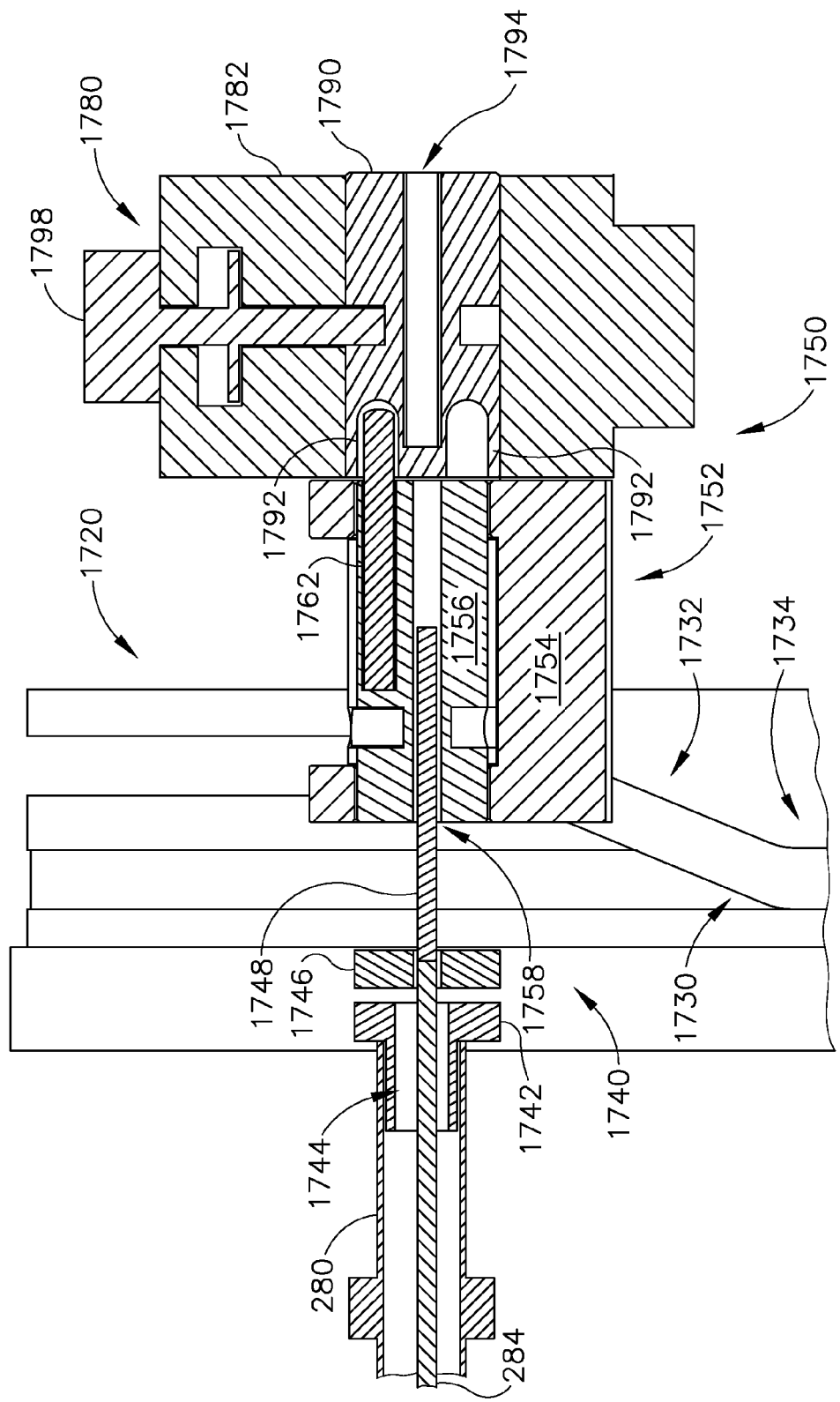
FIG. 30A depicts an enlarged side cross-sectional view of the vertical rack assembly of FIG. 29 taken along section line 30-30 in FIG. 29 showing the clutch and rack in a first position.
Figure 30B:
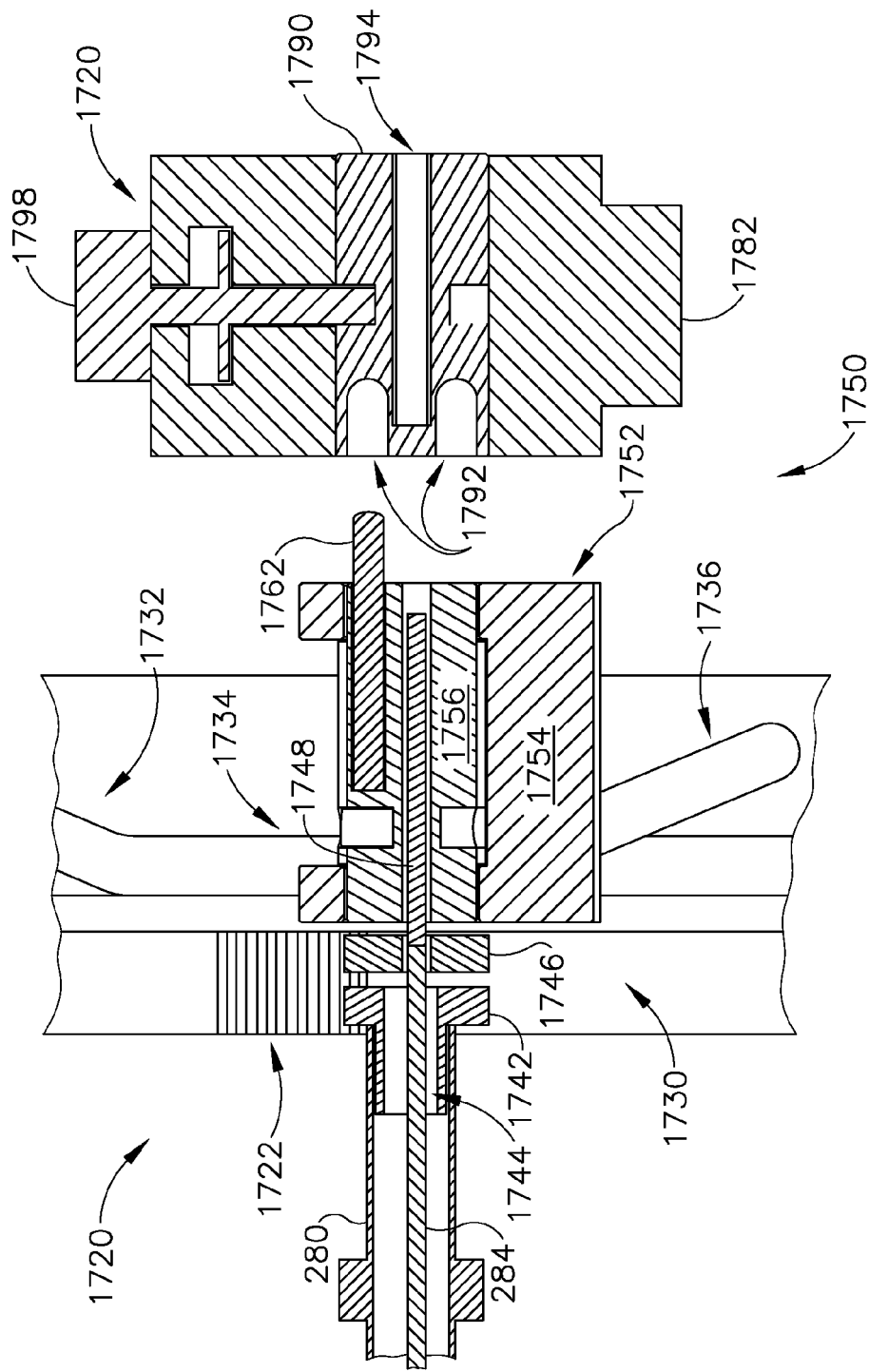
FIG. 30B depicts an enlarged side cross-sectional view of the vertical rack assembly of FIG. 30A taken along section line 30-30 in FIG. 29 showing the clutch and rack in a second position.
Figure 30C:
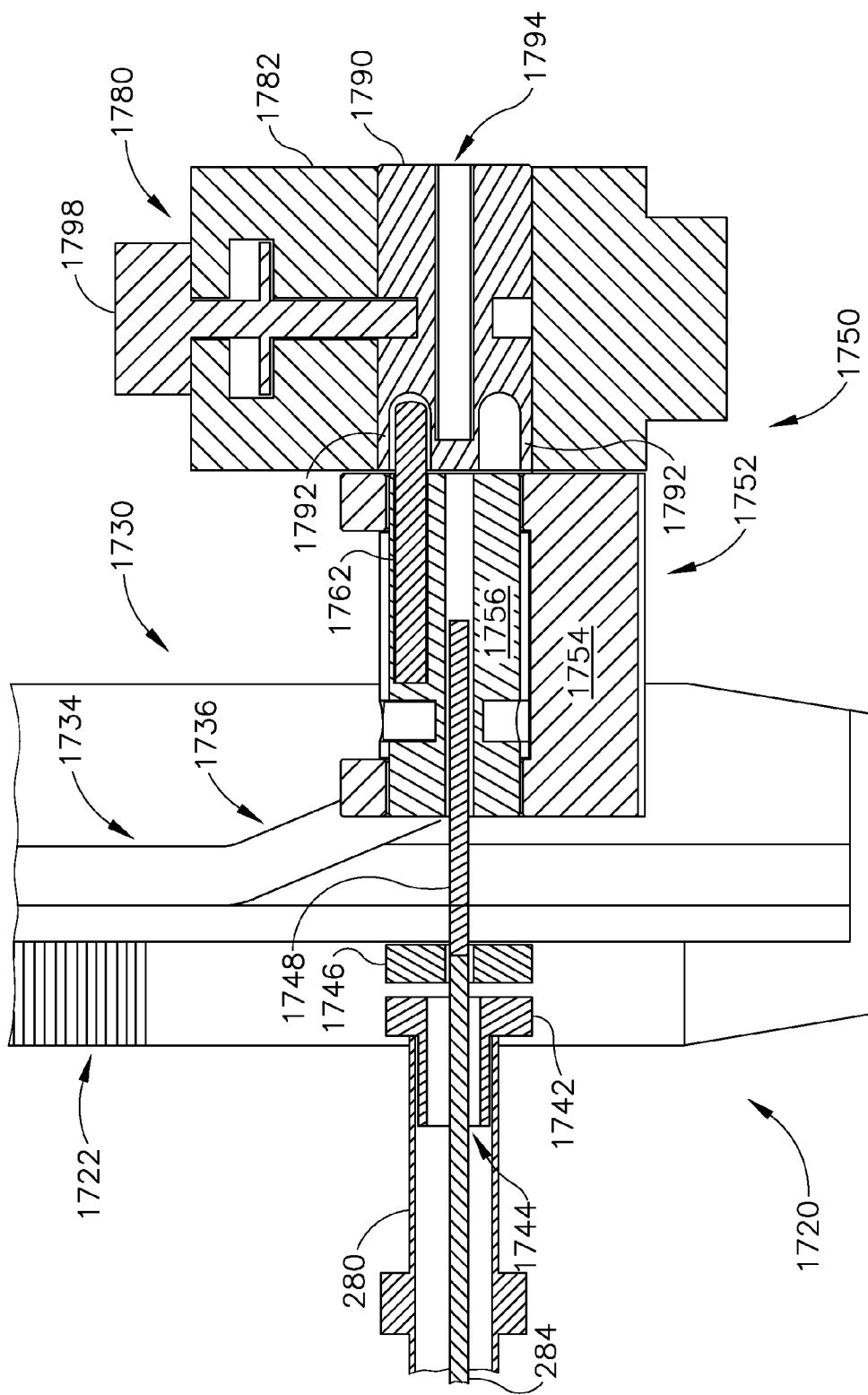
FIG. 30C depicts an enlarged side cross-sectional view of the vertical rack assembly of FIG. 30A taken along section line 30-30 in FIG. 29 showing the clutch and rack in a third position.

Referring to FIG. 29, pinion assembly (1740) comprises a sheath gear (1742), a shaft gear (1746), and a clutch shaft (1748). Sheath gear (1742) is engaged with second sheath (280) such that rotation of sheath gear (1742) also rotates second sheath (280). By way of example only, sheath gear (1742) may be fixedly coupled to second sheath (280) and/or have features, such as spline features, to couple sheath gear (1742) to second sheath (280). As shown in FIGS. 30A-30C, sheath gear (1742) includes an opening (1744) therethrough to permit second drive shaft (284) to extend through sheath gear (1742) without engaging with sheath gear (1742). Accordingly, second drive shaft (284) is rotatable relative to second sheath (280). Referring back to FIG. 29, a shaft gear (1746) is engaged with second drive shaft (284) such that rotation of shaft gear (1746) also rotates second drive shaft (284). Similar to sheath gear (1742), shaft gear (1746) may be fixedly coupled to second drive shaft (284) and/or have features, such as spline features, to couple shaft gear (1746) to second drive shaft (284). A clutch shaft (1748) extends from shaft gear (1746) and includes a keyed portion that is configured to insert into a keyed opening (1758) of clutch barrel (1756) of clutch assembly (1750), as will be described below. In the present example, sheath gear (1742) and shaft gear (1746) are both configured to simultaneously engage rack (1722) when rack assembly (1720) is actuated relative to pinion assembly (1740). When sheath gear (1742) and shaft gear (1746) engage rack (1722), vertical rack assembly (1700) is operable to rotate second grasping arm (250) about axis (140) described above and shown in FIG. 5C. Further arrangements for pinion assembly (1740) will be apparent to one of ordinary skill in the art in view of the teachings herein.

Referring to FIGS. 28-30C, clutch assembly (1750) of the present example comprises a first member (1752) and a second member (1780). First member (1752) comprises a clutch body (1754), a clutch barrel (1756) rotatably disposed within clutch body (1754), a riding pin (1760) extending transversely from clutch body (1754), and a transfer shaft (1762) extending proximally from clutch barrel (1756). As shown in FIGS. 29-30A, clutch barrel (1756) includes a keyed opening (1758) that is configured to receive clutch shaft (1748) of pinion assembly (1740) at a distal end of clutch barrel (1756). In the present example, first member (1752) is configured to longitudinally slide along clutch shaft (1748) without disengaging from clutch shaft (1748) as first member (1752) is actuated longitudinally via riding pin (1760), as will be described below. Transfer shaft (1762) is fixedly coupled to clutch barrel (1756) and is operable to rotate clutch barrel (1756) relative to clutch body (1754). As will be described in greater detail below, transfer shaft (1762) is configured to engage one or more openings (1792) in a transfer member (1790) of second member (1780). Accordingly, second drive shaft (284) is rotated via clutch barrel (1756) and clutch shaft (1748) when transfer member (1790) is rotated and transfer shaft (1762) is engaged with an opening (1792).

Figure 31:
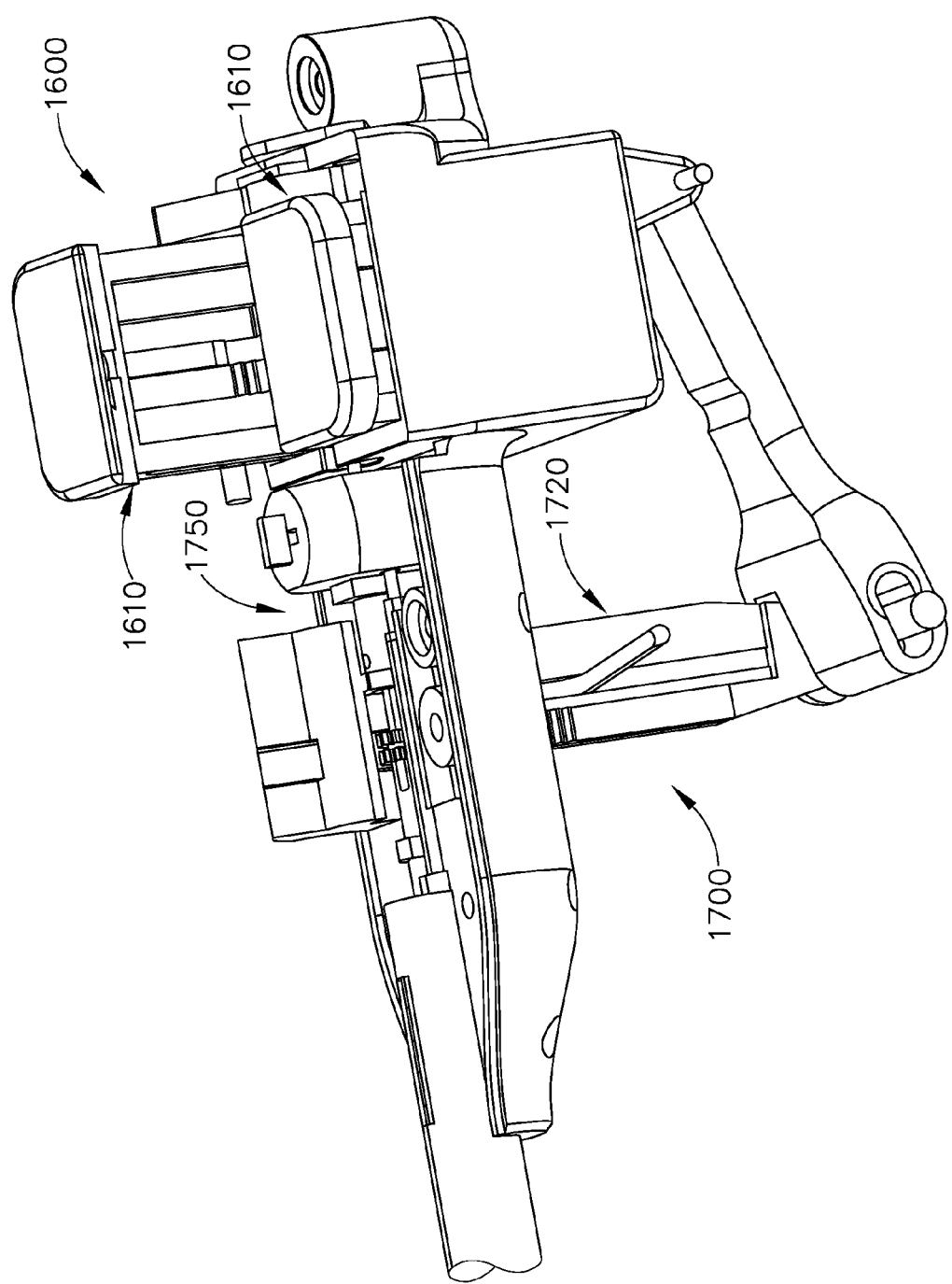
FIG. 31 depicts an exemplary combination button toggle and vertical rack assembly.

As shown in FIG. 30A, second member (1780) comprises an outer member (1782), a rotatable transfer member (1790) disposed within outer member (1782), and a locking member (1798) configured to selectively lock transfer member (1790) relative to outer member (1782). In the present example, outer member (1782) is fixed to base (1702) (shown in FIG. 28) to provide a mechanical ground for second member (1780). Transfer member (1790) includes a plurality of openings (1792) positioned in a circle on a distal face of transfer member (1790). A central opening (1794) positioned at the axial center of openings (1792) provides an interface from a proximal end of transfer member (1790). As shown in FIG. 31, a button toggle assembly, such as button toggle assembly (1600) may interface with transfer member (1790) to permit a user to rotate transfer member (1790) via buttons (1610). Of course other configurations for second member (1780) will be apparent to one of ordinary skill in the art in view of the teachings herein.

In the present example, riding pin (1760) extends into slot (1730) and is operable to longitudinally actuate first member (1752) relative to second clutch member (1780). As shown FIG. 30A, when riding pin (1760) is within first angled portion (1732), transfer shaft (1762) is inserted into an opening (1792) of transfer member (1790) of second member (1780). In this position, rotation of transfer member (1790) is operable to rotate second drive shaft (284) while second sheath (280) remains rotationally stationary. As rack assembly (1720) is actuated vertically, slot (1730) urges riding pin (1760) and first member (1752) distally to disengage transfer shaft (1762) from opening (1792). As shown in FIG. 30B, when riding pin (1760) is within second vertical portion (1734), transfer shaft (1762) is fully disengaged from transfer member (1790) of second member (1780). As rack assembly (1720) travels vertically relative to clutch assembly (1750), rack (1722) engages pinion assembly (1740) to rotate both second sheath (280) and second drive shaft (284) while transfer shaft (1762) is disengaged. In some versions, rack (1722) may be configured to rotate pinion assembly (1740) 360 degrees to maintain the angular position of transfer shaft (1762) relative to transfer member (1790), though this is merely optional. As rack assembly (1720) continues to actuate vertically, as shown in FIG. 30C, third angled portion (1736) urges riding pin (1760) and first member (1752) proximally to reengage transfer shaft (1762) with an opening (1792) of transfer member (1790). In this position, rotation of transfer member (1790) is operable to rotate second drive shaft (284) while second sheath (280) remains rotationally stationary.

Of course further constructions for vertical rack assembly (1700) will be apparent to one of ordinary skill in the art in view of the teachings herein. For example, in one version first angled portion (1732) of slot (1730) may be omitted such that first member (1752) of clutch assembly (1750) is initially disengaged from second member (1780) and is only engaged once rack assembly (1720) is actuated upwardly such that clutch assembly (1750) is urged proximally via third angled portion (1736).

VI. Miscellaneous

It should be understood that while the aforementioned assemblies are described in reference to manual actuation, motors, actuators, or other automated components may be used to actuate the above assemblies.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a shaft, wherein the shaft has a distal end and a proximal end;
   (b) an end effector located at the distal end of the shaft, wherein the end effector comprises:
      (i) a first needle grasping member, and
      (ii) a second needle grasping member,
      wherein the first needle grasping member and second needle grasping member are each operable to grasp and release a suture needle; and
   (c) a handle assembly coupled to the proximal end of the shaft, the handle assembly comprising a trigger-operated actuation assembly, wherein the trigger-operated actuation assembly is operable to:
      (i) actuate the first needle grasping member to selectively grasp and release the suture needle,
      (ii) actuate the second needle grasping member to selectively grasp and release the suture needle, and
      (iii) rotate the second needle grasping member relative to the shaft and the first needle grasping member about an axis that is parallel to the longitudinal axis of the shaft as the first needle grasping member remains stationary.

2. The apparatus of claim 1 wherein the handle assembly is operable to sequentially grasp the needle with the second needle grasping member and release the needle from the first needle grasping member.

3. The apparatus of claim 1 wherein the handle assembly comprises a casing and wherein the trigger-operated actuation assembly comprises:
   (i) a trigger pivotably mounted to the casing, and
   (ii) a trigger gear assembly, wherein the trigger gear assembly interfaces with the trigger and is operable to rotate the second needle grasping member relative to the shaft.

4. The apparatus of claim 3 wherein the trigger-operated actuation assembly further comprises a clutch assembly, wherein trigger is operable to selectively actuate the clutch assembly relative to the casing.

5. The apparatus of claim 4 wherein the second needle grasping member is coupled to a second outer sheath and a second drive shaft, wherein the clutch assembly is further operable to selectively couple the second outer sheath to the second drive shaft.

6. The apparatus of claim 5 wherein the clutch assembly comprises a first member and a second member, wherein the first member is actuatable relative to the casing via the trigger, wherein the second member is coupled to the second outer sheath and rotatable relative to the first member, and wherein the second member is configured to selectively couple to the second drive shaft.

7. The apparatus of claim 4 wherein the trigger is operable to sequentially rotate the second needle grasping member relative to the shaft and actuate the clutch assembly relative to the casing.

8. The apparatus of claim 1 wherein the handle assembly further comprises a toggle actuation assembly, wherein the toggle actuation assembly is operable to grasp and release the suture needle with the first needle grasping member and the second needle grasping member.

9. The apparatus of claim 8 wherein the first needle grasping member is coupled to a first outer sheath and a first drive shaft, and wherein the second needle grasping member is coupled to a second outer sheath and a second drive shaft, wherein the toggle actuation assembly is operable to rotate the first drive shaft in a first direction and the second drive shaft in a second direction.

10. The apparatus of claim 9 wherein the handle assembly comprises a casing and wherein the toggle actuation assembly comprises:
    (i) a toggle pivotably mounted to the casing,
    (ii) an actuatable rack assembly coupled to the toggle,
    (iii) a first drive train in communication with the rack assembly, and
    (iv) a second drive train in communication with the rack assembly, wherein the first drive train is operable to rotate the first drive shaft, wherein the second drive train is operable to rotate the second drive shaft.

11. The apparatus of claim 10 wherein the rack assembly comprises a first rack gear section and a second rack gear section, wherein the first rack gear section engages the first drive train and the second rack gear section engages the second drive train.

12. The apparatus of claim 11 wherein the first rack gear section is positioned relative to the second rack gear section such that the first rack gear section engages the first drive train successively to the second rack gear section engaging the second drive train.

13. The apparatus of claim 8 further comprising a locking feature, wherein the locking feature is operable to selectively lock the toggle actuation assembly.

14. The apparatus of claim 13 wherein the locking feature is in communication with the trigger-operated actuation assembly, wherein the trigger-operated actuation assembly is operable to selectively disengage the locking feature from the toggle actuation assembly.

15. The apparatus of claim 13 wherein the locking feature comprises a lever, wherein the lever is operable to disengage the locking feature from the toggle actuation assembly.

16. An apparatus comprising:
    (a) a shaft, wherein the shaft has a distal end and a proximal end;
    (b) an end effector located at the distal end of the shaft, wherein the end effector comprises:
       (i) a first needle grasping member, and
       (ii) a second needle grasping member,
       wherein the first needle grasping member and second needle grasping member are each operable to grasp and release a suture needle; and
    (c) a handle assembly coupled to the proximal end of the shaft, the handle assembly comprising a toggle actuation assembly, wherein the toggle actuation assembly is operable to grasp and release the suture needle with the first needle grasping member and the second needle grasping member, wherein the toggle actuation assembly comprises:
       (i) a first drive member,
       (ii) a second drive member, wherein the second drive member is configured to move to thereby cause the first needle grasping member to grasp and release the suture needle, wherein the first drive member is operable to move through a first range of motion to thereby cause movement of the second drive member, and (iii) a third drive member, wherein the third drive member is configured to move to thereby cause the second needle grasping member to grasp and release the suture needle, wherein the first drive member is configured to move through a second range of motion to thereby cause movement of the third drive member.

17. The apparatus of claim 16 wherein the first needle grasping member is coupled to a first outer sheath and a first drive shaft, and wherein the second needle grasping member is coupled to a second outer sheath and a second drive shaft, wherein the second drive member is operable to rotate the first drive shaft in a first direction, wherein the third drive member is operable to rotate the second drive shaft in a second direction.

18. The apparatus of claim 16 wherein the first range of motion and the second range of motion overlap.

19. An apparatus comprising:
(a) a shaft, wherein the shaft has a distal end and a proximal end;
(b) an end effector located at the distal end of the shaft, wherein the end effector comprises:
  (i) a first needle grasping member comprising:
    (A) a first jaw,
    (B) a second jaw translatable relative to the first jaw,
    (C) a first outer sheath supporting the first jaw and the second jaw and fixedly coupled to the shaft, and
    (D) a first drive shaft extending through the first outer sheath and rotatable relative to the first outer sheath, wherein the first drive shaft is operable to longitudinally actuate the first jaw and the second jaw to grasp a needle, and
  (ii) a second needle grasping member comprising:
    (A) a third jaw,
    (B) a fourth jaw translatable relative to the third jaw,
    (C) a second outer sheath supporting the third jaw and the fourth jaw and rotatably coupled to the shaft, and
    (D) a second drive shaft extending through the second outer sheath and rotatable relative to the second outer sheath,
    wherein the second drive shaft is operable to longitudinally actuate the third jaw and the fourth jaw to grasp a needle; and
(c) a handle assembly coupled to the proximal end of the shaft, the handle assembly comprising a trigger-operated actuation assembly and a toggle actuation assembly, wherein the trigger-operated actuation assembly is operable to rotate the second outer sheath and the second drive shaft substantially simultaneously, and wherein the toggle actuation assembly is operable to rotate the first drive shaft independently relative to the first outer sheath and rotate the second drive shaft independently relative to the second outer sheath.

20. The apparatus of claim 19 wherein the trigger-operated actuation assembly comprises a vertically actuatable rack.

* * * * *